United States Patent
Egbertson et al.

(10) Patent No.: US 7,323,460 B2
(45) Date of Patent: *Jan. 29, 2008

(54) N-(SUBSTITUTED BENZYL)-8-HYDROXY-1,6-NAPHTHYRIDINE-7-CARBOXAMIDES USEFUL AS HIV INTEGRASE INHIBITORS

(75) Inventors: Melissa Egbertson, Ambler, PA (US); H. Marie Langford, Lansdale, PA (US); Jeffrey Y. Melamed, Warminster, PA (US); John S. Wai, Harleysville, PA (US); Wei Han, West Chester, PA (US); Debbie S. Perlow, East Greenville, PA (US); Linghang Zhuang, Chalfont, PA (US); Mark Embrey, North Wales, PA (US)

(73) Assignee: Merck & Co., Inc., Rahway, NJ (US)

( * ) Notice: Subject to any disclaimer, the term of this patent is extended or adjusted under 35 U.S.C. 154(b) by 391 days.

This patent is subject to a terminal disclaimer.

(21) Appl. No.: 10/508,094

(22) PCT Filed: Mar. 12, 2003

(86) PCT No.: PCT/US03/07448

§ 371 (c)(1),
(2), (4) Date: Sep. 15, 2004

(87) PCT Pub. No.: WO03/077850

PCT Pub. Date: Sep. 25, 2003

(65) Prior Publication Data
US 2005/0176955 A1 Aug. 11, 2005

Related U.S. Application Data

(60) Provisional application No. 60/364,929, filed on Mar. 15, 2002.

(51) Int. Cl.
C07D 401/02 (2006.01)
A61K 31/4375 (2006.01)

(52) U.S. Cl. .......... 514/222.2; 544/3; 544/8; 544/127; 546/123; 514/222.5; 514/234.5; 514/300

(58) Field of Classification Search .......... 544/3, 544/8, 127; 514/222.5, 222.2, 300, 234.5; 546/123
See application file for complete search history.

(56) References Cited

U.S. PATENT DOCUMENTS

| | | | |
|---|---|---|---|
| 3,945,995 A | 3/1976 | Yamada et al. |
| 4,416,884 A | 11/1983 | Ishikawa et al. |
| 4,996,213 A | 2/1991 | Mendes et al. |
| 5,294,620 A | 3/1994 | Ratcliffe et al. |
| 5,633,262 A | 5/1997 | Hong et al. |
| 5,753,666 A | 5/1998 | Beasley et al. |
| 5,776,944 A | 7/1998 | Hong et al. |
| 5,945,431 A | 8/1999 | Jin et al. |
| 6,211,376 B1 | 4/2001 | Romines et al. |
| 6,262,055 B1 | 7/2001 | Young et al. |
| 6,294,547 B1 | 9/2001 | Oka et al. |
| 6,306,891 B1 | 10/2001 | Selnick et al. |
| 6,380,249 B1 | 4/2002 | Young et al. |
| 6,525,042 B1 | 2/2003 | Kobayashi et al. |
| 6,841,558 B2 | 1/2005 | Anthony et al. |
| 2003/0055071 A1 | 3/2003 | Anthony et al. |

(Continued)

FOREIGN PATENT DOCUMENTS

EP 0652218 A1 5/1995

(Continued)

OTHER PUBLICATIONS

Parrill AL. Current Medicinal Chemistry. 2003, 10(18): 1811-24, abstract (one page).*

(Continued)

*Primary Examiner*—Kahsay Habte
(74) *Attorney, Agent, or Firm*—Kenneth R. Walton; Sheldon O. Heber

(57) ABSTRACT

N-(Substituted benzyl)-8-hydroxy-1,6-naphthyridine-7-carboxamides are inhibitors of HIV integrase and inhibitors of HIV replication. The naphthyridine carboxamides are of Formula (I):

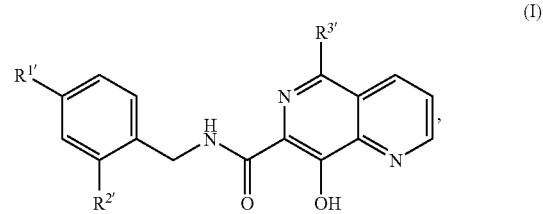

wherein $R^{1'}$, $R^{2'}$ and $R^{3'}$ are defined herein. The compounds are useful in the prevention and treatment of infection by HIV and in the prevention, delay in the onset, and treatment of AIDS. The compounds are employed against HIV infection and AIDS as compounds per se or in the form of pharmaceutically acceptable salts. The compounds and their salts can be employed as ingredients in pharmaceutical compositions, optionally in combination with other antivirals, immunomodulators, antibiotics or vaccines. Methods of preventing, treating or delaying the onset of AIDS and methods of preventing or treating infection by HIV are described.

16 Claims, No Drawings

U.S. PATENT DOCUMENTS

| | | |
|---|---|---|
| 2003/0119823 A1 | 6/2003 | Anthony et al. |
| 2004/0034221 A1 | 2/2004 | Anthony et al. |
| 2004/0039060 A1 | 2/2004 | Kiyama et al. |
| 2004/0106627 A1 | 6/2004 | Gardelli et al. |
| 2004/0127708 A1 | 7/2004 | Fuji et al. |
| 2005/0010048 A1 | 1/2005 | Zhuang et al. |

FOREIGN PATENT DOCUMENTS

| | | |
|---|---|---|
| WO | WO 96/25399 A1 | 8/1996 |
| WO | WO 98/11073 A1 | 3/1998 |
| WO | WO 98/13350 A1 | 4/1998 |
| WO | WO 99/10347 A1 | 3/1999 |
| WO | WO 99/15526 A2 | 4/1999 |
| WO | WO 99/32450 A1 | 7/1999 |
| WO | WO 99/62513 A1 | 12/1999 |
| WO | WO 99/62520 A1 | 12/1999 |
| WO | WO 99/62897 A1 | 12/1999 |
| WO | WO 00/03992 A1 | 1/2000 |
| WO | WO 00/09504 A1 | 2/2000 |
| WO | WO 01/00578 A1 | 1/2001 |
| WO | WO 02/04443 A2 | 1/2002 |
| WO | WO 02/06246 A1 | 1/2002 |
| WO | WO 02/30930 A2 | 4/2002 |
| WO | WO 03/035076 A1 | 5/2003 |
| WO | WO 03/035077 A1 | 5/2003 |
| WO | WO 03/077857 A2 | 9/2003 |
| WO | WO 03/086319 A2 | 10/2003 |

OTHER PUBLICATIONS

Zouhiri et al. J. Med. Chem. 2000, 43, 1533-1540.*

Ikeura, Y., et al., "Potent NK1 Receptor Antagonists: Synthesis and Antagonistic Activity of Various Heterocyles with an N-[3,5-Bis(trifluromethyl)benzyl]-N-methylcarbamoyl Substituent", Chemical and Pharmaceutical Bulletin, vol. 45, No. 10, pp. 1642-1652 (1997).

Ratner, L., et al., "Complete Nucleotide Sequence of the AIDS Virus, HTLV-III", Nature, vol. 313, pp. 277-284, (1985).

Toh, H., et al., "Close Structural Resemblance Between Putative Polymerase of a Drosphila Transposable Genetic Element 17.6 and Pol Gene Product of Moloney Murine Leukemia Virus", EMBO Journal, vol. 4, No. 5, pp. 1267-1272, (1985).

Power, M.D., et al., "Nucleotide Sequence of SRV-1, a Type D Simian Acquired Immune Deficiency Syndrome Retrovirus", Science, vol. 231, pp. 1567-1572, (1986).

Pearl, L.H., et al., "A Structural Model for the Retroviral Proteases", Nature, vol. 329, pp. 351-354, (1987).

Chemical Abstract No. 33-2525, Abstract of Otiai, et al., "Synthesis of 2,5 napthyridine derivatives. II", J. Pharm. Soc. Japan, vol. 58, pp. 764-770 (1938).

CAPLUS Accession No. 2002-293653, Document No. 136:309919, Abstract of WO2002/030931, Anthony et al., "Preparation of Aza- and Polyaza-naphthalenyl Carboxamides as HIV Integrase Inhibitors", p. 97 (Oct. 24, 2002).

CAPLUS Accession No. 2002-293652, Document No. 136:325531, Abstract of WO2002/030930, Anthony et al., "Preparation of Aza- and (Poly) azanaphthalenyl Carboxamides as HIV Integrase Inhibitors", p. 434 (Apr. 18, 2002).

Derwent Abstract No. 97-048296/05, Abstract of JP08301849, A. Takeda, Chem, Ind. Ltd., 1995.

CAPLUS Asccession No. 2001-923611, Document No. 136:53570, Abstract of WO2001/095905, Kiyama et al., "Dual Divalent Metal Ion Chelators as HIV Integrase Inhibitors", p. 146 (Dec. 20, 2001) (Equivalent of Cite No. 16).

Derwent Abstract No. 2002-732783, Abstract of WO02/070486, Fuji, M., New Nitrogenous Heteroaromatic Compounds are HIV Integrase Inhibitors for Treating HIV Infections, AIDS and AIDS Related Diseases, Shionogi & Co., Ltd. (2002) (Equivalent of Cite No. 17).

Chan, L., et al., "Discovery of 1,6-Naphthyridines as a Novel Class of Potent and Selective Human Cytomegalovirus Inhibitors", J. Med. Chem, vol. 42, pp. 3023-3025 (1999).

Ouali, M., et al., "Modeling of the Inhibition of Retroviral Integrases by Styrylquinoline Derivatives", J. Med. Chem., vol. 43, pp. 1949-1957 (2000).

Pommier, Y., et al., "Retroviral Integrase Inhibitors Year 2000: Update and Perspectives", Antiviral Research, vol. 47, pp. 139-148 (2000).

De Clercq, E., "New Anti-HIV Agents and Targets", Medicinal Research Reviews, vol. 22, No. 6, pp. 531-565 (2002).

Bedard, J., et al., "Antiviral Properties of a Series of 1,6-Naphthyridine and 7,8-Dihydroisoquinoline Derivatives Exhibiting Potent Activity against Human Cytomegalovirus", Antimicrobial Agents and Chemotherapy, vol. 44, No. 4, pp. 929-937 (2000).

* cited by examiner

N-(SUBSTITUTED BENZYL)-8-HYDROXY-1,6-NAPHTHYRIDINE-7-CARBOXAMIDES USEFUL AS HIV INTEGRASE INHIBITORS

This application is a 371 of PCT/US03/07448 Mar. 12, 2003, which claims benefit of U.S. provisional Application No. 60/364,929, filed Mar. 15, 2002, the disclosure of which is hereby incorporated by reference in its entirety.

FIELD OF THE INVENTION

The present invention is directed to N-(substituted benzyl)-8-hydroxy-1,6-naphthyridine-7-carboxamides and pharmaceutically acceptable salts thereof, their synthesis, and their use as inhibitors of the HIV integrase enzyme. The compounds of the present invention and their pharmaceutically acceptable salts are useful for preventing or treating infection by HIV and for treating, delaying the onset of, or preventing AIDS.

BACKGROUND OF TE INVENTION

A retrovirus designated human immunodeficiency virus (HIV) is the etiological agent of the complex disease that includes progressive destruction of the immune system (acquired immune deficiency syndrome; AIDS) and degeneration of the central and peripheral nervous system. This virus was previously known as LAV, HTLV-III, or ARV. A common feature of retrovirus replication is the insertion by virally-encoded integrase of proviral DNA into the host cell genome, a required step in HIV replication in human T-lymphoid and monocytoid cells. Integration is believed to be mediated by integrase in three steps: assembly of a stable nucleoprotein complex with viral DNA sequences; cleavage of two nucleotides from the 3' termini of the linear proviral DNA; covalent joining of the recessed 3' OH termini of the proviral DNA at a staggered cut made at the host target site. The fourth step in the process, repair synthesis of the resultant gap, may be accomplished by cellular enzymes.

Nucleotide sequencing of HIV shows the presence of a pol gene in one open reading frame [Ratner et al., Nature 1985, 313: 277]. Amino acid sequence homology provides evidence that the pol sequence encodes reverse transcriptase, integrase and an HIV protease [Toh et al., EMBO J. 1985, 4: 1267; Power et al., Science 1986, 231: 1567; Pearl et al., Nature 1987, 329: 351]. All three enzymes have been shown to be essential for the replication of HIV.

It is known that some antiviral compounds which act as inhibitors of HIV replication are effective agents in the treatment of AIDS and similar diseases, including reverse transcriptase inhibitors such as azidothymidine (AZT) and efavirenz and protease inhbitors such as indinavir and nelfinavir. The compounds of this invention are inhibitors of HIV integrase and inhibitors of HIV replication. The inhibition of integrase in vitro and of HIV replication in cells is a direct result of inhibiting the strand transfer reaction catalyzed by the recombinant integrase in vitro in HIV infected cells. A particular advantage of the present invention is highly specific inhibition of HIV integrase and HIV replication.

The following references are of interest as background:

Chemical Abstracts No. 33-2525 discloses the preparation of 5-chloro-8-hydroxy-1,6-naphthyridine-7-carboxylic acid amide from the corresponding methyl ester.

U.S. Pat. No. 5,294,620 discloses certain 1,6-naphthyridin-2-one derivatives having angiotensin II antagonist activity.

US2003/0055071 (Publication of U.S. application Ser. No. 09/973,853, filed Oct. 10, 2001) and WO 02/30930 (Publication of International Application No. PCT/US 01/31456, filed Oct. 9, 2001) each disclose certain 8-hydroxy-1,6-naphthyridine-7-carboxamides which are HIV integrase inhibitors useful, inter alia, for treating HIV infection and AIDS.

SUMMARY OF THE INVENTION

The present invention is directed to certain N-(substituted benzyl)-8-hydroxy-1,6-naphthyridine-7-carboxamides. These compounds are useful in the inhibition of HIV integrase, the prevention of infection by HIV, the treatment of infection by HIV and in the prevention, treatment, and delay in the onset of AIDS and/or ARC, either as compounds or their pharmaceutically acceptable salts, or as pharmaceutical composition ingredients, whether or not in combination with other HIV/AIDS antivirals, anti-infectives, immunomodulators, antibiotics or vaccines. The compounds of the invention have one or more polar ortho substituents in the benzyl ring. The compounds can have improved potency against replication of HIV in cells relative to similar N-(benzyl)-8-hydroxy-1,6-napthyridine carboxamides which either have no ortho substituents on the benzyl ring or have non-polar or less polar ortho substituents.

Various embodiments, aspects and features of the present invention are either further described in or will be apparent from the ensuing description, examples and appended claims.

DETAILED DESCRIPTION OF THE INVENTION

The present invention is directed to certain N-(substituted benzyl)-8-hydroxy-1,6-naphthyridine-7-carboxamide compounds. These compounds and pharmaceutically acceptable salts thereof are HIV integrase inhibitors. The compounds of the present invention are characterized by having at least one ortho polar substituent (e.g., —C(=O)N(alkyl)$_2$, —C(=O)NH(alkyl), —alkylene-C(=O)N(alkyl)$_2$, or -alkylene-C(=O)NH(alkyl)) on the benzyl ring. The compounds of the invention can have improved cell potency (i.e., antiviral potency as determined, for example, via an assay to measure inhibition of HIV replication), particularly in the presence of human serum, relative to similar N-benzyl-8-hydroxy-1,6-naphthyridine carboxamide HIV integrase inhibitors that do not have an ortho polar substituent or have non-polar or less polar ortho substituents.

The present invention is a compound of Formula (I):

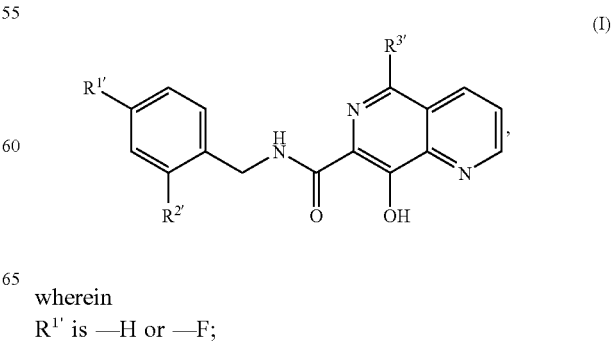

wherein $R^{1'}$ is —H or —F;

$R^{2'}$ is
(1) —$C_{1-6}$ alky-C(=O)N($R^aR^b$),
(2) —C(=O)N($R^aR^b$),
(3)

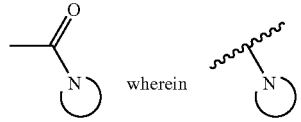

is azetidinyl, pyrrolidinyl, piperidinyl, or morpholino,
(4) triazolyl or tetrazolyl,
(5) —N($R^a$)—C($R^b$)=O,
(6)

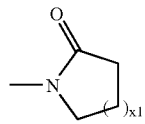

wherein x1 is an integer equal to zero, 1, or 2, or
(7) —$CO_2R^c$;

$R^{3'}$ is:
(1) —H,
(2) —C(=O)N($R^aR^b$),
(3) —$CH_2$—C(=O)N($R^aR^b$),
(4) —$CH_2CH_2$—C(=O)N($R^aR^b$),
(5) —S—$CH_2$—C(=O)N($R^aR^b$),
(6) —O—$CH_2$—C(=O)N($R^aR^b$),
(7) —N($R^a$)—C($R^b$)=O,
(8) —N($SO_2R^c$)—$CH_2$—C(=O)N($R^aR^b$),
(9) —N($R^a$)—C(=O)—C(=O)—N($R^aR^b$),
(10) —N($R^a$)$SO_2R^c$,
(11) —CH=CH—C(=O)—N($R^aR^b$),
(12) —N($R^a$)—$CH_2$—C(=O)N($R^aR^b$),
(13) —N($R^a$)—C(=O)—N($R^aR^b$),
(14) —HetC',
(15) —$(CH_2)_{1-3}$alky-HetC',
(16) —N($R^a$)—$(CH_2)_{1-3}$-HetC',
(17) —N($R^a$)—$SO_2$-N($R^aR^b$),
(18) —HetQ',
(19)

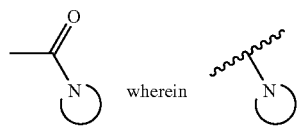

is as defined above in $R^{2'}$ (i.e., azetidinyl, pyrrolidinyl, piperidinyl, or morpholinyl), or (20)

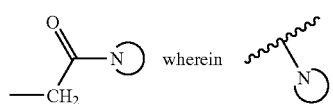

is as defined above in $R^{2'}$;

HetC' is a 5- to 7-membered saturated heterocyclic ring containing from 1 to 4 heteratoms independently selected from N, O and S, wherein the saturated heterocyclic ring is optionally substituted with from 1 to 4 substituents each of which is independently halogen, —$C_{1-4}$ alkyl, —$C_{3-6}$ cycloalkyl, —O—$C_{1-4}$ alkyl, —$C_{1-4}$ haloalkyl, —O—$C_{1-4}$ haloalkyl, —CN, oxo, phenyl, benzyl, phenylethyl, —$(CH_2)_{0-3}$C(=O)N($R^aR^b$), —$(CH_2)_{0-3}$C(=O)$R^a$, —N($R^a$)—C(=O)$R^b$, —N($R^a$)—$CO_2R^b$, —$(CH_2)_{1-3}$N($R^a$)—C(=O)$R^b$, —N($R^aR^b$), —$(CH_2)_{1-3}$N($R^aR^b$), —$SO_2R^c$, —$(CH_2)_{0-3}$C(=O)—HetD', —HetD', —N($R^a$)—HetD', and —$(CH_2)_{1-3}$—HetD'; wherein each HetD' is independently a 5- or 6-membered heteroaromatic ring containing from 1 to 4 nitrogen atoms or a 5- or 6-membered saturated heterocyclic ring containing from 1 to 4 nitrogen atoms, wherein the ring is optionally substituted with 1 or 2 substituents each of which is independently halogen, oxo, —$C_{1-4}$ alkyl, or —O—$C_{1-4}$ alkyl;

HetQ' is a 7- to 9-membered bridged azabicycloalkyl saturated ring system containing a $C_{5-7}$ azacycloalkyl ring in which two of the ring carbons are connected by a bridge containing 1 or 2 carbon atoms; wherein the bridged azabicycloalkyl ring system is optionally substituted with from 1 to 4 substituents each of which is independently halogen, oxo, or —$C_{1-4}$ alkyl;

each $R^a$ is independently —H, —$C_{1-6}$ alkyl, or —$C_{3-6}$ cycloalkyl;

each $R^b$ is independently —H, —$C_{1-6}$ alkyl, or —$C_{3-6}$ cycloalkyl; and each $R^c$ is independently a —$C_{1-6}$ alkyl or —$C_{3-6}$ cycloalkyl;

or a pharmaceutically acceptable salt thereof.

A first aspect of the present invention is a compound of Formula (I), or a pharmaceutically acceptable salt thereof, wherein $R^{2'}$ is restricted to one of groups (1) to (3); $R^{3'}$ is restricted to one of groups (1) to (17); and all other variables are as defined in the first embodiment.

A second aspect of the present invention is a compound of Formula (I),
wherein $R^{2'}$ is —$(CH_2)_{1-3}$—C(=O)N($R^aR^b$), —C(=O)N($R^aR^b$),

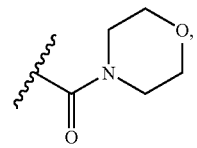

triazoly, or tetrazolyl;
and all other variables are as originally defined in the first embodiment;
or a pharmaceutically acceptable salt thereof.

A third aspect of the present invention is a compound of Formula (I), or a pharmaceutically acceptable salt thereof, wherein $R^{2'}$ is —$(CH_2)_{1-3}$—C(=O)N($R^aR^b$) or —C(=O)N($R^aR^b$); and all other variables are as defined in the first aspect of the first embodiment.

A fourth aspect of the present invention is a compound of Formula (1), wherein
$R^{2'}$ is —$(CH_2)_{1-3}$—C(=O)N($R^{a*}R^{b*}$), —C(=O)N($R^{a*}R^{b*}$),

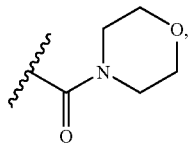

triazolyl, or tetrazolyl;

$R^{a*}$ and $R^{b*}$ are each independently —H, —$C_{1-4}$ alkyl, or cyclopropyl, with the proviso that $R^{a*}$ and $R^{b*}$ are not both —H;

each $R^a$ in $R^{3'}$ is independently —H, —$C_{1-4}$ alkyl, or cyclopropyl;

each $R^b$ in $R^{3'}$ is independently —H, —$C_{1-4}$ alkyl, or cyclopropyl; and each $R^c$ in $R^{3'}$ is independently a —$C_{1-4}$ alkyl or cyclopropyl;

and all other variables are as originally defined in the first embodiment;

or a pharmaceutically acceptable salt thereof.

In a feature of the fourth aspect of the first embodiment, one of $R^{a*}$ and $R^{b*}$ is —H, and the other of $R^{a*}$ and $R^{b*}$ is —$C_{1-4}$ alkyl or cyclopropyl; and all other variables are as defined in the fourth aspect.

A fifth aspect of the present invention is a compound of Formula (I), or a pharmaceutically acceptable salt thereof, wherein $R^{2'}$ is —$(CH_2)_{1-3}$—C(=O)N($R^{a*}R^{b*}$) or —C(=O)N($R^{a*}R^{b*}$);

$R^{a*}$ and $R^{b*}$ are each independently —H, —$C_{1-4}$ alkyl, or cyclopropyl, with the proviso that $R^{a*}$ and $R^{b*}$ are not both —H;

each $R^a$ in $R^{3'}$ is independently —H, —$C_{1-4}$ alkyl, or cyclopropyl;

each $R^b$ in $R^{3'}$ is independently —H, —$C_{1-4}$ alkyl, or cyclopropyl; and each $R^c$ in $R^{3'}$ is independently a —$C_{1-4}$ alkyl or cyclopropyl;

and all other variables are as originally defined in the first aspect of the first embodiment;

or a pharmaceutically acceptable salt thereof.

In a feature of the fifth aspect of the first embodiment, one of $R^{a*}$ and $R^{b*}$ is —H, and the other of $R^{a*}$ and $R^{b*}$ is —$C_{1-4}$ alkyl or cyclopropyl; and all other variables are as set forth in the fifth aspect.

A sixth aspect of the present invention is a compound of Formula (1), wherein

HetC' in the definition of $R^{3'}$ is a saturated heterocyclic ring selected from piperidinyl, morpholinyl, thiomorpholinyl, thiazolidinyl, isothiazolidinyl, oxazolidinyl, isooxazolidinyl, pyrrolidinyl, imidazolidinyl, piperazinyl, tetrahydrofuranyl, pyrazolidinyl, hexahydropyrimidinyl, thiazinanyl, thiazepanyl, thiadiazepanyl, dithiazepanyl, diazepanyl, and thiadiazinanyl, wherein the saturated heterocyclic ring is unsubstituted or substituted with 1 to 4 substituents each of which is independently:

(a) methyl or ethyl,
(b) =O,
(c) —C(=O)N($R^aR^b$),
(d) —$CH_2$C(=O)N($R^aR^b$),
(e) —C(=O)$R^a$, or
(f) —$SO_2R^c$;

and all other variables are as originally defined in the first embodiment;

or a pharmaceutically acceptable salt thereof.

A seventh aspect of the present invention is a compound of Formula (I), or a pharmaceutically acceptable salt thereof, wherein HetC' in the definition of $R^{3'}$ is as defined in the sixth aspect of the first embodiment; and all other variables are as defined in the first aspect of the first embodiment.

An eighth aspect of the present invention is a compound of Formula (I), wherein $R^{3'}$ is:

—H, —C(=O)N($R^aR^b$), —N($R^a$)$SO_2R^c$, —N($R^a$)—C(=O)—C(=O)—N($R^aR^b$), 1,1-dioxido-1,2-thiazinan-2-yl, 1,1-dioxidoisothiazolidin-2-yl, 1,1-dioxido-1,2,6-thiadiazinan-2-yl, 6-methyl-1,1-dioxido-1,2,6-thiadiazinan-2-yl, or 3-oxo-2-azabicyclo[2.2.1]hept-2-yl;

and all other variables are as originally defined in the first embodiment;

or a pharmaceutically acceptable salt thereof.

A ninth aspect of the present invention is a compound of Formula (I), wherein $R^{3'}$ is:

—H, —C(=O)N($R^aR^b$), —N($R^a$)$SO_2R^c$, or 1,1-dioxido-1,2-thiazinan-2-yl;

and all other variables are as originally defined in the first aspect of the first embodiment;

or a pharmaceutically acceptable salt thereof.

A tenth aspect of the present invention is a compound of Formula (1), wherein $R^{1'}$ is —H or —F;

$R^{2'}$ is —$(CH_2)_{1-3}$—C(=O)N($R^{a*}R^{b*}$), —C(=O)N($R^{a*}R^{b*}$),

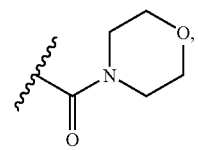

triazolyl, or tetrazolyl;

$R^{a*}$ and $R^{b*}$ are each independently —H, —$C_{1-4}$ alkyl, or cyclopropyl, with the proviso that $R^{a*}$ and $R^{b*}$ are not both —H;

$R^{3'}$ is —H, —C(=O)N($R^aR^b$), —N($R^a$)$SO_2R^c$, —N($R^a$)—C(=O)—C(=O)—N($R^aR^b$), 1,1-dioxido-1,2-thiazinan-2-yl, 1,1-dioxidoisothiazolidinyl-2-yl, 1,1-dioxido-1,2,6-thiadiazinan-2-yl; or 3-oxo-2-azabicyclo[2.2.1]hept-2-yl;

$R^a$ and $R^b$ are each independently —H, —$C_{1-4}$ alkyl, or cyclopropyl, with the proviso that $R^a$ and $R^b$ are not both —H; and $R^c$ is —$C_{1-4}$ alkyl or cyclopropyl;

or a pharmaceutically acceptable salt thereof.

An eleventh aspect of the present invention is a compound of Formula (I), wherein $R^{1'}$ is —H or —F;

$R^{2'}$ is —$(CH_2)_{1-3}$—C(=O)N($R^{a*}R^{b*}$) or —C(=O)N($R^{a*}R^{b*}$);

$R^{a*}$ and $R^{b*}$ are each independently —H, —$C_{1-4}$ alkyl, or cyclopropyl, with the proviso that $R^{a*}$ and $R^{b*}$ are not both —H;

$R^{3'}$ is —H, —C(=O)N($R^aR^b$), —NHSO$_2R^c$, —N(—$C_{1-4}$ alkyl)SO$_2R^c$, or 1,1-dioxido-1,2-thiazinan-2-yl;

$R^a$ and $R^b$ are each independently —H, —$C_{1-4}$ alkyl, or cyclopropyl, with the proviso that $R^a$ and $R^b$ are not both —H; and $R^c$ is —$C_{1-4}$ alkyl or cyclopropyl;

or a pharmaceutically acceptable salt thereof.

In a feature of either the tenth or the eleventh aspect of the first embodiment, $R^{a*}$ and $R^{b*}$ are each independently —H, methyl, ethyl, or cyclopropyl, with the proviso that $R^{a*}$ and $R^{b*}$ are not both —H; and $R^a$ and $R^b$ are each independently —H, methyl, ethyl, or cyclopropyl, with the proviso that $R^a$ and $R^b$ are not both —H; and $R^c$ is methyl, ethyl, or cyclopropyl.

A twelfth aspect of the present invention is a compound of Formula (I), wherein $R^{1'}$ is —H or —F;

$R^{2'}$ is —$(CH_2)_{1-3}$—C(=O)N($R^{a*}R^{b*}$), —C(=O)N($R^{a*}R^{b*}$),

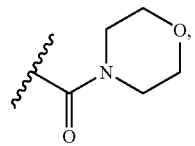

triazolyl, or tetrazolyl;

one of $R^{a*}$ and $R^{b*}$ is —H, and the other of $R^{a*}$ and $R^{b*}$ is —$C_{1-4}$ alkyl or cyclopropyl;

$R^{3'}$ is, —H, —C(=P)N($R^aR^b$), —N($R^a$)SO$_2R^c$, —N($R^a$)—C(=O)—C(=O)—N($R^aR^b$), 1,1-dioxido-1,2-thiazinan-2-yl, 1,1-dioxidoisothiazolidinyl-2-yl, 1,1-dioxido-1,2,6-thiadiazinan-2-yl; or 3-oxo-2-azabicyclo[2.2.1]hept-2-yl;

$R^a$ and $R^b$ are each independently —H, —$C_{1-4}$ alkyl, or cyclopropyl, with the proviso that $R^a$ and $R^b$ are not both —H; and $R^c$ is —$C_{1-4}$ alkyl or cyclopropyl;

or a pharmaceutically acceptable salt thereof.

A thirteenth aspect of the present invention is a compound of Formula (I), wherein $R^{1'}$ is —H or —F;

$R^{2'}$ is —$(CH_2)_{1-3}$—C(=O)N($R^{a*}R^{b*}$) or —C(=O)N($R^{a*}R^{b*}$);

one of $R^{a*}$ and $R^{b*}$ is —H, and the other of $R^{a*}$ and $R^{b*}$ is —$C_{1-4}$ alkyl or cyclopropyl;

$R^{3'}$ is —H, —C(=O)N($R^aR^b$), —NHSO$_2R^c$, —N(—$C_{1-4}$ alkyl)SO$_2R^c$, or 1,1-dioxido-1,2-thiazinan-2-yl;

$R^a$ and $R^b$ are each independently —H, —$C_{1-4}$ alkyl, or cyclopropyl, with the proviso that $R^a$ and $R^b$ are not both —H; and $R^c$ is —$C_{1-4}$ alkyl or cyclopropyl;

or a pharmaceutically acceptable salt thereof.

In a feature of either the twelfth or the thirteenth aspect, one of $R^{a*}$ and $R^{b*}$ is —H, and the other of $R^{a*}$ and $R^{b*}$ is —$C_{1-4}$ alkyl or cyclopropyl. In another feature of either the twelfth or the thirteenth aspect, one of $R^{a*}$ and $R^{b*}$ is —H, and the other of $R^{a*}$ and $R^{b*}$ is methyl, ethyl, isopropyl, or n-propyl.

A fourteenth aspect is a compound of Formula (I), or a pharmaceutically acceptable salt thereof, wherein $R^{1'}$ is —H or —F;

$R^{2'}$ is (1) —$(CH_2)_{1-3}$—C(=O)N($R^{a*}R^{b*}$), (2) —C(=O)N($R^{a*}R^{b*}$), (3) —C(=O)NH$_2$, (4)

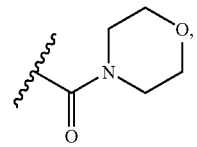

(5) triazolyl, or (6) tetrazolyl;

$R^{3'}$ is:

(1) —H, (2) —C(=O)N($R^{a''}R^{b''}$), (3) —CH$_2$—C(=O)N($R^{a''}R^{b''}$), (4) —CH$_2$CH$_2$—C(=O)N($R^{a''}R^{b''}$), (5) —N($R^a$)—C($R^b$)=O, (6) —N($R^a$)—C(=O)—C(=O)—N($R^aR^b$), (7) —N($R^a$)SO$_2R^c$, (8) —HetC', or (9) —HetQ';

HetC' is a saturated heterocyclic ring selected from thiazinanyl, isothiazolidinyl, and thiadiazinanyl, wherein the saturated heterocyclic ring is optionally substituted with from 1 to 4 substituents each of which is independently —$C_{1-4}$ alkyl or oxo;

HetQ' is azabicyclo[2.2.1]heptyl optionally substituted with 1 or 2 substituents each of which is independently oxo or —$C_{1-4}$ alkyl;

one of $R^{a*}$ and $R^{b*}$ is —H, —$C_{1-4}$ alkyl, or cyclopropyl, and the other of $R^{a*}$ and $R^{b*}$ is —$C_{1-4}$ alkyl or cyclopropyl;

each of $R^{a''}$ and $R^{b''}$ is independently —$C_{1-4}$ alkyl or cyclopropyl;

each of $R^a$ and $R^b$ is independently —H, —$C_{1-4}$ alkyl, or cyclopropyl; and $R^c$ is —$C_{1-4}$ alkyl or cyclopropyl;

or a pharmaceutically acceptable salt thereof.

A feature of the fourteenth aspect is a compound of Formula (I), or a pharmaceutically acceptable salt thereof, wherein $R^{2'}$ and $R^{3'}$ are as defined in the fourteenth aspect; one of $R^a$ and $R^b$ is —H, —$C_{1-4}$ alkyl, or cyclopropyl, and the other of $R^a$ and $R^b$ is —$C_{1-4}$ alkyl or cyclopropyl; all other variables are as defined in the fourteenth aspect; and provided that:

(i) when $R^{3'}$ is —C(=O)N($R^{a''}R^{b''}$), —CH$_2$—C(=O)N($R^{a''}R^{b''}$), or —CH$_2$CH$_2$—C(=O)N($R^{a''}R^{b''}$), then $R^{2'}$ is not —C(=O)NH$_2$; and (ii) when $R^{3'}$ is —N($R^a$)—C($R^b$)=O or —N($R^a$)—C(=O)—C(=O)—N($R^aR^b$), then $R^{2'}$ is not —C(=O)N($R^{a*}R^{b*}$) or —$(CH_2)_{1-3}$—C(=O)N($R^{a*}R^{b*}$) wherein both $R^{a*}$ and $R^{b*}$ are not H.

A fifteenth aspect of the present invention is a compound of Formula (I), or a pharmaceutically acceptable salt thereof, wherein $R^{1'}$ is —H or —F;

$R^{2'}$ is:

(1) —CH$_2$C(=O)N($R^{a*}R^{b*}$), (2) —C(=O)N($R^{a*}R^{b*}$), (3) —C(=O)NH$_2$, (4)

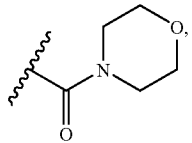

(5) triazolyl, or
(6) tetrazolyl;
R³' is:
(1) —C(=O)N(Rᵃ''Rᵇ''),
(2) —CH₂—C(=O)N(Rᵃ''Rᵇ''),
(3) —CH₂CH₂—C(=O)N(Rᵃ''Rᵇ''),
(4) —N(Rᵃ)—C(Rᵇ)=O,
(5) —N(Rᵃ)—C(=O)—C(=O)—N(RᵃRᵇ),
(6) —N(Rᵃ)SO₂Rᶜ,
(7) 1,1-dioxido-1,2-thiazinan-2-yl,
(8) 1,1-dioxidoisothiazolidin-2-yl,
(9) 1,1-dioxido-1,2,6-thiadiazinan-2-yl,
(10) 6-methyl-1,1-dioxido-1,2,6-thiadiazinan-2-yl, or
(11) 3-oxo-2-azabicyclo[2.2.1]hept-2-yl;
one Rᵃ* and Rᵇ* is —H, —C₁₋₃ alkyl, or cyclopropyl, and the other of Rᵃ* and Rᵇ* is —C₁₋₃ alkyl;
each of Rᵃ'' and Rᵇ'' is independently a —C₁₋₃ alkyl;
each of Rᵃ and Rᵇ is independently a —C₁₋₃ alkyl; and
Rᶜ is —C₁₋₃ alkyl.

A feature of the fifteenth aspect of the present invention is a compound of Formula (I), or a pharmaceutically acceptable salt thereof, wherein R²' and R³' are as defined in the fifteenth aspect; all other variables are as defined in the fifteenth aspect; and provided that:
(i) when R³' is —C(=O)N(Rᵃ''Rᵇ''), —CH₂—C(=O)N(Rᵃ''Rᵇ''), or —CH₂CH₂—C(=O)N(Rᵃ''Rᵇ''), then R²' is not —C(=O)NH₂; and
(ii) when R³' is —N(Rᵃ)—C(Rᵇ)=O or —N(Rᵃ)—C(=O)—C(=O)—N(RᵃRᵇ), then R²' is not —C(=O)N(Rᵃ*Rᵇ*) or —(CH₂)₁₋₃—C(=O)N(Rᵃ*Rᵇ*) wherein both Rᵃ* and Rᵇ* are not H.

A sixteenth aspect of the present invention is a compound of Formula (I), or a pharmaceutically acceptable salt thereof, wherein
R¹' is —H or —F;
R²' is:
(1) —CH₂C(=O)NH(CH₃),
(2) —CH₂C(=O)N(CH₃)₂,
(3) —C(=O)NH(CH₃),
(4) —C(=O)N(CH₃)₂,
(5) —C(=O)NH(CH₂CH₃),
(6) —C(=O)NH(CH₂CH₂CH₃),
(7) —C(=O)NH(CH(CH₃)₂),
(8) —CH₂C(=O)NH(cyclopropyl),
(9) —C(=O)NH₂,
(10)

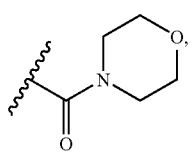

(11) triazolyl, or
(12) tetrazolyl; and
R³' is:
(1) —C(=O)N(CH₃)₂,
(2) —N(CH₃)—C(CH₃)=O,
(3) —N(CH₃)—C(=O)—C(=O)—N(CH₃)₂,
(4) —N(CH₃)SO₂CH₃,
(5) —N(CH₃)SO₂CH₂CH₃,
(6) —N(CH₂CH₃)SO₂CH₃,
(7) 1,1-dioxido-1,2-thiazinan-2-yl,
(8) 1,1-dioxidoisothiazolidin-2-yl,
(9) 6-methyl-1,1-dioxido-1,2,6-thiadiazinan-2-yl, or
(10) 3-oxo-2-azabicyclo[2.2.1]hept-2-yl;
provided that:
(i) when R³' is —C(=O)N(CH₃)₂, then R²' is not —C(=O)NH₂; and
(ii) when R³' is —N(CH₃)—C(CH₃)=O or —N(CH₃)—C(=O)—C(=O)—N(CH₃)₂, then R²' is not —C(=O)N(CH₃)₂ or —CH₂C(=O)N(CH₃)₂.

A feature of the sixteenth aspect is a compound of Formula (I), or a pharmaceutically acceptable salt thereof, wherein:
R²' is —C(=O)NH₂, —C(=O)NH(CH₃), —C(=O)N(CH₃)₂, or —C(=O)NH(CH₂CH₃); and
R³' is —N(CH₃)SO₂CH₃, —N(CH₃)SO₂CH₂CH₃, 1,1-dioxido-1,2-thiazinan-2-yl, or 6-methyl-1,1-dioxido-1,2,6-thiadiazinan-2-yl.

Additional aspects of the present invention include, but are not limited to, compounds of Formula (I) wherein each of two or three or more of R¹', R²', R³', Rᵃ, Rᵇ, Rᶜ and HetC' is independently defined in accordance with its definition in one of the aspects, or a feature thereof, as set forth above. Any and all possible combinations of these variables in Formula (I) are additional aspects of the present invention.

Another embodiment of the present invention is a compound selected from the group consisting of
N-{4-fluoro-2-[(methylamino)carbonyl]benzyl}-5-(1,1-dioxido-1,2-thiazinan-2-yl)-8-hydroxy-1,6-naphthyridine-7-carboxamide (also referred to herein as Compound A):

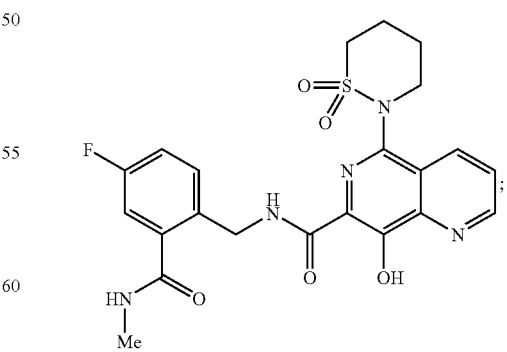

N-{2-[(dimethylamino)carbonyl]4-fluorobenzyl}-5-(1,1-dioxido-1,2-thiazinan-2-yl)-8-hydroxy-1,6-naphthyridine-7-carboxaamide:

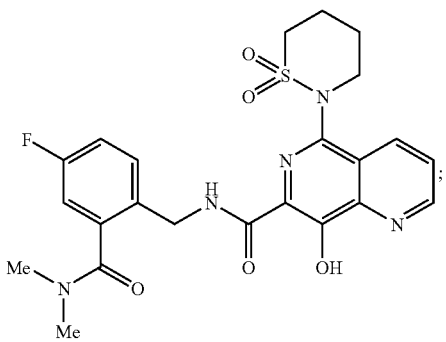

N-{2-[(dimethylamino)carbonyl]4-fluorobenzyl}-5-[methyl(methylsulfonyl)amino]-8-hydroxy-1,6-naphthyridine-7-carboxamide:

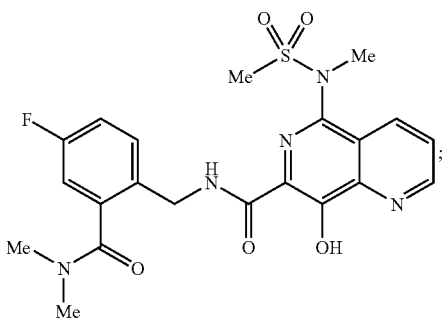

N-{4-fluoro-2-[(methylamino)carbonyl]benzyl}-5-[methyl(methylsulfonyl)amino]-8-hydroxy-1,6-naphthyridine-7-carboxamide:

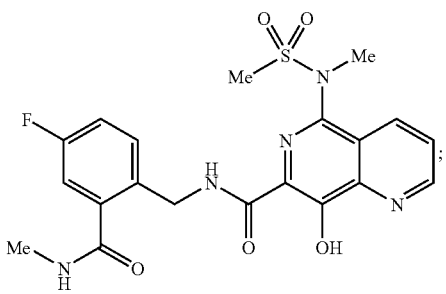

and pharmaceutically acceptable salts thereof.

An aspect of the preceding embodiment of the present invention is Compound A or a pharmaceutically acceptable salt thereof (e.g., a potassium salt or a sodium salt). Compound A has exhibited improved antiviral properties relative to the closely related N-benzyl-8-hydroxy-1,6-naphthyridine carboxamide integrase inhibitors not having an ortho polar substituent on the phenyl ring of the N-benzyl amide. These properties include improved antiviral potency in the presence of human serum proteins, and also retention of significant antiviral activity against several HIV mutants that are resistant to other integrase inhibitors.

Still another embodiment of the present invention is a compound selected from the group consisting of:

N-[2-(aminocarbonyl)-4-fluorobenzyl]-5-(1,1-dioxido-1,2-thiazinan-2-yl)-8-hydroxy-1,6-naphthyridine-7-carboxamide:

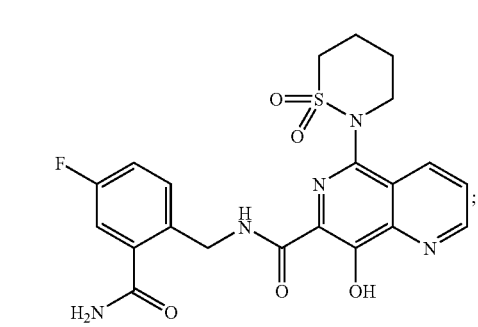

5-(1,1-dioxido-1,2-thiazinan-2-yl)-8-hydroxy-N-{2-[(methylamino)carbonyl]benzyl}-1,6-naphthyridine-7-carboxamide:

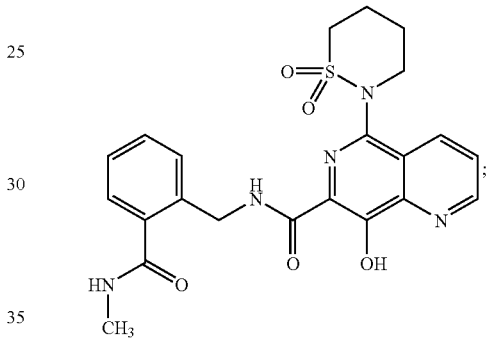

and pharmaceutically acceptable salts thereof.

Still another embodiment of the present invention is a compound selected from the group consisting of:
N-{4-fluoro-2-[(isopropylamino)carbonyl]benzyl}-5-(1,1-dioxido-1,2-thiazinan-2-yl)-8-hydroxy-1,6-naphthyridine-7-carboxamide;
N-{4-fluoro-2-[(ethylamino)carbonyl]benzyl}-5-(1,1-dioxido-1,2-thiazinan-2-yl)-8-hydroxy-1,6-naphthyridine-7-carboxamide;
N-{4-fluoro-2-[(amino)carbonyl]benzyl}-5-[methyl(methylsulfonyl)amino]-8-hydroxy-1,6-naphthyridine-7-carboxamide;
N-{4-fluoro-2-[(methylamino)carbonyl]benzyl}-5-[(ethylsulfonyl)(methyl)amino]-8-hydroxy-1,6-naphthyridine-7-carboxamide;
N-{4-fluoro-2-[(methylamino)carbonyl]benzyl}-5-(6-methyl-1,1-dioxido-1,2,6-thiadiazinan-2-yl)-8-hydroxy-1,6-naphthyridine-7-carboxamide;

and pharmaceutically acceptable salts thereof.

Other embodiments of the present invention include the following:

(a) A pharmaceutical composition comprising a therapeutically effective amount of a compound of the invention (e.g., a compound of Formula (I) or any of the specific compounds set forth above) and a pharmaceutically acceptable carrier.

(b) A pharmaceutical composition which comprises the product prepared by combining (e.g., mixing) a therapeutically effective amount of a compound of the invention and a pharmaceutically acceptable carrier.

(c) The pharmaceutical composition of (a) or (b), further comprising a therapeutically effective amount of an HIV infection/AIDS treatment agent selected from the group consisting of HIV/AIDS antiviral agents, immunomodulators, and anti-infective agents.

(d) The pharmaceutical composition of (c), wherein the HIV infection/AIDS treatment agent is an antiviral selected from the group consisting of HIV protease inhibitors, non-nucleoside HIV reverse transcriptase inhibitors, and nucleoside HIV reverse transcriptase inhibitors.

(e) A combination useful for inhibiting HIV integrase, for treating or preventing infection by HIV, or for preventing, treating or delaying the onset of AIDS, which is a therapeutically effective amount of a compound of the invention and a therapeutically effective amount of an HIV infection/AIDS treatment agent selected from the group consisting of HIV/AIDS antiviral agents, immunomodulators, and anti-infective agents.

(f) The combination of (e), wherein the HIV infection/AIDS treatment agent is an antiviral selected from the group consisting of HIV protease inhibitors, non-nucleoside HIV reverse transcriptase inhibitors and nucleoside HIV reverse transcriptase inhibitors.

(g) A method of inhibiting HIV integrase in a subject in need thereof which comprises administering to the subject a therapeutically effective amount of a compound of the invention.

(h) A method of preventing or treating infection by HIV in a subject in need thereof which comprises administering to the subject a therapeutically effective amount of a compound of the invention.

(i) The method of (h), wherein the compound of the invention is administered in combination with a therapeutically effective amount of at least one antiviral selected from the group consisting of HIV protease inhibitors, non-nucleoside HIV reverse transcriptase inhibitors, and nucleoside HIV reverse transcriptase inhibitors.

(j) A method of preventing, treating or delaying the onset of AIDS in a subject in need thereof which comprises administering to the subject a therapeutically effective amount of a compound of the invention.

(k) The method of (j), wherein the compound is administered in combination with a therapeutically effective amount of at least one antiviral selected from the group consisting of HIV protease inhibitors, non-nucleoside HIV reverse transcriptase inhibitors, and nucleoside HIV reverse transcriptase inhibitors (l) A method of inhibiting HIV integrase in a subject in need thereof which comprises administering to the subject the pharmaceutical composition of (a), (b), (c) or (d) or the combination of (e) or (f).

(m) A method of preventing or treating infection by HIV in a subject in need thereof which comprises administering to the subject the pharmaceutical composition of (a), (b), (c) or (d) or the combination of (e) or (f).

(n) A method of preventing, treating or delaying the onset of AIDS in a subject in need thereof which comprises administering to the subject the pharmaceutical composition of (a), (b), (c) or (d) or the combination of (e) or (f).

The present invention also includes a compound of the present invention (i) for use in, (ii) for use as a medicament for, or (iii) for use in the preparation of a medicament for: (a) inhibiting HIV integrase, (b) preventing or treating infection by HIV, or (c) preventing, treating or delaying the onset of AIDS. In these uses, the compounds of the present invention can optionally be employed in combination with one or more HIV/AIDS treatment agents selected from HIV/AIDS antiviral agents, anti-infective agents, and immunomodulators.

Additional embodiments of the invention include the pharmaceutical compositions, combinations and methods set forth in (a)-(n) above and the uses set forth in the preceding paragraph, wherein the compound of the present invention employed therein is a compound of one of the embodiments, or an aspect or feature or sub-feature thereof, described above. In all of these embodiments, the compound may optionally be used in the form of a pharmaceutically acceptable salt.

As used herein, the term "$C_{1-6}$ alkyl" (or "$C_1$-$C_6$ alkyl") means linear or branched chain alkyl groups having from 1 to 6 carbon atoms and includes all of the hexyl alkyl and pentyl alkyl isomers as well as n-, iso-, sec- and t-butyl, n- and isopropyl, ethyl and methyl. "$C_{1-4}$ alkyl" means n-, iso-, sec- and t-butyl, n- and isopropyl, ethyl and methyl.

The term "—$C_{1-6}$ alkyl-" refers to a $C_1$ to $C_6$ linear or branched alkyl group as just defined which is bivalent. It can alternatively be referred to as "$C_{1-6}$ alkylene" or "$C_{1-6}$ alkanediyl". A class of alkylenes of particular interest with respect to the invention is —$(CH_2)_{1-6}$—, and sub-classes of particular interest include —$(CH_2)_{1-4}$—, —$(CH_2)_{1-3}$—, —$(CH_2)_{1-2}$—, and —$CH_2$—.

The term "$C_{3-8}$ cycloalkyl" (or "$C_3$-$C_8$ cycloalkyl") means a cyclic ring of an alkane having three to eight total carbon atoms (i.e., cyclopropyl, cyclobutyl, cyclopentyl, cyclohexyl, cycloheptyl, or cyclooctyl). Similar terms such as "$C_{3-6}$ cycloalkyl" have an analogous meaning.

The term "halogen" (or "halo") refers to fluorine, chlorine bromine and iodine (alternatively referred to as fluoro, chloro, bromo, and iodo).

The term "$C_{1-6}$ haloalkyl" (which may alternatively be referred to as "$C_1$-$C_6$ haloalkyl" or "halogenated $C_1$-$C_6$ alkyl") means a $C_1$ to $C_6$ linear or branched alkyl group as defined above with one or more halogen substituents. The term "$C_{1-4}$ haloalkyl" has an analogous meaning. The term "$C_{1-6}$ fluoroalkyl" has an analogous meaning except that the halogen substituents are restricted to fluoro. A class of fluoroalkyls of particular interest with respect to the invention is the series $(CH_2)_{0-4}CF_3$ (i.e., trifluoromethyl, 2,2,2-trifluoroethyl, 3,3,3-trifluoro-n-propyl, etc.).

The term "saturated heterocyclic ring" refers to a 4- to 7-membered saturated monocyclic ring which consists of carbon atoms and one or more heteroatoms (e.g., from 1 to 4, or from 1 to 3, or from 1 to 2 heteroatoms; or 1 heteroatom) independently selected from N, O and S. Representative examples include piperidinyl, piperazinyl, azepanyl (i.e.,

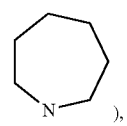

), pyrrolidinyl, pyrazolidinyl, imidazolidinyl, oxazolidinyl, isoxazolidinyl, morpholinyl (alternatively referred to as morpholino), thiomorpholinyl (or thiomorpholino), thiazolidinyl, isothiazolidinyl, tetrahydrothienyl, tetrahydrofuryl (or tetrahydrofuranyl), thiazinanyl (e.g., 1,2-thiazinanyl

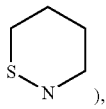

thiadiazinanyi (e.g., 1,2,6-thiadiazinanyl

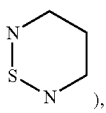

and dioxanyl.

The term "bridged azabicyclo saturated ring system" refers herein to a 7- to 9-membered bridged azabicycloalkyl saturated ring system containing a $C_{5-7}$ azacycloalkyl ring wherein two of its ring carbons are connected by a bridge containing 1 or 2 carbon atoms. The bridged azabicycloalkyl ring systems include azabicyclo[2.1.1]hexyl, azabicyclo [2.2.1]heptyl (e.g., 2azabicyclo[2.2.1]hept-2-yl), and azabicyclo[2.2.2]octyl.

The term "heteroaromatic ring" refers a 5- or 6-membered monocyclic aromatic ring which consists of carbon atoms and one or more heteroatoms (e.g., from 1 to 4, or from 1 to 3, or from 1 to 2 heteroatoms; or 1 heteroatom) independently selected from N, O and S. Representative examples of heteroaromatic rings include pyridyl, pyrrolyl, pyrazinyl, pyrimidinyl, pyridazinyl, thienyl (or thiophenyl), thiazolyl, furanyl, imidazolyl, pyrazolyl, triazolyl, tetrazolyl, oxazolyl, isooxazolyl, oxadiazolyl, thiazolyl, isothiazolyl, and thiadiazolyl.

Unless expressly stated to the contrary, all ranges cited herein are inclusive. For example, a heterocycle described as containing from "1 to 4 heteroatoms" means the heterocycle can contain 1, 2, 3 or 4 heteroatoms.

When any variable (e.g., $R^a$, $R^b$, or $R^c$) occurs more than one time in any constituent or in Formula I or in any other formula depicting and describing compounds of the invention, its definition on each occurrence is independent of its definition at every other occurrence. Also, combinations of substituents and/or variables are permissible only if such combinations result in stable compounds.

The term "substituted" (e.g., as in "aryl which is optionally substituted with from 1 to 5 substituents . . . ") includes mono- and poly-substitution by a named substituent to the extent such single and multiple substitution (including multiple substitution at the same site) is chemically allowed.

The symbol " ~~~ " in front of an open bond in the structural formula of a group marks the point of attachment of the group to the rest of the molecule.

The compounds of the present invention may have asymmetric centers and may occur, except when specifically noted, as mixtures of stereoisomers or as individual diastereomers, or enantiomers, with all isomeric forms being included in the present invention.

The compounds of the present invention are useful in the inhibition of HIV integrase, the prevention or treatment of infection by human immunodeficiency virus (HIV) and the prevention, treatment or the delay in the onset of consequent pathological conditions such as AIDS. Preventing AIDS, treating AIDS, delaying the onset of AIDS, or preventing or treating infection by HIV is defined as including, but not limited to, treatment of a wide range of states of HIV infection: AIDS, ARC (AIDS related complex), both symptomatic and asymptomatic, and actual or potential exposure to HIV. For example, the compounds of this invention are useful in treating infection by HIV after suspected past exposure to HIV by such means as blood transfusion, exchange of body fluids, bites, accidental needle stick, or exposure to patient blood during surgery.

The compounds of this invention are useful in the preparation and execution of screening assays for antiviral compounds. For example, the compounds of this invention are useful for isolating enzyme mutants, which are excellent screening tools for more powerful antiviral compounds. Furthermore, the compounds of this invention are useful in establishing or determining the binding site of other antivirals to HIV integrase, e.g., by competitive inhibition. Thus the compounds of this invention are commercial products to be sold for these purposes.

The compounds of the present invention can be administered in the form of pharmaceutically acceptable salts. The term "pharmaceutically acceptable salt" refers to a salt which possesses the effectiveness of the parent compound and which is not biologically or otherwise undesirable (e.g., is neither toxic nor otherwise deleterious to the recipient thereof). Suitable salts include acid addition salts which may, for example, be formed by mixing a solution of the compound of the present invention with a solution of a pharmaceutically acceptable acid such as hydrochloric acid, sulfuric acid, acetic acid, trifluoroacetic acid, or benzoic acid. When the compounds of the invention carry an acidic moiety, suitable pharmaceutically acceptable salts thereof can include alkali metal salts (e.g., sodium or potassium salts), alkaline earth metal salts (e.g., calcium or magnesium salts), and salts formed with suitable organic ligands such as quaternary ammonium salts. Also, in the case of an acid (—COOH) or alcohol group being present, pharmaceutically acceptable esters can be employed to modify the solubility or hydrolysis characteristics of the compound.

For the purpose of preventing or treating HIV infection or preventing, treating or delaying the onset of AIDS, the compounds of the present invention can be administered orally, parenterally (including subcutaneous injections, intravenous, intramuscular, intrasternal injection or infusion techniques), by inhalation spray, or rectally, in the form of a unit dosage of a pharmaceutical composition containing a therapeutically effective amount of the compound and conventional non-toxic pharmaceutically-acceptable carriers, adjuvants and vehicles.

The term "administration" and variants thereof (e.g., "administering" a compound) in reference to a compound of the invention mean providing the compound to the individual in need of treatment. When a compound of the invention is provided in combination with one or more other active agents (e.g., antiviral agents useful for treating HIV infection or AIDS), "administration" and its variants are each understood to include concurrent and sequential provision of the compound and other agents.

As used herein, the term "composition" is intended to encompass a product comprising the specified ingredients in the specified amounts, as well as any product which results, directly or indirectly, from combining the specified ingredients in the specified amounts.

By "pharmaceutically acceptable" is meant that the ingredients of the pharmaceutical composition must be compatible with each other and not deleterious to the recipient thereof.

The term "subject" (which may be alternatively referred to herein as "patient") as used herein refers to an animal, preferably a mammal, most preferably a human, who has been the object of treatment, observation or experiment.

The term "therapeutically effective amount" as used herein means that amount of active compound or pharmaceutical agent that elicits the biological or medicinal response in a tissue, system, animal or human that is being sought by a researcher, veterinarian, medical doctor or other clinician, which includes alleviation of the symptoms of the disease being treated. The term also includes a prophylactically effective amount suitable for prevention of the disease or condition. When the active compound (i.e., active ingredient) is administered as the salt, references to the amount of active ingredient are to the free acid or free base form of the compound.

The pharmaceutical compositions can be in the form of orally-administrable suspensions or tablets or capsules, nasal sprays, sterile injectible preparations, for example, as sterile injectible aqueous or oleagenous suspensions or suppositories. These compositions can be prepared by methods and contain excipients which are well known in the art. Suitable methods and ingredients are described in *Remington's Pharmaceutical Sciences*, 18$^{th}$ edition, edited by A. R. Gennaro, Mack Publishing Co., 1990, which is herein incorporated by reference in its entirety. In one embodiment, the pharmaceutical composition is a capsule or a tablet suitable for oral administration comprising a compound of the present invention (e.g., Compound A or a salt thereof) and a nonionic surfactant (e.g., a poloxamer).

The compounds of this invention can be administered orally in a dosage range of 0.001 to 1000 mg/kg of mammal (e.g., human) body weight per day in a single dose or in divided doses. One preferred dosage range is 0.01 to 500 mg/kg body weight per day orally in a single dose or in divided doses. Another preferred dosage range is 0.1 to 100 mg/kg body weight orally in single or divided doses. For oral administration, the compositions can be provided in the form of tablets or capsules containing 1.0 to 500 milligrams of the active ingredient, particularly 1, 5, 10, 15, 20, 25, 50, 75, 100, 150, 200, 250, 300, 400, and 500 milligrams of the active ingredient for the symptomatic adjustment of the dosage to the patient to be treated. The specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy. A suitable dosage range for oral administration of Compound A to humans is in a range of from about 25 mg to about 1000 mg per day (e.g., from about 100 mg to about 800 mg per patient once per day).

As noted above, the present invention is also directed to use of the HIV integrase inhibitor compounds of the present invention with one or more agents useful in the treatment of HIV infection or AIDS. For example, the compounds of this invention may be effectively administered, whether at periods of pre-exposure and/or post-exposure, in combination with effective amounts of one or more of the HIV/AIDS antivirals, imunomodulators, antiinfectives, or vaccines useful for treating HIV infection or AIDS. Suitable agents include the antiviral agents listed in the following Table:

| Drug Name | Manufacturer (Tradename and/or Location) | Indication (Activity) |
|---|---|---|
| abacavir GW 1592 1592U89 | Glaxo Welcome (ZIAGEN ®) | HIV infection, AIDS, ARC (nucleoside reverse transcriptase inhibitor) |
| abacavir + lamivudine + zidovudine | GlaxoSmithKline (TRIZIVIR ®) | HIV infection, AIDS, ARC (nucleoside reverse transcriptase inhibitors) |
| acemannan | Carrington Labs (Irving, TX) | ARC |
| ACH 126443 | Achillion Pharm. | HIV infections, AIDS, ARC (nucleoside reverse transcriptase inhibitor) |
| acyclovir | Burroughs Wellcome | HIV infection, AIDS, ARC, in combination with AZT |
| AD-439 | Tanox Biosystems | HIV infection, AIDS, ARC |
| AD-519 | Tanox Biosystems | HIV infection, AIDS, ARC |
| adefovir dipivoxil GS 840 | Gilead | HIV infection, AIDS, ARC (reverse transcriptase inhibitor) |
| AL-721 | Ethigen (Los Angeles, CA) | ARC, PGL, HIV positive, AIDS |
| alpha interferon | GlaxoSmithKline | Kaposi's sarcoma, HIV, in combination w/Retrovir |
| AMD3100 | AnorMed | HIV infection, AIDS, ARC (CXCR4 antagonist) |
| amprenavir 141 W94 GW 141 VX478 (Vertex) | GlaxoSmithKline (AGENERASE ®) | HIV infection, AIDS, ARC (PI) |
| ansamycin LM 427 | Adria Laboratories (Dublin, OH) Erbamont (Stamford, CT) | ARC |

-continued

| Drug Name | Manufacturer (Tradename and/or Location) | Indication (Activity) |
| --- | --- | --- |
| antibody which neutralizes pH labile alpha aberrant interferon | Advanced Biotherapy Concepts (Rockville, MD) | AIDS, ARC |
| AR177 | Aronex Pharm | HIV infection, AIDS, ARC |
| atazanavir (BMS 232632) | Bristol-Myers Squibb (ZRIVADA ®) | HIV infection, AIDS, ARC (protease inhibitor) |
| beta-fluoro-ddA | Nat'l Cancer Institute | AIDS-associated diseases |
| BMS-232623 (CGP-73547) | Bristol-Myers Squibb/ Novartis | HIV infection, AIDS, ARC (protease inhibitor) |
| BMS-234475 (CGP-61755) | Bristol-Myers Squibb/ Novartis | HIV infection, AIDS, ARC (protease inhibitor) |
| capravirine (AG-1549, S-1153) | Pfizer | HIV infection, AIDS, ARC (non-nucleoside reverse transcriptase inhibitor) |
| CI-1012 | Warner-Lambert | HIV-1 infection |
| cidofovir | Gilead Science | CMV retinitis, herpes, papillomavirus |
| curdlan sulfate | AJI Pharma USA | HIV infection |
| cytomegalovirus immune globin | MedImmune | CMV retinitis |
| cytovene ganciclovir | Syntex | sight threatening CMV peripheral CMV retinitis |
| delavirdine | Pharmacia-Upjohn (RESCRIPTOR ®) | HIV infection, AIDS, ARC (non-nucleoside reverse transcriptase inhibitor) |
| dextran Sulfate | Ueno Fine Chem. Ind. Ltd. (Osaka, Japan) | AIDS, ARC, HIV positive asymptomatic |
| ddC (zalcitabine, dideoxycytidine) | Hoffman-La Roche (HIVID ®) | HIV infection, AIDS, ARC (nuclesodie reverse transcriptase inhibitor) |
| ddI dideoxyinosine | Bristol-Myers Squibb (VIDEX ®) | HIV infection, AIDS, ARC; combination with AZT/d4T (nucleoside reverse transcriptase inhibitor) |
| DPC 681 & DPC 684 | DuPont | HIV infection, AIDS, ARC (protease inhibitors) |
| DPC 961 & DPC 083 | Bristol-Myers Squibb (from DuPont Pharma) | HIV infection AIDS, ARC (non-nucleoside reverse transcriptase inhibitors) |
| EL10 | Elan Corp, PLC (Gainesville, GA) | HIV infection |
| efavirenz (DMP 266) | Bristol-Myers Squibb (SUSTIVA ®) Merck (STOCRIN ®) | HIV infection, AIDS, ARC (non-nucleoside RT inhibitor) |
| famciclovir | Novartis (FAMVIR ®) | herpes zoster, herpes simplex |
| emtricitabine FTC | Gilead (from Triangle Pharmaceuticals) (COVIRACIL ®) Emory University | HIV infection, AIDS, ARC (nucleoside reverse transcriptase inhibitor) |
| emvirine | Gilead (from Triangle Pharmaceuticals) (COACTINON ®) | HIV infection, AIDS, ARC (non-nucleoside reverse transcriptase inhibitor) |
| enfuvirtide T-20 | Trimeris & Roche (FUZEON ®) | HIV infection, AIDS, ARC (fusion inhibitor) |
| HBY097 | Hoechst Marion Roussel | HIV infection, AIDS, ARC (non-nucleoside reverse transcriptase inhibitor) |
| hypericin | VIMRx Pharm. | HIV infection, AIDS, ARC |
| recombinant human interferon beta | Triton Biosciences (Almeda, CA) | AIDS, Kaposi's sarcoma, ARC |
| interferon alfa-n3 | Interferon Sciences | ARC, AIDS |
| indinavir | Merck (CRIXIVAN ®) | HIV infection, AIDS, ARC, asymptomatic HIV positive, also in combination with AZT/ddI/ddC |
| ISIS 2922 | ISIS Pharmaceuticals | CMV retinitis |
| JE2147/AG1776 | Agouron | HIV infection, AIDS, ARC (protease inhibitor) |
| KNI-272 | Nat'l Cancer Institute | HIV-assoc. diseases |
| lamivudine, 3TC | GlaxoSmithKline | HIV infection, AIDS, |

-continued

| Drug Name | Manufacturer (Tradename and/or Location) | Indication (Activity) |
|---|---|---|
| | (EPIVIR ®) | ARC (nucleoside reverse transcriptase inhibitor); also with AZT |
| lobucavir | Bristol-Myers Squibb | CMV infection |
| lopinavir (ABT-378) | Abbott | HIV infection, AIDS, ARC (protease inhibitor) |
| lopinavir + ritonavir (ABT-378/r) | Abbott (KALETRA ®) | HIV infection, AIDS, ARC (protease inhibitor) |
| mozenavir (DMP-450) | AVID (Camden, NJ) | HIV infection, AIDS, ARC (protease inhibitor) |
| nelfinavir | Agouron (VIRACEPT ®) | HIV infection, AIDS, ARC (protease inhibitor) |
| nevirapine | Boeheringer Ingleheim (VIRAMUNE ®) | HIV infection, AIDS, ARC (non-nucleoside reverse transcriptase inhibitor) |
| novapren | Novaferon Labs, Inc. (Akron, OH) | HIV inhibitor |
| peptide T octapeptide sequence | Peninsula Labs (Belmont, CA) | AIDS |
| PRO 140 | Progenics | HIV infection, AIDS, ARC (CCR5 co-receptor inhibitor) |
| PRO 542 | Progenics | HIV infection, AIDS, ARC (attachment inhibitor) |
| trisodium phosphonoformate | Astra Pharm. Products, Inc | CMV retinitis, HIV infection, other CMV infections |
| PNU-140690 | Pharmacia Upjohn | HIV infection, AIDS, ARC (protease inhibitor) |
| probucol | Vyrex | HIV infection, AIDS |
| RBC-CD4 | Sheffield Med. Tech (Houston TX) | HIV infection, AIDS, ARC |
| ritonavir (ABT-538) | Abbott (RITONAVIR ®) | HIV infection, AIDS, ARC (protease inhibitor) |
| saquinavir | Hoffmann-LaRoche (FORTOVASE ®) | HIV infection, AIDS, ARC (protease inhibitor) |
| stavudine; d4T didehydrodeoxy-thymidine | Bristol-Myers Squibb (ZERIT ®) | HIV infection, AIDS, ARC (nucleoside reverse transcriptase inhibitor) |
| T-1249 | Trimeris | HIV infection, AIDS, ARC (fusion inhibitor) |
| TAK-779 | Takeda | HIV infection, AIDS, ARC (injectable CCR5 receptor antagonist) |
| tenofovir | Gilead (VIREAD ®) | HIV infection, AIDS, ARC (nucleotide reverse transcriptase inhibitor) |
| tipranavir (PNU-140690) | Boehringer Ingelheim | HIV infection, AIDS, ARC (protease inhibitor) |
| TMC-120 & TMC-125 | Tibotec | HIV infections, AIDS, ARC (non-nucleoside reverse transcriptase inhibitors) |
| TMC-126 | Tibotec | HIV infection, AIDS, ARC (protease inhibitor) |
| valaciclovir | GlaxoSmithKline | genital HSV & CMV infections |
| virazole ribavirin | Viratek/ICN (Costa Mesa, CA) | asymptomatic HIV positive, LAS, ARC |
| zidovudine; AZT | GlaxoSmithKline (RETROVIR ®) | HIV infection, AIDS, ARC, Kaposi's sarcoma in combination with other therapies (nucleoside reverse transcriptase inhibitor) |

It will be understood that the scope of combinations of the compounds of this invention with HIV/AIDS antivirals, immunomodulators, anti-infectives or vaccines is not limited to the list of antivirals in the above Table, but includes in principle any combination with any pharmaceutical composition useful for the treatment of AIDS. The HIV/AIDS antivirals and other agents will typically be employed in these combinations in their conventional dosage ranges and regimens as reported in the art, including the dosages described in the *Physicians' Desk Reference*, 54$^{th}$ edition, Medical Economics Company, 2000, which is incorporated herein by reference in its entirety. The dosage ranges for a compound of the invention in these combinations are the same as those set forth above.

Abbreviations used in the instant specification, particularly the Schemes and Examples, include the following:

AIDS=acquired immunodeficiency syndrome
APCI=atmospheric pressure chemical ionization mass spectroscopy
ARC=AIDS related complex
BOC or Boc=t-butyloxycarbonyl
BOP=benzotriazol-1-yloxytris-(dimethylamino)phosphonium hexafluorophosphate
t-Bu=tert-butyl
n-BuLi=n-butyllithium
DEAD=diethylazodicarboxylate
DIPA=diisopropylamine
DMF=dimethylformamide
DMPU=1,3-dimethyl-3,4,5,6-tetrahydro-2(1H)-pyrimidinone
DMSO=dimethyl sulfoxide
dppf=1,1'-bis(diphenylp hosphino)ferrocene
EDC or EDAC=1-ethyl-3-(3-dimethylaminopropyl)carbodiimide
EDTA=ethylenediaminetetraacetic acid
ES-MS=eletron spray mass spectroscopy
Et=ethyl
EtOAc=ethyl acetate
HIV=human immunodeficiency virus
HOAT=1-hydroxy-7-azabensotriazole
HOBt=1-hydroxy benzotriazole hydrate
HPLC=high performance liquid chromatography
HRMS=high resolution mass spectroscopy.
KF=Karl Fisher titration for water
LC=liquid chromatography
Me=methyl
MeOH=methanol
Ms=mesyl or methanesulfonyl
MS=mass spectroscopy
MTBE methyl tert-butyl ether
NBS=N-bromosuccinimide
NIS=N-iodosuccinimide
NMM=N-methyl morpholine
NMR=nuclear magnetic resonance
Ph=phenyl
PMBCl=p-methoxybenzyl chloride
Pr=propyl
TEA=triethylamine
Tf$_2$O=triflic anhydride
TFA=trifluoroacetic acid
TsCl=toluenesulfonyl chloride
THF=tetrahydrofuran
TLC=thin layer chromatography
UV=ultraviolet The compounds of the present invention can be readily prepared according to the following reaction schemes and examples, or modifications thereof, using readily available starting materials, reagents and conventional synthesis procedures. In these reactions, it is also possible to make use of variants which are themselves known to those of ordinary skill in this art, but are not mentioned in greater detail. Furthermore, other methods for preparing compounds of the invention will be readily apparent to the person of ordinary skill in the art in light of the following reaction schemes and examples. Unless otherwise indicated, all variables are as defined above.

The compounds of the present invention can be prepared by the coupling of suitable 1,6-naphthyridine-7-carboxylic acids (or acid derivatives such as acid halides or esters) with the appropriate benzylamines. Scheme 1 depicts the coupling reaction to obtain compounds of Formula (I).

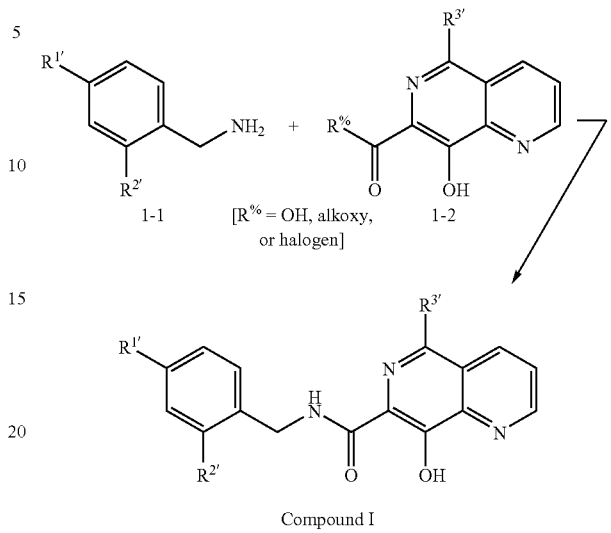

Methods for coupling carboxylic acids with amines to form carboxamides are well known in the art. Suitable methods are described, for example, in Jerry March, *Advanced Organic Chemistry*, 3rd edition, John Wiley & Sons, 1985, pp. 370-376, or in M. Bodanszky, *The Practice of Peptide Synthesis*, Springer-Verlag, 1984. Amines of formula 1-1 can be prepared, for example, by the reaction of a suitable benzyl halide with ammonia, by conversion of a suitable benzyl halide with hexamethylenetetramine, by treating the halide with potassium phthalimide and hydrolyzing the product, and by converting a benzyl halide to an azide and then reducing the azide to an amine; which methods are described, for example, in Jerry March, *Advanced Organic Chemistry*, 3$^{rd}$ edition, John Wiley & Sons, 1985, pp. 364-365, 366, 377-378, 380, and 1106. Amines of formula 1-1 can also be prepared using, for example, the methods described in Richard Larock, *Comprehensive Organic Transformations*, 2$^{nd}$ edition, Wiley-VCH Publishers Inc, 1999, pp 753-879, or routine variations thereof. Naphthyridine carboxylic acids of formula 1-2 can be prepared using methods described in Ochiai et al., *Chem. Ber.* 1937, 70: 2018, 2023; and Albert et al., *J. Chem. Soc.* 1952, 4985, 4991; or routine variations thereof. The schemes set forth below illustrate and expand upon the chemistry portrayed in Scheme 1.

Scheme 1A depicts a method for preparing benzylamine reactants having at least one ortho-aminocarbonyl group on the benzyl ring. Substituted toluene 1A-1 is functionalized on the methyl group via radical bromination to give the bromide 1A-2. Radical brominations are well known in the art and are described, for example, in J. March, *Advanced Organic Chemistry*, 3rd edition, John Wiley & Sons, 1985, p. 625. The azide 1A-3 can then be obtained by displacement of the bromide with azide (see J. March, *Advanced Organic Chemistry*, 3rd edition, John Wiley & Sons, 1985, p. 380), followed by reduction of the azide using triphenylphosphine and water to afford the amine 1A-4. Similar reductions are described in *Tetrahedron* 2000, 56(52): 10175-10184; in *J. Am. Chem. Soc.* 2001, 123(5): 875-885; and in Zhou, *Tett Lett.* 1999, 40: 2729. Following protection of the amino group on 1A-4 using BOC, the iodide can be transformed into the carboxyamide 1A-6 through a palladium-catalyzed carbonylation reaction in the presence of a suitable amine, in a manner similar to that described in G. Ortar, *Tett. Lett.* 1986, 27: 3931. Following removal of the BOC group, amine 1A-7 can be coupled to a suitable naphthyridine carboxylic acid, e.g., with EDC and HOAt in the presence of a suitable base such as triethylamine.

with triphosgene and coupled with a variety of benzylamines to provide the compounds of the invention 2-9.

The starting anhydrides of formula 2-1 can be prepared via methods described in Philips et al., *Justus Liebigs Ann. Chem.* 1895, 288: 2535; Bernthsen et al., *Chem. Ber.* 1887; 20: 1209; Bly et al., *J. Org. Chem.* 1964, 29: 2128-2135; and Krapcho et al., *J. Heterocycl. Chem.* 1993, 30: 1597-1606; or routine variations thereof.

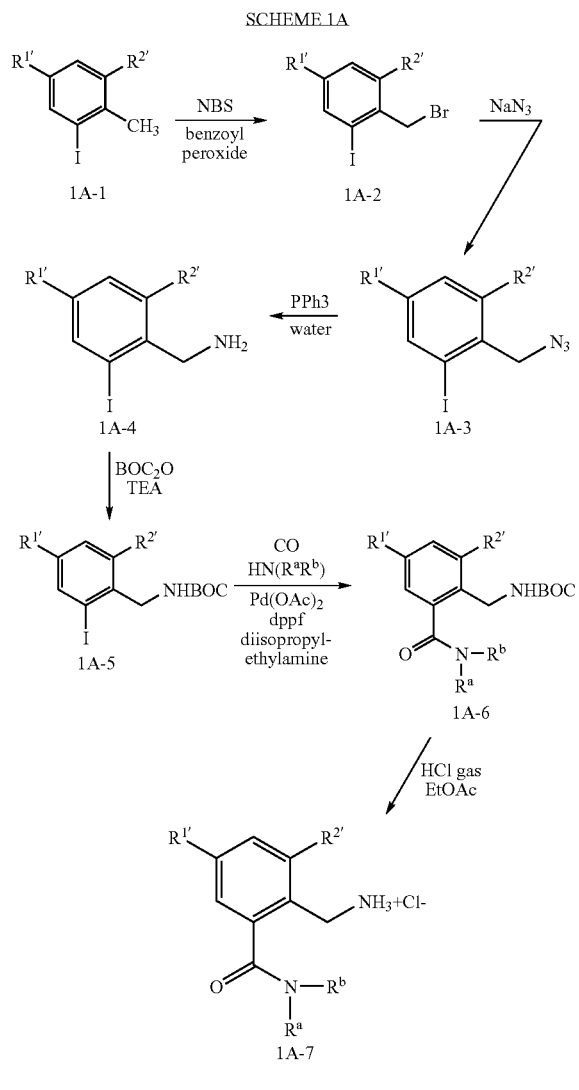

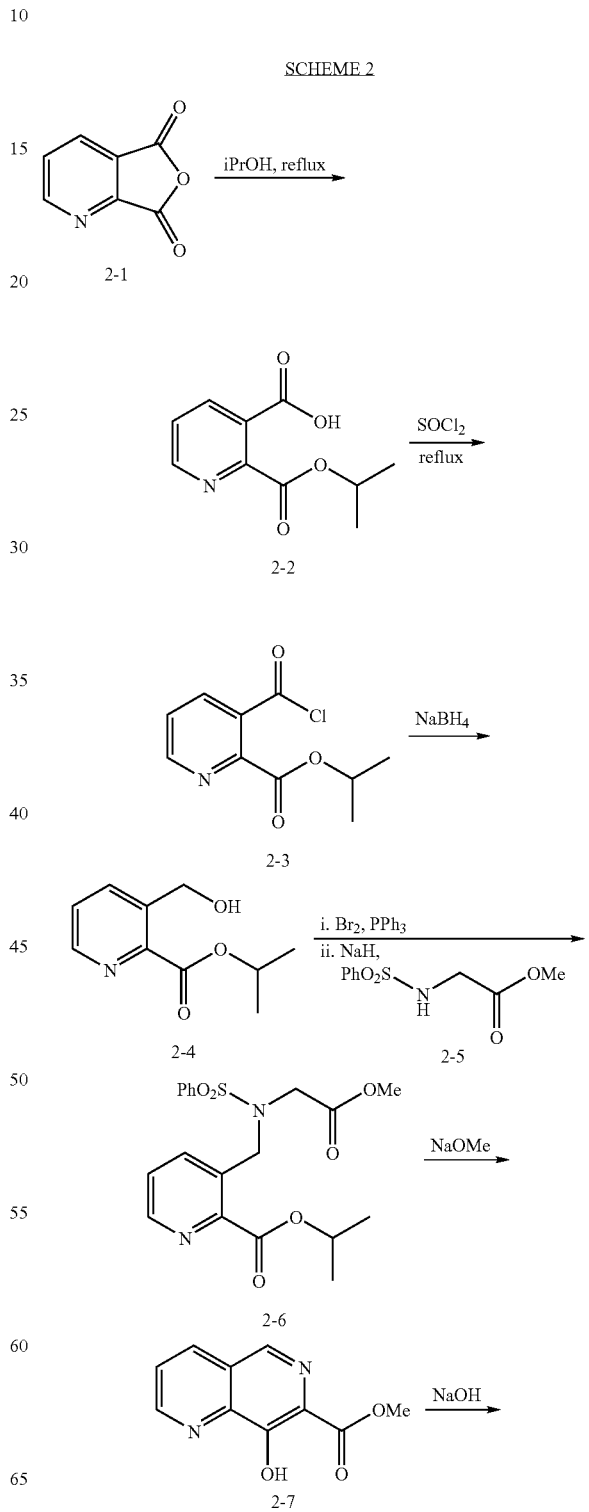

In Scheme 2, following the procedure set forth in Ornstein et al., *J. Med. Chem.* 1989, 32: 827-833, quinolinic anhydride 2-1 can be opened with isopropanol to provide mono acid 2-2, which can be converted to the corresponding acyl chloride 2-3 (e.g., by refluxing thionyl chloride). Acyl chloride 2-3 can then be reduced (e.g., with $NaBH_4$ or $LiBH_4$) to the corresponding alcohol 2-4, which can be converted to the corresponding bromide through the action of bromine in the presence of triphenylphosphine. Alkylation of the bromide with the sodium anion of phenylsulfonamide 2-5 in a polar aprotic solvent like DMP can provide sulfonamide 2-6, which can be treated with a base (e.g., alkali metal alkoxide such as sodium methoxide) to provide the bicyclic ester 2-7 via a Dieckmann cyclization. Saponification of the ester (e.g., with aqueous NaOH at reflux) will afford the acid 2-8. The acid 2-8 can be activated

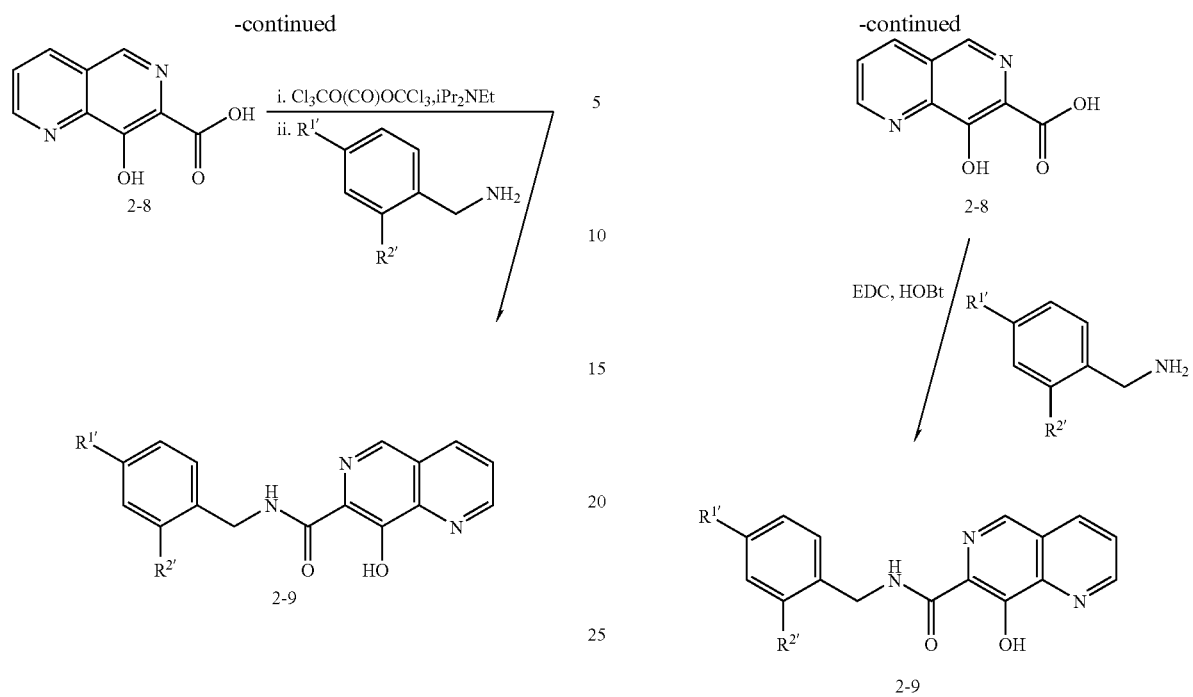

Scheme 3 depicts an alternative synthesis in which alcohol 2-4 can undergo the Mitsunobu reaction with the phenylsulfonamide of glycine methyl ester to provide 3-1. The sulfonamide 3-1 can again be elaborated to provide the acid 2-8, which can be coupled with a variety of amines using standard reagents to provide the compounds of the invention 2-9.

Scheme 3A depicts a variation of the synthesis shown in Scheme 3, wherein the acid 3A-2 is reacted with ethyl chloroformate to form the mixed anhydride 3A-3, which is reduced to alcohol 3A-4. Alcohol 3A-4 can undergo the Mitsunobu reaction with methyl tosylglycine to form the ester 3A-5, which under treatment with base cyclizes to form the 1,6-naphthyridine 3A-6. Bromination then yields the bromoester 3A-7, which can be employed to prepare compounds of the invention.

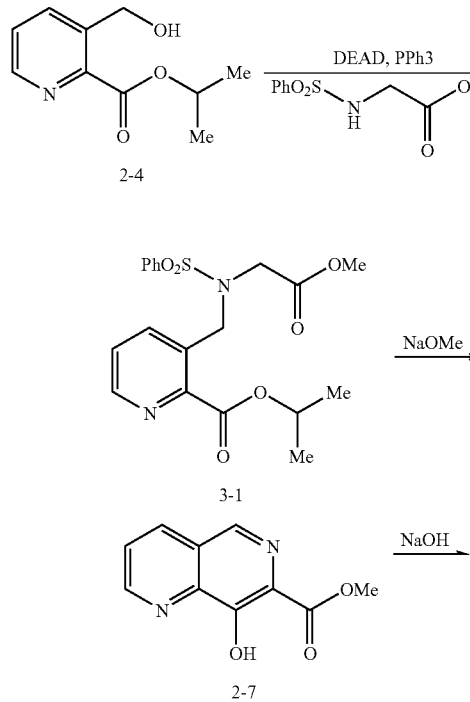

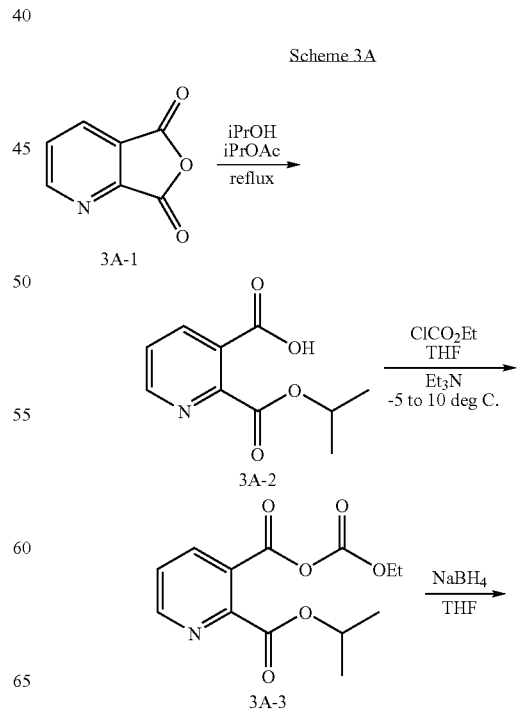

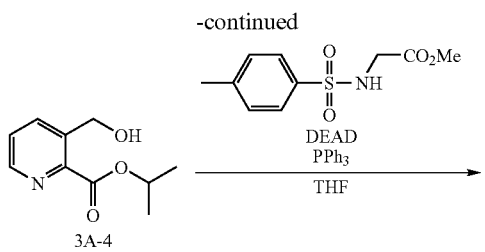
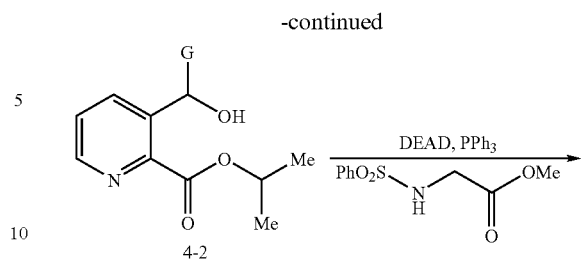
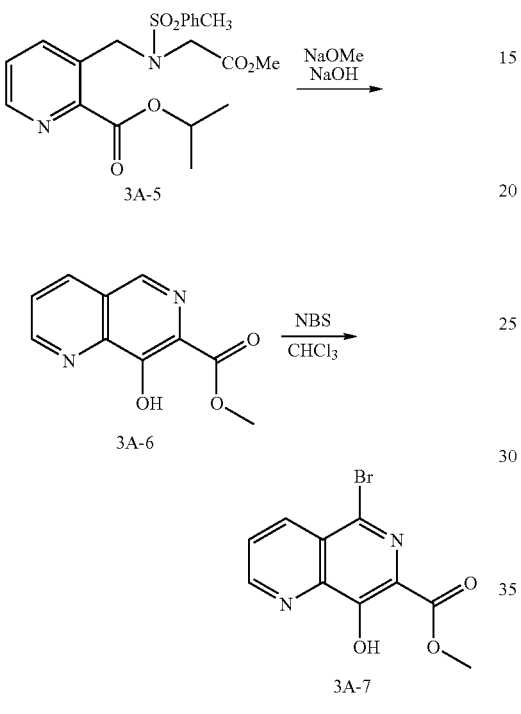
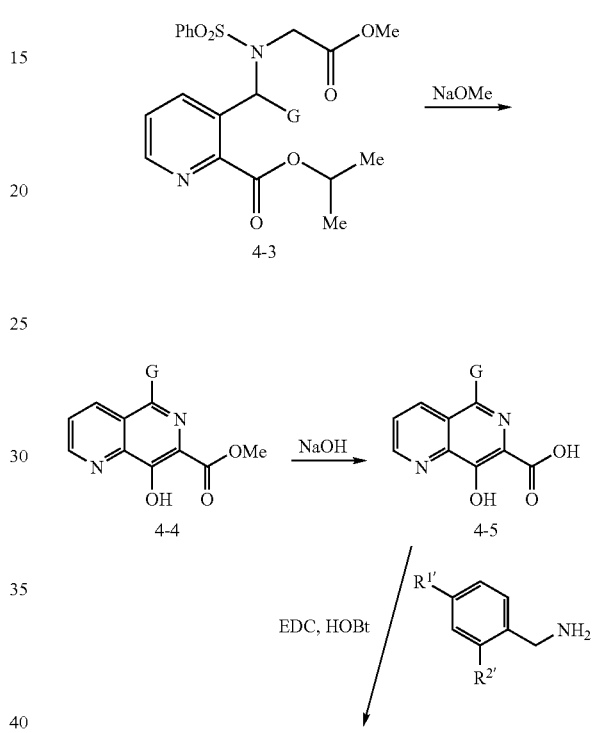

The preparation of compounds that feature additional substituents can be achieved in accordance with Scheme 4. Oxidation of the alcohol 2-4 with manganese dioxide in an inert solvent such as methylene chloride will provide aldehyde 4-1. The addition of Grignard reagents (such as phenyl magnesium bromide) to aldehyde moiety 4-1 can occur regioselectively to provide the alcohol 4-2, which can then be elaborated to the compounds of the invention 4-6.

SCHEME 4

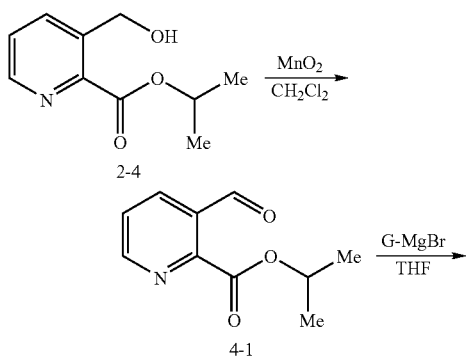

Compounds of the invention that comprise an amino substituent at the 5 position can be prepared in the manner set forth in Scheme 5. Bromination of the phenol 5-1 occurs regioselectively upon treatment with NBS in an inert solvent like methylene chloride to afford 5-2. Reaction of this bromide with an amine at elevated temperatures in the presence of a polar solvent such as DMPU affords compounds of the invention 5-3.

SCHEME 5

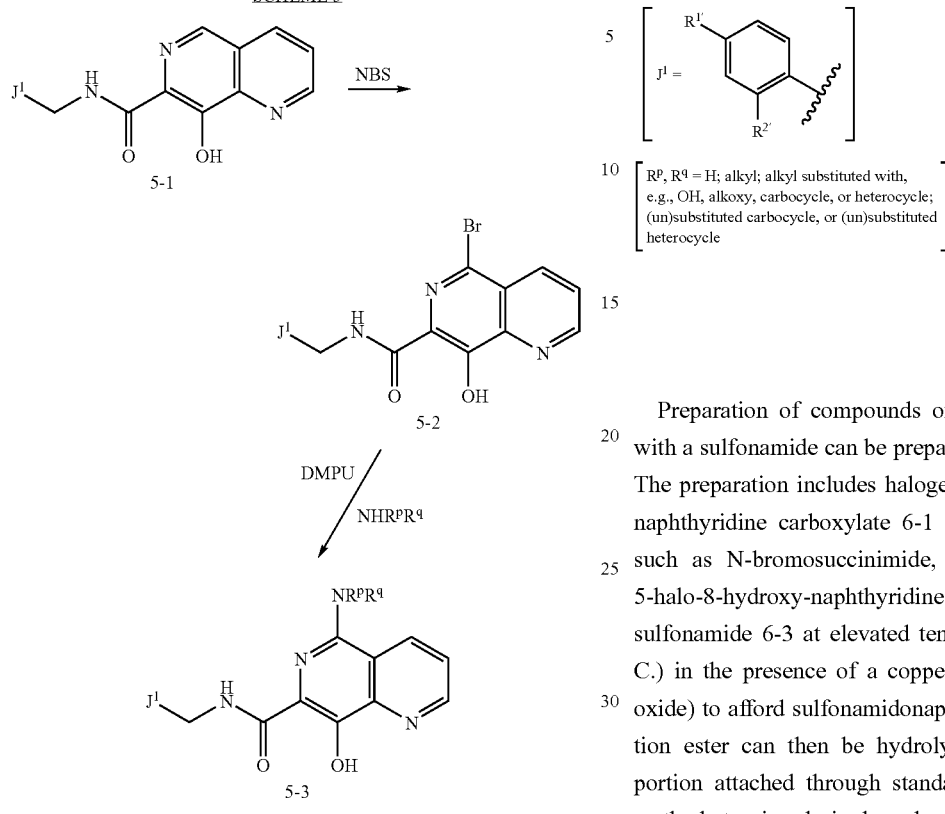

Preparation of compounds of the invention substituted with a sulfonamide can be prepared according to Scheme 6. The preparation includes halogenation of alkyl 8-hydroxy-naphthyridine carboxylate 6-1 with a halogenation agent such as N-bromosuccinimide, and then condensing the 5-halo-8-hydroxy-naphthyridine carboxylic ester 6-2 with sulfonamide 6-3 at elevated temperature (e.g., about 120° C.) in the presence of a copper promoter (e.g., copper(I) oxide) to afford sulfonamidonaphthyridine 6-4. The 7-position ester can then be hydrolyzed and the benzylamine portion attached through standard amide bond formation methods to give desired product 6-6.

SCHEME 6

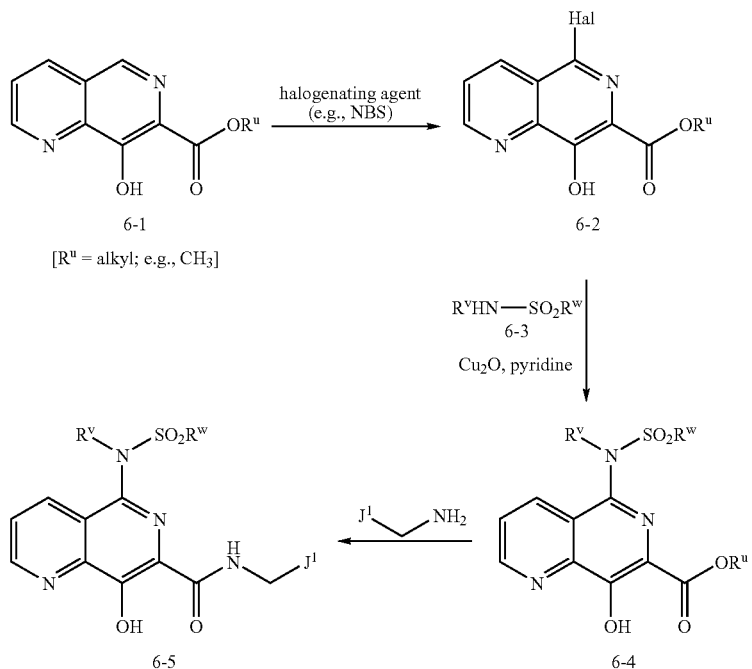

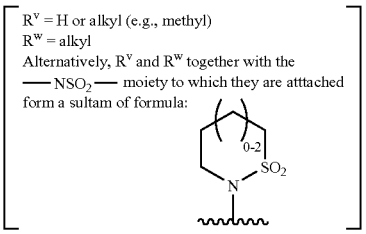

[
R$^v$ = H or alkyl (e.g., methyl)
R$^w$ = alkyl
Alternatively, R$^v$ and R$^w$ together with the
—NSO$_2$— moiety to which they are atttached
form a sultam of formula:
]

Scheme 7 shows a method for preparing compounds of the invention in which the benzylamine moiety has either an ortho-substituted amino-2-oxoethyl group or an ortho-substituted aminocarbonyl group. In this scheme, amine 7-1 is coupled with a suitable naphthyridine carboxylic acid under standard EDC/HOAt coupling conditions in the presence of a suitable base (e.g., No) to afford amide product 7-2. The resulting ester can then be hydrolyzed to the acid which can then be coupled with a suitable amine.

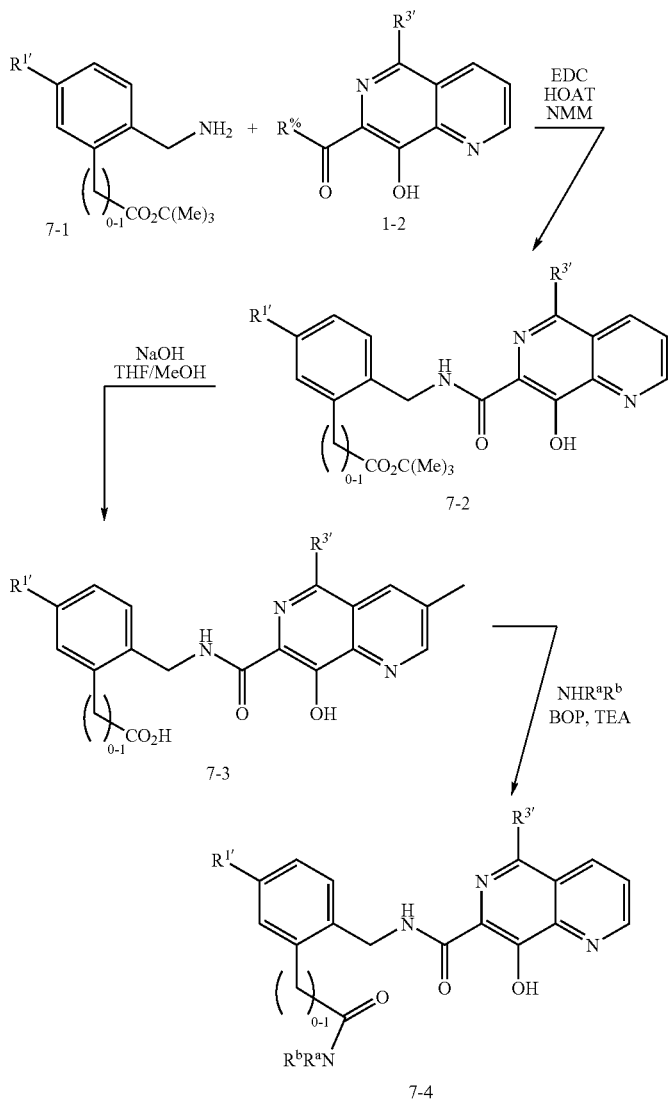

Scheme 8 describes the preparation of compounds having an aminocarboxy group at the 5-position of the naphthyridine ring. In this scheme, the brominated naphthyridine 8-1 is treated with carbon monoxide and methanol under palladium catalysis utilizing 1,1"-bis(diphenylphosphino)ferrocene as a ligand, using conditions similar to those described in Ortar, *Tett. Letters* 1986, 27 (33): 3931, to afford acylated naphthyridine 8-2. Removal of the tosyl protecting group with sodium methoxide in an alcholic solvent (e.g., trifluoroethanol) affords the dimethyl dicarboxylate 8-3, which can be selectively hydrolyzed under aqueous base conditions (e.g., as described in Jerry March, *Advanced Organic Chemistry*, 3rd edition, John Wiley & Sons, 1985, pp. 334-338) to the carboxylic acid 8-4. The amide 8-5 can then be obtained from 8-4 with conventional amide coupling reagents like BOP or EDC in the presence of excess amine. The 7-position ester can then be hydrolyzed with aqueous base to afford the acid 8-6, which can then be coupled with a suitable benzylamine to give 8-7.

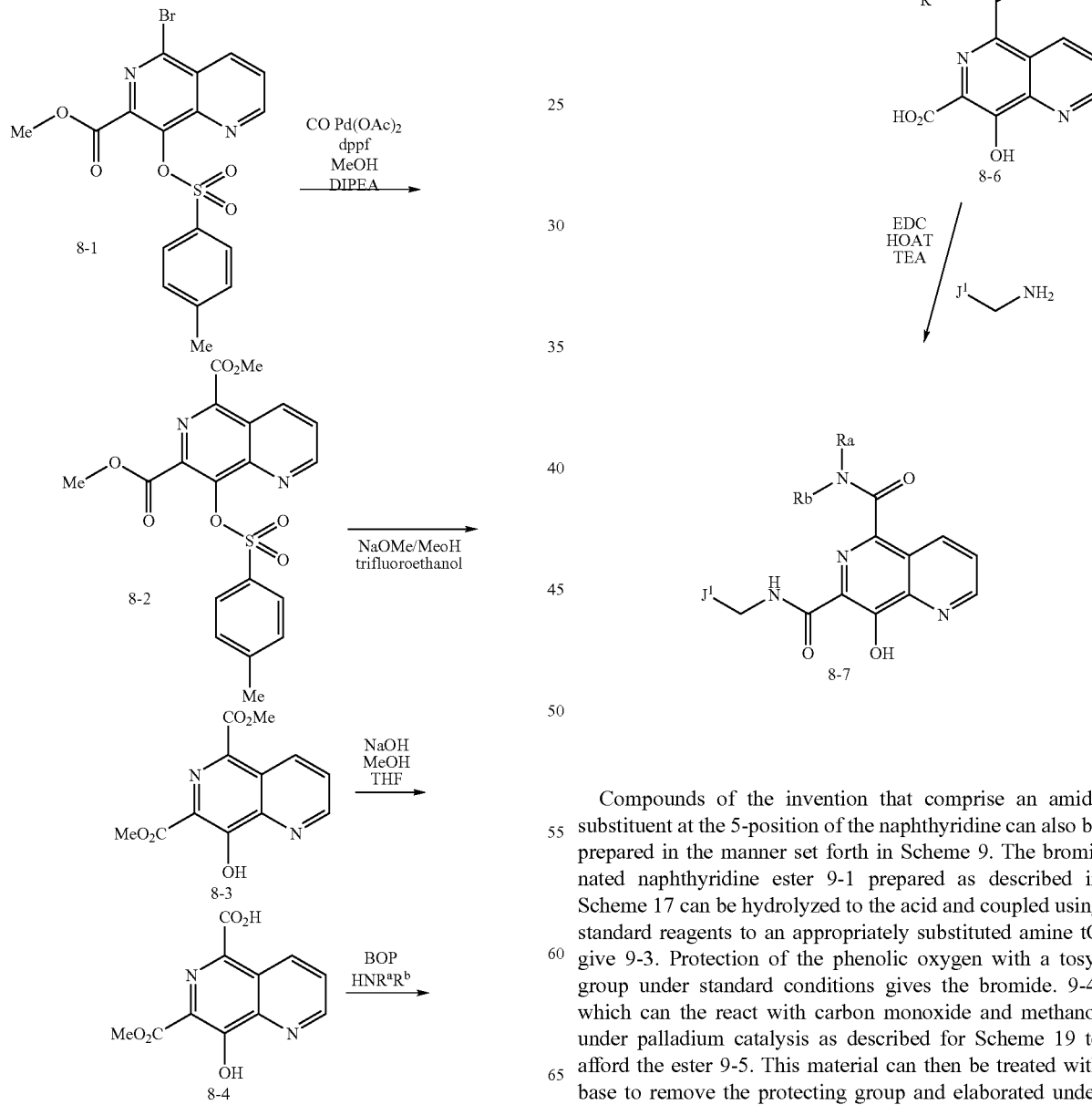

Compounds of the invention that comprise an amide substituent at the 5-position of the naphthyridine can also be prepared in the manner set forth in Scheme 9. The brominated naphthyridine ester 9-1 prepared as described in Scheme 17 can be hydrolyzed to the acid and coupled using standard reagents to an appropriately substituted amine tQ give 9-3. Protection of the phenolic oxygen with a tosyl group under standard conditions gives the bromide. 9-4, which can the react with carbon monoxide and methanol under palladium catalysis as described for Scheme 19 to afford the ester 9-5. This material can then be treated with base to remove the protecting group and elaborated under standard conditions to compounds of the invention 9-7.

SCHEME 9

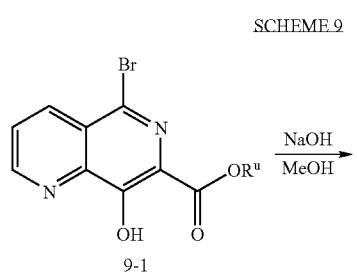
9-1

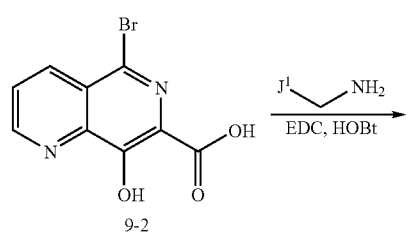
9-2

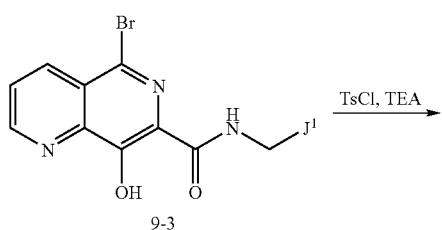
9-3

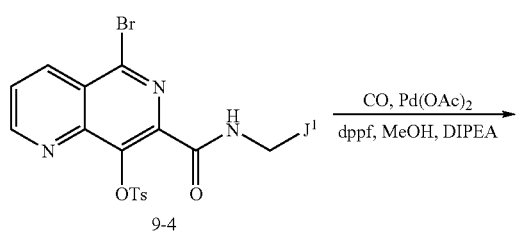
9-4

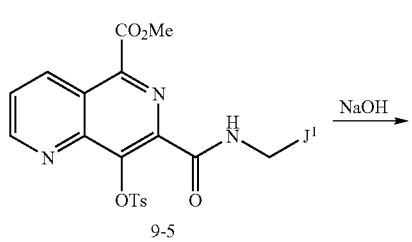
9-5

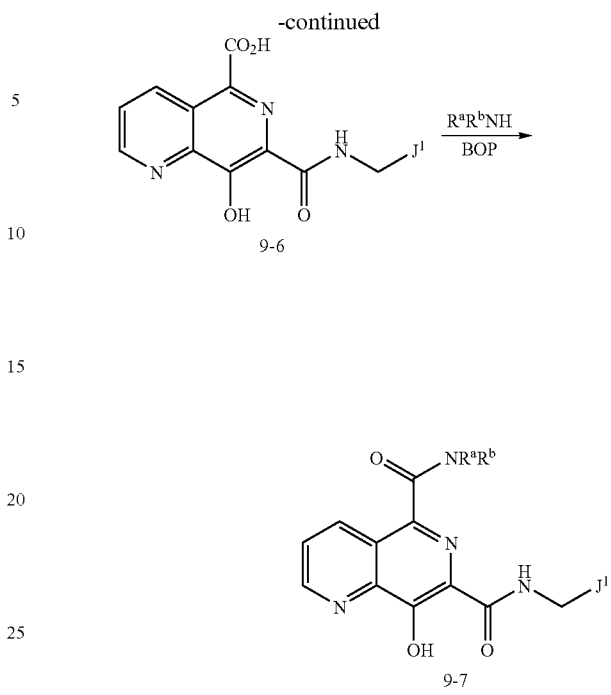

9-6

9-7

In the processes for preparing compounds and intermediates of the present invention as set forth in the foregoing schemes, functional groups in various moieties and substituents may be sensitive or reactive under the reaction conditions employed and/or in the presence of the reagents employed. Such sensitivity/reactivity can interfere with the progress of the desired reaction to reduce the yield of the desired product, or possibly even preclude its formation. Accordingly, it may be necessary or desirable to protect sensitive or reactive groups on any of the molecules concerned. Protection can be achieved by means of conventional protecting groups, such as those described in *Protective Groups in Organic Chemistry*, ed. J. F. W. McOmie, Plenum Press, 1973 and in T. W. Greene & P. G. M. Wuts, *Protective Groups in Organic Synthesis*, John Wiley & Sons, 1991. The protecting groups may be removed at a convenient subsequent stage using methods known in the art. Alternatively the interfering group can be introduced into the molecule subsequent to the reaction step of concern. For example, if either of substituents $R^{1'}$ and $R^{2'}$ in amine 1-1 can interfere with the coupling reaction between reactants 1-1 and 1-2 of Scheme 1, the substituent can be incorporated into the molecule in a post-coupling step. Scheme 7 above illustrates the post-coupling introduction of an amidecontaining substituent on the benzyl ring.

Further description of methods suitable for use (either directly or via routine modification) in preparing compounds of the present invention can be found in WO 02/30930 and in U.S. Pat. No. _____, which is published U.S. application Ser. No. 09/973,853, filed Oct. 10, 2001, the disclosure of which is incorporated herein by reference in its entirety.

The following examples serve only to illustrate the invention and its practice. The examples are not to be construed as limitations on the scope or spirit of the invention.

EXAMPLE 1

Preparation of 1,4-Butanesultam

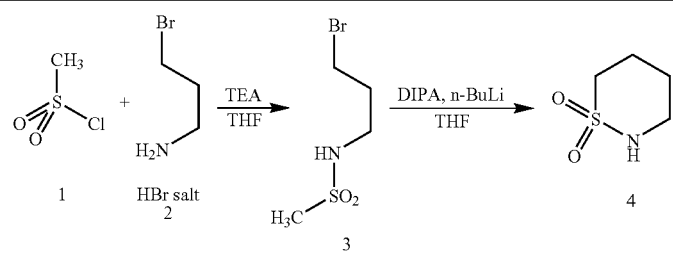

| | Weight | FW | Moles | Equiv. | Density | Volume |
|---|---|---|---|---|---|---|
| MsCl (1) | 2.36 kg | 114.55 | 20.6 | 1.03 | 1.480 | 1.59 L |
| 3-bromopropyl-amine (2) HBr salt | 4.40 kg | 220 | 20.0 | 1.00 | | |
| TEA | 4.07 kg | 101.19 | 40.2 | 2.01 | 0.726 | 5.60 L |
| THF | | | | | | 43 + 4 + 8 = 55 L |
| DIPA | 481 g | 101.19 | 4.75 | 0.25 | 0.722 | 666 mL |
| 1,10-Phenanthroline | 4.11 g | 180.21 | | | | |
| n-BuLi, 1.6M in hexane | | | | | | |

The 3-bromopropylamine-HBr salt (2) and THF (43 L) were placed in a 72 L round-bottomed-flask under $N_2$ and the resulting slurry was cooled to 0° C.

Two dropping funnels were fitted to the flask. One was charged with the TEA and the other with a solution of the MsCl (1) and THF (4 L). The contents of the addition funnels were added at roughly the same rate (the TEA was added slightly faster than the MsCl) while maintaining an internal reaction temperature below 10° C. The addition required 2 h. The resulting white suspension was warmed to 23° C. and aged for 1 h. The suspended solids (a mixture of TEA-HBr and TEA-HCl) were removed by filtration through a dry frit. The cake was washed with THF (8 L). The combined filtrate and cake-rinse, a THF solution of 3, was collected in a 100 L round-bottomed-flask under $N_2$. To the solution of 3 was added the 1,10-phenanthroline and the DIPA and the resulting solution was cooled to −30° C. The n-BuLi was added over about 4 h maintaining the internal temperature below −20° C. After 1.25 eq of the n-BuLi was added the reaction mixture became deep brown and the color remained as the addition was completed. The reaction mixture was warmed to 0° C. over 3 h. A small aliquot was removed, and partitioned between saturated $NH_4Cl$ and EtOAc. The EtOAc was evaporated and the residue examined by $^1H$ NMR to confirm consumption of 3 and conversion to 4. To the reaction mixture at 0° C. was added saturated aqueous $NH_4Cl$ (12 L, the first 1 L slowly, a heat kick to 6° C. was observed) and then brine (12 L). The phases were partitioned and the aqueous phase was extracted with EtOAc (20 L). The organic phases were combined, washed with brine (4 L) and then concentrated under vacuum to about 12 L. The solvent was switched to EtOAc (20 L used) maintaining a volume of 12 L. After the solvent switch, a yellow slurry resulted n-Heptane (20 L) was added with stirring and the slurry was cooled to 5° C. After a 1 h age the solids were collected on a frit and rinsed with cold (5° C.) 3:5 EtOAc/n-heptane. The wet cake was dried for 24 h under a stream of dry $N_2$ to provide 1.44 kg (53% from 2) of sultam 4 as a crystalline yellow solid.

EXAMPLE 2

Preparation of 5-(1,1-dioxido-1,2-thiazinan-2-yl)-8-hydroxy-1,6-naphthyridine-7-carboxylic acid methyl ester Step 1:
5-Bromo-8-hydroxy-1,6-naphthyridine-7-carboxylic acid methyl ester

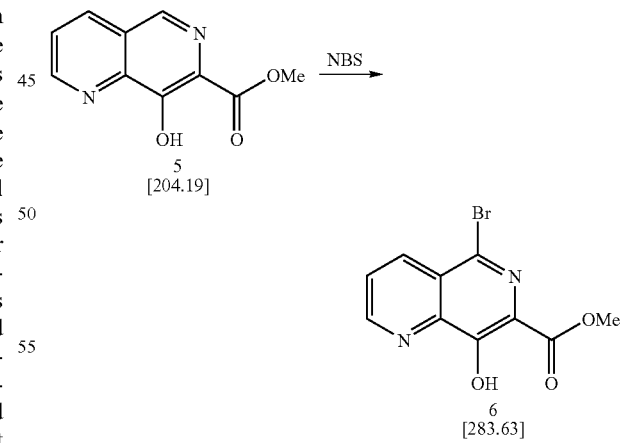

N-bromosuccinimide (7.83 g, 44.0 mmol) was added to a solution of 8-hydroxy-1,6-naphthyridine-7-carboxylic acid methyl ester (5, 8.17 g, 40.0 mmol) in chloroform (32 mL) over 20 min maintaining the temperature at 20-50° C. and the mixture was aged for 30 min at 50° C. The mixture became a thick, stirrable slurry and HPLC analysis indicated <2% starting material remaining. The mixture was cooled to 30° C. over 15 min. MeOH (64 mL) was added over 30 min then a 1:1 mixture of MeOH-water (64 mL) was added over 30 min. The mixture was cooled to −40° C. over 30 min and aged at −40° C. for 30 min. The cold mixture was filtered and the solid was washed with 1:1 MeOH:water (100 mL) at 10-20° C. The off white crystalline solid was dried under a stream of nitrogen to provide 10.48 g (93% yield) of 5-bromo-8-hydroxy-1,6-naphthyridine-7-carboxylic acid methyl ester (6).

HPLC retention times: δ=2.2 min, 6=6.0 min, HPLC conditions: 150×4.6 mm ACE 3 C18 column, isocratic elution with 30% MeCN in 0.025% aq $H_3PO_4$ at 1 mL/min, 25° C. with detection at 254 nm; HPLC retention times: 5=1.8 min, 6=3.1 min, HPLC conditions: 150×4.6 mm ACE 3 C18 column, isocratic elution with 46% MeCN in 0.025% aq $H_3PO_4$ at 1 mL/min, 25° C. with detection at 254 nm. $^{13}C$ NMR of 6 ($CDCl_3$, 100 MHz): 169.7, 156.3, 154.5, 143.9, 137.1, 132.4, 128.0, 126.1, 124.2, 53.4.

Step 2: 5-Bromo-8-(4-toluenesulfonyloxy)-1,6-naphthyridin-7-carboxylic acid methyl ester

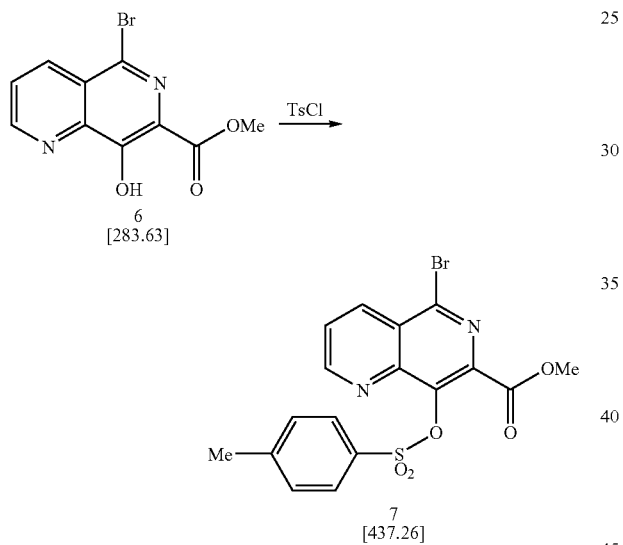

Triethylamine (0.759 g, 7.50 mmol) was added to a suspension of 5-bromo-8-hydroxy-1,6-naphthyridine-7-carboxylic acid methyl ester (6, 1.415 g, 5.000 mmol) in chloroform (5 mL) over 5 min maintaining the temperature at 20-50° C. to give a yellow suspension. p-Toluenesulfonyl chloride (1.15 g, 6.00 mmol) was added over 5 min maintaining the temperature at 20-40° C. to give a yellow solution. The mixture was aged at 40° C. for 2 h during which a crystalline solid precipitated out of the mixture and the color faded (HPLC analysis indicated <0.5% starting material remaining). The mixture was cooled to 20° C. over 15 min. MeOH (10 mL) was added over 30 min then a 1:1 mixture of MeOH:water (10 mL) was added over 30 min. The mixture was cooled to −40° C. over 30 min and aged at −40° C. for 30 min. The cold mixture was filtered and the solid was washed with 1:1 MeOH:water (10 mL), MeOH (5 mL), MTBE (10 mL) and hexanes (10 mL) all at 10-20° C. The off-white crystalline solid was dried under a stream of nitrogen to provide 2.112 g (97% yield) of 5-bromo-8-(p-toluenesulfonyloxy)-1,6-naphthyridine-7-carboxylic acid methyl ester (7).

HPLC retention times: 6=3.1 min, 7=12.4 min, HPLC conditions: 150×4.6 mm ACE 3 C18 column, isocratic elution with 46% MeCN in 0.025% aq $H_3PO_4$ at 1 mL/min, 25° C. with detection at 254 nm. $^{13}C$ NMR of 7 (d6-DMSO, 100 MHz): 163.2, 157.0, 146.5, 145.8, 141.9, 141.3, 139.2, 137.2, 132.3, 130.4, 129.0, 127.6, 127.1, 53.3, 21.7.

Step 3: 5-(1,1-Dioxido-1,2-thiazinan-2-yl)-8-(4-toluenesulfonyloxy)-1,6-naphthyridine-7-carboxylic acid methyl ester

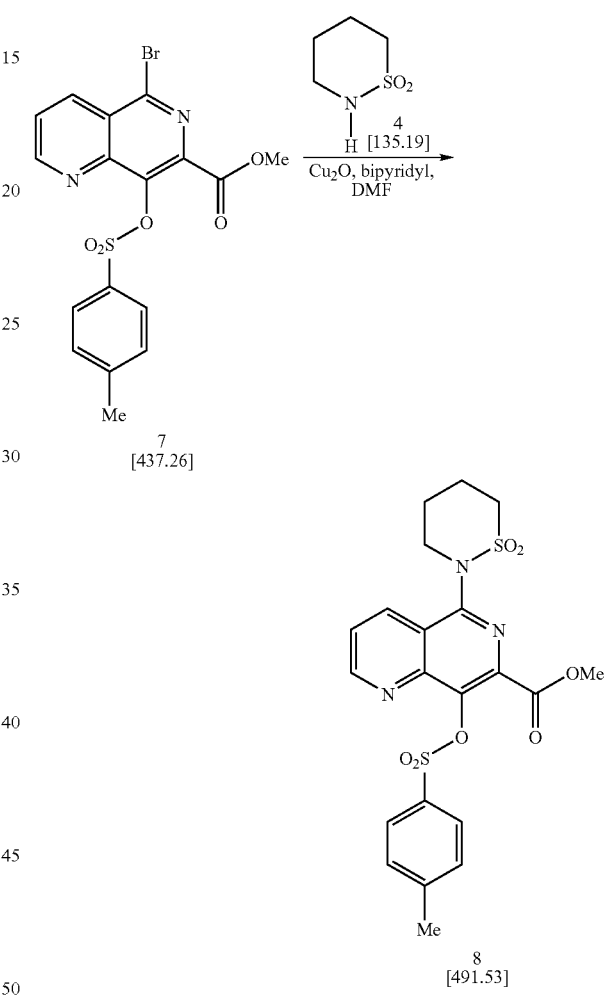

A mixture of 5-bromo-8-(p-toluenesulfonyloxy)-1,6-naphthyridine-7-carboxylic acid methyl ester (7, 2.186 g, 5.000 mmol), 1,4-butane sultam (4, 811 mg, 6.00 mmol), copper (I) oxide (858 mg, 6.00 mmol, <5 micron), 2,2'-bipyridyl (937 mg, 6.00 mmol) and DMF (10 mL) was degassed by stirring under a stream of nitrogen for 1 min and heated to 120° C. for 4 h. The brown suspension became a dark red solution with a small amount of undissolved copper (I) oxide remaining (HPLC analysis indicated <0.5% starting material remaining). The mixture was diluted with chloroform (10 mL), Solkaflok (200 mg) was added and the resulting mixture was filtered through a plug of Solkaflok. The plug was washed with chloroform (10 mL) and the combined filtrates were stirred vigorously with a solution of EDTA disodium salt dihydrate (3.8 g, 10.2 mmol) in water (40 mL) while air was slowly bubbled in for 40 min. The upper aqueous phase became turquoise while the lower organic phase became yellow. The organic phase was washed with a solution of EDTA disodium salt (1.9 g, 5.1 mmol) in water (30 mL) and a solution of sodium bisulfate monohydrate (0.87 g, 6.3 mmol) in water (30 mL). Each of the above three aqueous phases was back extracted sequentially with one portion of chloroform (15 mL). The organic phases were dried over sodium sulfate and filtered. The dried organic extracts were concentrated and solvent switched to a final volume of 15 mL MeOH using a total of 30 mL MeOH for the switch at atmospheric pressure. Product crystallized during the solvent switch. The resulting slurry was cooled to 0° C. over 30 min and aged at 0° C. for 30 min. The slurry was filtered cold and the solid was washed with MeOH (15 mL). The off white solid was dried under a stream of nitrogen to provide 1.910 g (78%) of 5-(N-1,4-butanesultam)-8-(p-toluenesulfonyloxy)-1,6-naphthyridine-7-carboxylic acid methyl ester (8).

HPLC retention times: 7=12.4 min, 8=10.3 min, DMF=1.3 min, Bipy=1.5 min, HPLC conditions: 150×4.6 mm ACE 3 C18 column, isocratic elution with 46% MeCN in 0.025% aq $H_3PO_4$ at 1 mL/min, 25° C. with detection at 254 nm. $^{13}$C NMR of 8 (CDCl$_3$, 100 ME): 164.2, 155.3, 151.9, 146.7, 145.4, 141.2, 137.8, 135.3, 133.6, 129.6, 128.9, 125.4, 124.3, 53.4, 52.9, 48.7, 24.2, 22.0, 21.7.

Step 4: 5-(1,1-Dioxido-1,2-thiazinan-2-yl)-8-hydroxy-1,6-naphthyridine-7-carboxylic acid methyl ester

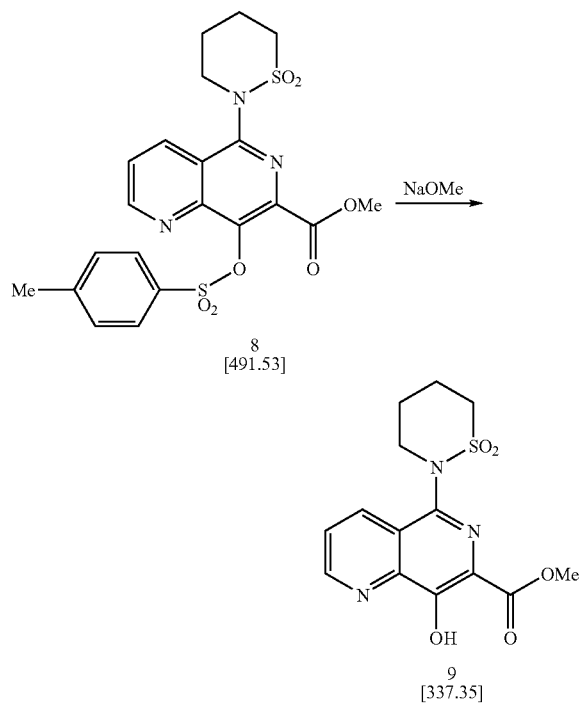

5-(N-1,4-butanesultam)-8-(p-toluenesulfonyloxy)-1,6-naphthyridine-7-carboxylic acid methyl ester (8, 1.597 g, 3.250 mmol) was dissolved in DMF (3.25 mL) at 40° C. and transferred to a solution of 0.5M NaOMe in MeOH (16.25 mL, 8.125 mmol) over ca 1-2 min at 20-25° C. The resulting yellow homogenous mixture was heated to 50° C. and aged for 5 min (HPLC analysis indicated <0.5% starting material remaining). Mixture was cooled to 25° C. over 15 min and aged at 25° C. for 15 min during which a yellow crystalline precipitate was deposited. Acetic acid (390 mg, 6.50 mmol) was added over 1 min (yellow color faded) then water (32.5 mL) was added over 15 min at 25° C. The slurry was aged for 30 min 25° C. and filtered. The filter cake was washed with 1:1 MeOH:water (32.5 nTL) and then with 1:1 MTBE:hexanes (8 mL). The filter cake was dried under a stream of nitrogen to provide 1.064 g (97%) of 5-(N-1,4-butanesultam)-8-hydroxy-1,6-naphthyridine-7-carboxylic acid methyl ester (9) as an off white crystalline solid.

HPLC retention times: 8=10.3 min, 9=2.9 min, HPLC conditions: 150×4.6 mm ACE 3 C18 column, isocratic elution with 46% MeCN in 0.025% aq $H_3PO_4$ at 1 mL/min, 25° C. with detection at 254 nm. $^{13}$C NMR of 9 (d6-DMSO, 100 MHz): 167.8, 154.4, 153.5, 143.9, 143.7, 135.2, 125.9, 125.2, 124.4, 53.2, 53.1, 49.1, 24.4, 21.9.

EXAMPLE 3

Sodium 5-(1,1-dioxido-1,2-thiazinan-2-yl)-7-[({4-fluoro-2-[(methylamino)carbonyl]-benzyl}amino)carbonyl]-1,6-naphthyridin-8-olate

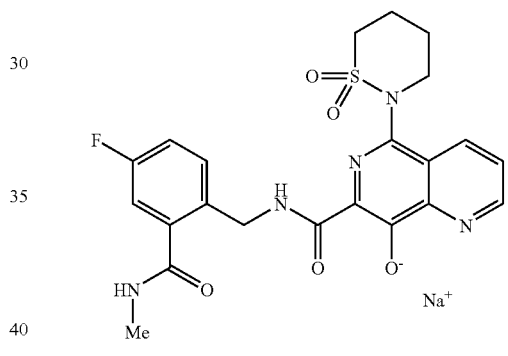

Step 1: 1-(Bromomethyl)-4-fluoro-2-iodobenzene

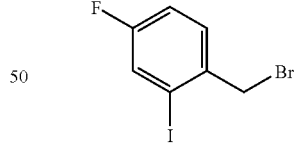

A suspension of 4-fluoro-2-iodotoluene (14.3 g, 60.6 mmol, Lancaster Synthesis), N-bromosuccinimide (16.2 g, 90.9 mmol), and benzoyl peroxide (0.74 g, 3.0 mmol) in carbon tetrachloride (500 mL) was heated to reflux for 3 days. Additional NBS (0.5 eq portions) was added as needed over this period to drive the reaction to completion. The reaction was cooled, filtered, and the filtrate was concentrated in vacuo. The residue was purified by flash column chromatography (ISCO column, 110 g silica gel) eluting with 100% hexane to afford the desired product as a white solid.

$^1$H NMR (DMSO-d$_6$, 400 MHz) δ 7.79 (1H, dt, J=8.4, 1.3 Hz), 7.68 (1H, m), 7.31 (1H, m), and 4.74 (2H, s) ppm.

Step 2: 1-(Azidomethyl)-4-fluoro-2-iodobenzene

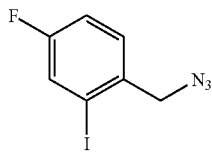

A suspension of 1-(bromomethyl)-4-fluoro-2-iodobenzene (15.68 g, 47.8 mmol) and sodium azide (4.21 g, 64.7 mmol) in dry DMF (30 mL) was heated to 50° C. for six hours. The reaction was filtered and the filtrate was concentrated in vacuo to a volume of about 10 mL. The crude was purified by flash column chromatography (ISCO column, 110 g silica gel) eluting with 100% hexane to afford the desired product as a clear oil.

$^1$H NMR (DMSO-d6, 400 MHz) δ 7.83 (1H, dd, J=8.3, 2.7 Hz), 7.54 (1H, dd, J=8.6, 6.1 Hz), 7.33 (1H, td, J=8.5, 2.6 Hz), and 4.52 (2H, s) ppm.

Step 3: 1-(4-Fluoro-2-iodophenyl)methanamine

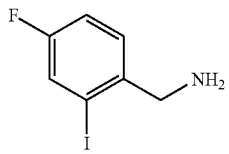

Triphenylphosphine (13.2 g, 50.4 mmol) was added to 1-(azidomethyl)-4-fluoro-2-iodobenzene (9.31 g, 33.6 mmol) dissolved in dry DMF (20 mL) at 0° C. After one hour water (3.03 mL, 168 mmol) was added and the solution was heated to 55° C. for one hour. The reaction was cooled and the solution was concentrated to about 10 mL in vacuo. The residue was purified in two runs by preparative HPLC (Gilson semi preparative HPLC system using a Waters Delta pak column (3(10×40 mm I.D.) cartridges, C18, 15 μM pore size) eluting with 95-5% water (0.025% TFA)/acetonitrile (0.025% TFA) at 45 mL/min) to give the desired product in 75% purity. Using a Waters OASIS MCX Cartridge (6 g, 35 cc syringe), half of the 75% pure product dissolved in methanol was loaded onto the column pre-equilibrated with a 1:1 solution of water and methanol. The column was washed once with the 1:1 solution and then washed several times with methanol to remove all UV active material. The amine was eluted by washing the column with methanol saturated with ammonia gas. This procedure was repeated on the remaining 75% pure product. The two batches were combined and concentrated in vacuo to give the free base of the desired product as a yellow oil.

$^1$H NMR (DMSO-d6, 400 MHz) δ 8.28 (2H, bs), 7.86 (1H, dd, J=8.2, 2.7 Hz), 7.53 (1H, dd, J=8.6, 5.9 Hz), 7.41 (1H, td, J=8.5, 2.6 Hz), and 4.09 (2H, s) ppm.

Step 4: Tert-butyl 4-fluoro-2-iodobenzylcarbamate

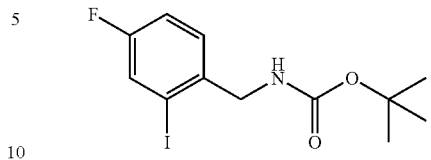

Triethylamine (1.41 mL, 10.1 mmol) was added to a 0° C. suspension of 1-(4-fluoro-2-iodophenyl)methanamine (2.30 g, 9.16 mmol) and di-tert-butyl dicarbonate (2.20 g, 10.1 mmol) in dry methylene chloride (60 mL). The homogeneous solution was stirred at 0° C. for five minutes then at room temperature for two hours. The reaction was diluted with methylene chloride (30 mL), washed with water three times and washed once with brine. The organic layer was dried over sodium sulfate, filtered, and concentrated in vacuo to a clear oil. The residue was purified by flash column chromatography (ISCO column, 110 g silica gel) eluting with a 10-25% ethyl acetate/hexane gradient over 30 minutes to afford the desired product as a clear oil.

$^1$H NMR (CDCl$_3$, 400 MHz) δ 7.55 (1H, dd, J=8.0, 2.5 Hz), 7.34 (1H, t, J=7.1 Hz), 7.05 (1H, td, J=8.3, 2.4 Hz), 5.02 (1H, m) 4.31 (2H, d, J=6.0 Hz) and 1.46 (9H, s) ppm. ES HRMS: calc'd for $C_{12}H_{15}FINO_2$+Na 374.0024, observed 374.0022.

Step 5: Tert-butyl 4-fluoro-2-[(methylamino)carbonyl]benzylcarbamate

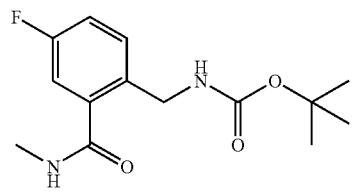

Through a solution of tert-butyl 4-fluoro-2-iodobenzylcarbamate (1.00 g, 2.85 mmol) in dry DMF (20 mL), in an oven dried glass insert in a high pressure bomb reactor flushed with nitrogen, was bubbled methylamine gas at 0° C. until the solution was saturated and excess methylamine was condensed into the reaction (approximately 30 equivalents of methylamine). Diisopropylethylamine (0.99 mL, 5.70 mmol), palladium acetate (64 mg, 0.29 mmol) and 1,1'-bis (diphenylphosphino)ferrocene (158 mg, -0.29 mmol) were added to the saturated solution. The glass insert was then placed in the pressure vessel and the vessel was purged once with carbon monoxide gas. The vessel was recharged with carbon monoxide gas to pressure of 300 psi, placed into an oil bath, and heated to 90° C. for four hours. The vessel was cooled, the gas was released slowly and the resulting mixture was partitioned between water and ethyl acetate. The layers were separated and the organic extracts were dried over sodium sulfate, filtered, and concentrated in vacuo to a brown liquid. The residue was purified by flash column chromatography (ISCO column, 110 g silica gel) eluting with a 10-50% acetone/hexane gradient over 35 minutes to afford the desired product as a brown crystalline solid.

$^1$H NMR (DMSO-d6, 400 MH) δ 8.38 (1H, d, J=4.0 Hz), 7.35-7.19 (4H, m), 4.20 (2H, d, J=6.1 Hz), 2.75 (3H, d, J=4.6 Hz) and 1.39 (9H, s) ppm.

Step 6: {4-Fluoro-2-[(methylamino)carbonyl]phenyl}methanaminium chloride

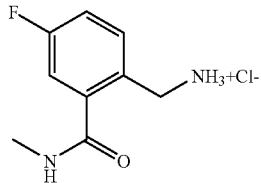

Hydrogen chloride gas was bubbled through a −78° C. solution of tert-butyl 4-fluoro-2-[(methylamino)carbonyl]benzylcarbamate (615 mg, 2.18 mmol) in ethyl acetate (20 mL) until the solution was saturated. The flask was then allowed to warm to room temperature. The reaction was concentrated in vacuo to a volume of about 5 mL and the flask was capped and placed in the freezer overnight. In the morning, the solids that had precipitated were collected by vacuum filtration and washed with cold ethyl acetate to give the desired product as an off-white solid.

$^1$H NMR (DMSO-d6, 400 MHz) δ 8.81 (1H, d, J=4.0 Hz), 8.25 (3H, bs), 7.62 (1H, dd, J 8.3, 5.7 Hz), 7.50-7.42 (2H, m), 4.04 (2H, s), and 2.80 (3H, d, J=3.7 Hz) ppm.

Step 7: 5-(1,1-Dioxido-1,2-thiazinan-2-yl)-8-hydroxy-1,6-naphthyridine-7-carboxylic acid

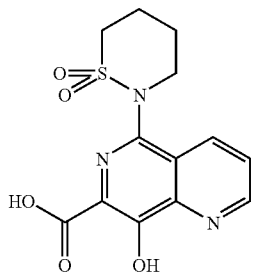

A suspension of methyl 5-(1,1-dioxido-1,2-thiazinan-2-yl)-8-hydroxy-1,6-naphthyridine-7-carboxylate (1.00 g, 2.96 mmol, prepared as described in Example 2 above) in methanol (18 mL) with aqueous lithium hydroxide (17.8 mL, 17.8 mmol, 1N solution) was stirred overnight at 60° C. The suspension was acidified to a pH=4 using 3N HCl (about 6 mL) and the resulting solution was allowed to stir overnight at room temperature. In the morning, the solids that had precipitated out of solution were collected by vacuum filtration to give the desired product as a light yellow solid.

$^1$H NMR (DMSO-d6, 400 MHz) δ 9.21 (1H, dd, J=4.3, 1.6 Hz), 8.62 (1H, dd, J=8.5, 1.6 Hz), 7.92 (1H, dd, J=8.5, 4.3 Hz), 3.91-3.78 (2H, m), 3.55-3.45 (2H, m), 2.28 (3H, m) and 1.64 (1H, m) ppm.

Step 8: 5-(1,1-Dioxido-1,2-thiazinan-2-yl)-N-{4-fluoro-2-[(methylamino)carbonyl]benzyl}-8-hydroxy-1,6-naphthyridine-7-carboxamide

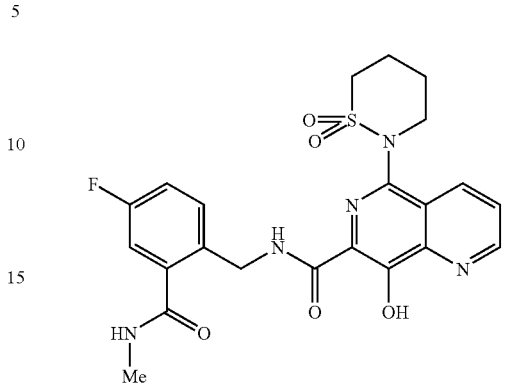

A solution of 5-(1,1-dioxido-1,2-thiazinan-2-yl)-8-hydroxy-1,6-naphthyridine-7-carboxylic acid (100 mg, 0.31 mmol), 1-[3-(dimethylamino)propyl]-3-ethylcarbodiimide hydrochloride (89 mg, 0.46 mmol), 1-hydroxy-7-azabenzotriazole (63 mg, 0.46 mmol), {4-fluoro-2-[(methylamino)carbonyl]phenyl}-methanaminium chloride (101 mg, 0.46 mmol) and triethylamine (65 µL, 0.46 mmol) in dry DMF (2 mL) was stirred at room temperature overnight. In the morning, a couple drops of water were added and the reaction was filtered through a glass fiber filter. The filtrated was purified by preparative HPLC (Gilson semi preparative HPLC system using a Waters Nova pak column (10×40 mm I.D. cartridges, C18, 6 µM pore size) eluting with 95-5% water (0.025% TFA)/acetonitrile (0.025% TFA) at 35 mL/min) to give the product as a TFA salt. The crude solid was dissolved in CHCl$_3$ and washed with aqueous saturated ammonium chloride solution. The aqueous layer was back-extracted with CHCl$_3$ three times and the combined organic extracts were dried over sodium sulfate, filtered, and concentrated in vacuo to give the desired product as a pale yellow solid.

$^1$H NMR (DMSO-d6, 400 MHz) δ 9.53 (1H, s), 9.19 (1H, s), 8.68 (1H, s), 8.58 (1H, d, J=8.0 Hz), 7.89 (1H, d, J=3.8 Hz), 7.53 (1H, m), 7.41-7.34 (2H, m), 4.64 (2H, d, J=5.7 Hz), 3.92-3.47 (4H, m), 2.83 (3H, d, J=3.8 Hz), 2.35 (3H, m), and 1.64 (1H, m) ppm.

The title compound of Step 8 was also obtained as follows:

A solution of 5-(1,1-dioxido-1,2-thiazinan-2-yl)-8-hydroxy-1,6-naphthyridine-7-carboxylic acid (1.00 g, 3.09 mmol), 1-[3-(dimethylamino)propyl]-3-ethylcarbodiimide hydrochloride (0.77 g, 4.02 mmol), and 1-hydroxy-7-azabenzotriazole (0.55 g, 4.02 mmol) in degassed dry DMF (20 mL) was aged for 30 minutes to preform the activated ester. Triethylamine (0.47 mL, 3.40 mmol) and {4-fluoro-2-[(methylamino)carbonyl]phenyl}-methanaminium chloride (0.74 g, 3.40 mmol) were added and the reaction stirred for 30 minutes. The reaction was poured into water, the pH was adjusted to 10 using 1N NaOH, and resulting solution was extracted several times with CHCl$_3$. The combined organic extracts were dried over Na$_2$SO$_4$', filtered, and concentrated to dryness in vacuo. The residue was partitioned between basic water (pH=10 using 1N NaOH) and ether. The layers were separated and the aqueous layer was extracted twice more with ether. The aqueous layer was then acidified to pH=4 using 1N HCl and extracted several times with CHCl$_3$. The combined organic extracts were dried over Na$_2$SO$_4$, filtered, and concentrated to a brown oil. Methanol was added to the flask and the flask was sonicated for 5 minutes. Solids crashed out of the solution upon sonication and were collected by vacuum filtration to afford the title compound as a whitish solid.

¹H NMR (DMSO-d6, 400 MHz) δ 9.53 (1H, s), 9.19 (1H, s), 8.68 (1H, s), 8.58 (1H, d, J=8.0 Hz), 7.89 (1H, d, J=3.8 Hz), 7.53 (1H, m), 7.41-7.34 (2H, m), 4.64 (2H, d, J=5.7 Hz), 3.92-3.47 (4H, m), 2.83 (3H, d, J=3.8 Hz), 2.35 (3H, m), and 1.64 (1H, m) ppm.

Step 9: Sodium 5-(1,1-dioxido-1,2-thiazinan-2-yl)-7-[({4-fluoro-2-[(methylamino)carbonyl]benzyl}amino)carbonyl]-1,6-naphthyridin-8-olate Sodium hydroxide (150 µL, 0.15 mmol, 1N solution) was added to a cloudy solution of 5-(1,1-dioxido-1,2-thiazinan-2-yl)-N-{4-fluoro-2-[(methylamino)carbonyl]benzyl}-8-hydroxy-1,6-naphthyridine-7-carboxamide (73 mg, 0.15 mmol) in a 2 mL mixture of acetone, acetonitrile and water. The homogeneous bright yellow solution was allowed to stir at room temperature for 30 minutes. The solvent was removed in vacuo and dried overnight on the high vac with gentle heating to give the desired product as a bright yellow solid.

¹H NMR (DMSO-d₆, 400 MHz) δ 12.12 (1H, s), 8.78 (1H, m), 8.66 (1H, d, J=4.6 Hz), 8.29 (1H, d, J=6.8 Hz), 7.56 (1H, dd, J=8.4, 4.2 Hz), 7.46 (1H, dd, J=8.3, 5.6 Hz), 7.26-7.19 (2H, m), 4.61 (2H, d, J=5.9 Hz), 3.81 (2H, m), 3.51 (1H, m), 3.23 (1H, m), 2.81 (3H, d, J=4.4 Hz), 2.43 (1H, m), 2.23 (2H, m) and 1.64 (1H, m) ppm. ES HRMS: calc'd for $C_{22}H_{21}FN_5NaO_5S$ 510.1218, observed 510.1219.

EXAMPLE 3A

Preparation of {4-Fluoro-2-[(methylamino)carbonyl]phenyl}methanaminium chloride

Step 1: Methyl 2-(bromomethyl)-5-fluorobenzoate

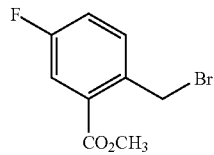

With no precautions to maintain a dry atmosphere, methyl 5-fluoro-2-methylbenzoate (Maybridge, 5 g, 29.7 mmole) was dissolved in CCl₄ (50 mL). N-bromosuccinimide (5.82 g, 32.7 mmol) and benzoyl peroxide (0.36 g, 1.48 mmole) were added and the reaction brought to reflux overnight. An additional 0.3 eq of NBS and 0.01 eq of benzoyl peroxide was added and the reaction refluxed for 4 hrs, then cooled, filtered and concentrated. The residue was chromatographed on silica eluting with a gradient of 0-10% EtOAc/Hexanes. The fractions were collected to give the product, which was a mixture of mono and bis-brominated materials, as a clear oil.

¹H NMR (CDCl₃, 400 MHz, major product peaks) δ 7.67 (1H, dd, J=2.8, 9 Hz), 7.45 (1H, dd, J=5.4, 9 Hz), 7.20 (1H, m), 4.93 (2H, s), 3.95 (3H, s) ppm.

Step 2: Methyl 2-{[bis(tert-butoxycarbonyl)amino]methyl}-5-fluorobenzoate

In a dry flask under nitrogen, di-tert-butyl iminodicarboxylate (Aldrich, 3.86 g, 17.8 mmol) was dissolved in dry DMF (5 mL) and treated with NaH (60% dispersion in oil, 0.71 g, 17.8 mmol). After the evolution of gas had ceased, Methyl 2-(bromomethyl)-5-fluorobenzoate (4 g, 16.2 mmole) dissolved in DMF (5 mL) was added. An additional 5 mL of DMF was added to aid stirring. The reaction was stirred for 2 hrs, then partitioned between water and EtOAc. The organic layer was dried with Na₂SO₄, filtered and concentrated and the residue was purified on silica eluting first with toluene, then with a gradient of 0-5% MeOH (CHCl3. The impure product thus obtained was re-chromatographed on silica eluting with a gradient of 0-30% EtOAc/Hexanes. The product was obtained as a clear oil.

¹H NMR (EMSO, 400 MHz, major product peaks) δ 7.63 (1H, dd, J=2.8, 9.4 Hz), 7.52 (1H, m), 7.20 (1H, dd, J=5.3, 8.7 Hz), 4.98 (2H, s), 3.86 (3H, s), 1.38 (s, 18H) ppm.

Step 3: Preparation of tert-butyl 4-fluoro-2-[(methylamino)-carbonyl]benzylcarbamate

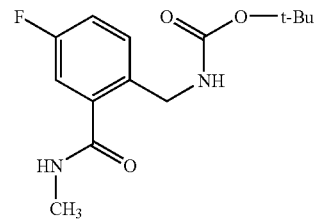

A solution of methyl 2-{[bis(tert-butoxycarbonyl)amino]methyl}-5-fluorobenzoate (5.0 g, 13.04 mmol) in toluene (40 mL) was treated with methylamine gas at −78° C. until the solution was saturated. The reaction contents were then placed into a steel bomb and heated to 70° C. overnight. After cooling, the reaction was concentrated and then the solids were triturated with ether. The resulting solids were collected by vacuum filtration. As a result of the relatively harsh reaction conditions one of the t-butyloxycarbonyl protecting groups was removed from the molecule.

¹H NMR (CDCl₃, 400 MHz) δ 7.41 (1H, dd, J=5.6, 8.3 Hz), 7.14-7.06 (2H, m), 6.64 (1H, BS), 5.69 (1H, BS), 4.26 (2H, d, J=6.3 Hz), 2.98 (3H, d, J=4.8 Hz), 1.41 (9H, s) ppm.

Step 4: Preparation of {4-fluoro-2-[(methylamino)carbonyl]phenyl}-methanaminium chloride

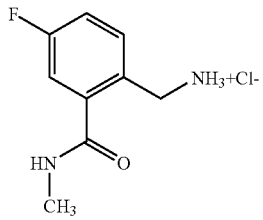

A solution of tert-butyl 4-fluoro-2-[(methylamino)carbonyl]-benzylcarbamate (2.59 g, 9.17 mmol) in EtOAc (75 mL) was cooled to −78° C. After cooling solids precipitated out of the solution. HCl gas was added to the suspension until it reached saturation at which time the reaction became homogenous. After adding the HCl gas the dry ice bath was replaced with an ice water bath and the reaction was stirred for 10 minutes at 0° C. The solution was concentrated slowly and then redissolved in EtOAc and this was repeated two more times. The resulting solids were then triturated from EtOAc and fluffy white solids were collected by vacuum filtration.

$^1$H NMR (DMSO, 400 MHz) δ 8.82 (1H, d, J=4.2 Hz), 8.34 (3H, bs), 7.64 (1H, dd, J=5.6, 8.5 Hz), 7.49-7.41 (2H, m), 4.04 (2H, s), 2.80 (3H, d, J=4.5 Hz) ppm.

EXAMPLE 3B

Alternative Preparation of {4-Fluoro-2-[(methylamino)carbonyl]phenyl}-methanaminium chloride Step 1: Di(tert-butyl) 4-fluoro-2-iodobenzylimidodicarbonate

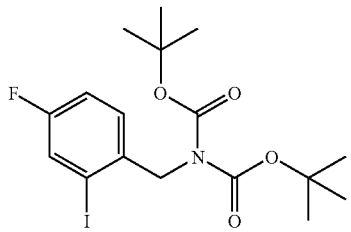

A solution of 1-(bromomethyl)-4-fluoro-2-iodobenzene (Example 3, step 1) (5 g, 15.9 mmol) in dry DMF (50 mL) under argon was cooled to 2° C. and treated with NaH (60% dispersion in oil, 0.4 g, 17.5 mmol) and stirred for 5 minutes to give a fine slurry. A solution of di-tert-butyl iminodicarboxylate (Aldrich, 3.8 g, 17.5 mmol) in 20 ml dry DMF was added dropwise, keeping the temperature between 2 and 7° C. After stirring for 1 hr at 0° C., the solution was allowed to warm to room temperature and stirred overnight. The reaction was poured into bicarbonate solution and water was added until all the solids dissolved. The solution wag extracted with ether and the combined organic layers were dried over Na$_2$SO$_4$, filtered and evaporated and the crude product was purified on 120 g silica gel ISCO cartridge eluting first with a gradient of 0-5% EtOAc/Hexanes followed by a gradient of 5-10% EtOAc/Hexanes to give the product as a clear oil that solidified to a white solid.

$^1$H NMR (CDCl$_3$, 400 MHz) δ 7.55 (1H, bd, J=7.3 Hz), 7.03 (2H, m), 4.72 (s, 2H), 1.44 (18H, s).

Step 2: Di(tert-butyl) 4-fluoro-2-[(methylamino)carbonyl]benzyl-imidodicarbonate

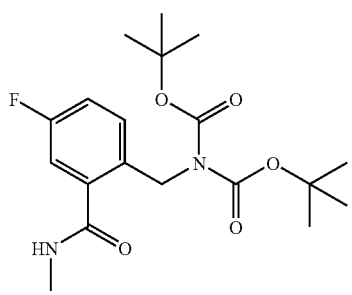

The glass reaction vessel from a Parr high pressure apparatus was briefly dried in an oven and di(tert-butyl) 4-fluoro-2-iodobenzylimidodicarbonate (5.17 g, 11.5 mmol) was added and dissolved with stirring in 25 mL of dry DMF. Argon was bubbled through the solution while it was cooled to 0° C. Palladium acetate (0.064 g, 0.29 mmol), DPPF (0.16 g, 0.29 mmol), and diisopropylethylamine (3 g, 23 mmol) were added, the flask was tared, and the solution was saturated with methylamine gas (10.5 g methylamine, 338.6 mmol). The water condensed on the outside of the reaction vessel was wiped off and the vessel was placed in the Parr high pressure apparatus which was flushed with carbon monoxide gas, then sealed and pressurized to 75 psi carbon monoxide and heated to 70° C. internal temperature for 4 hrs. The vessel was cooled and vented and the green solution was poured into water and extracted with ether. The combined ether layers were dried with Na2SO4, filtered and evaporated and the residue was chromatographed on a 120 g ISCO silica gel cartridge eluting with a gradient of 25-30% EtOAc/Hexanes to give the product as a mixture of mono and bis-tert-butylimidocarbonate protected material that was taken onto the next step. A small portion of the mono- and bis tert-butylimidocarbonate protected products were obtained pure and gave the following NMR.

$^1$H NMR (CDCl$_3$, 400 MHz) mono-protected product δ 7.42 (1H, dd, J=5.6, 8.4 Hz), 7.1 (2H, m), 6.47 (1H, bs), 5.7 (1H, bs), 4.27 (2H, d, J=6.4 Hz), 3.0 (3H, d, J=4.9 Hz), 1.40 (9H, s) ppm.

$^1$H NMR (DMSO-d6, 400 MHz) bis-protected product δ 8.4 (1H, d, J=4.3 Hz), 7.35-7.2 (2H, m), 7.11 (1H, dd, 3=5.5, 8.3 Hz), 4.81 (2H, s), 2.75 (3H, d, J=4.5 Hz), 1.38 (18H, s).

Step 3: {4-fluoro-2-[(methylamino)carbonyl]phenyl)methanaminium chloride

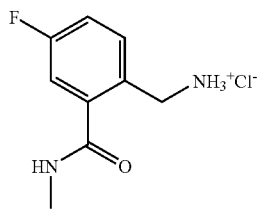

A mixture of mono and bis-protected intermediate from the previous step (4.58 g, ~19 mmol) was dissolved in 200 mL EtOAc and cooled to −60° C. under argon. The solution was saturated with HCl gas then the flask was transferred to an ice bath and the reaction monitored by HPLC until no starting materials remained. The reaction vessel was placed on a rotoevaporator and the solvent removed carefully under vacuum, first with the flask out of the water bath, then with the flask in room temperature water bath, to give a white solid. This material was resuspended in EtOAc and the solvent removed again under vacuum. The residue was dried under high vacuum overnight, then suspended in ether and filtered to give the final product as a white solid.

$^1$H NMR DMSO-d6, 400 MHz) δ 8.8 (1H, bs), 8.22 (3H, bs), 7.61 (1H, dd, J=5.6, 8.4 Hz), 7.45 (2H, m), 4.04 (2H, s), 2.80 (3H, d, J=4.5 Hz) ppm.

EXAMPLE 3C

Potassium 5-(1,1-dioxido-1,2-thiazinan-2-yl)-7-[({4-fluoro-2-[(methylamino)-carbonyl]benzyl}amino)carbonyl]-1,6-naphthyridin-8-olate Step 1: Methyl 2-bromo-5-fluorobenzoate

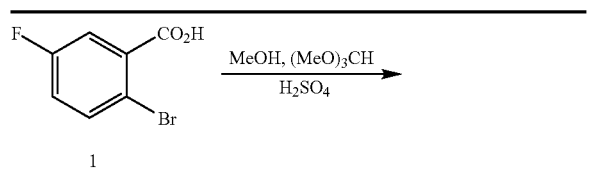

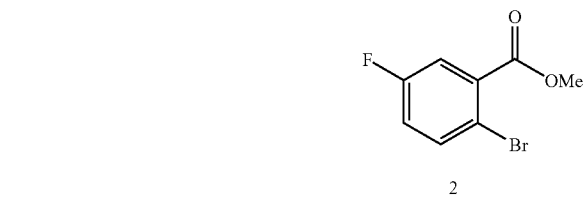

| Material | MW | Amount | Moles |
|---|---|---|---|
| 2-bromo-5-fluorobenzoic acid | 219.01 | 4.00 kg | 18.3 |
| methanol | 32.04 (d = 0.791) | 18 L | 296.3 |
| trimethylorthoformate | 106.12 | 3.88 kg | 36.5 |
| 96% sulfuric acid | 98.08 | 0.373 kg | 3.65 |
| 2M K$_2$HPO$_4$ | 174.18 | 4.82 L | 9.68 |
| ethyl acetate | | 16 L | |
| 10% NaHCO$_3$ | 84.02 | 4 L | |
| 25% brine | | 4 L | |
| toluene | | 12 L | |
| DMF | | | |

To a 72 L round bottom flask, equipped with an overhead stirrer, thermocouple, water-cooled condenser, and nitrogen inlet, was charged methanol (18 L). 2-Bromo-5-fluorobenzoic acid (4.00 kg), trimethyl orthoformate (3.876 kg), were then charged with stirring, followed by the addition 96% sulfuric acid (0.373 kg). The resulting solution was refluxed at 63° C. and aged for 10-16 hr, while the by-product (methyl formate) was removed during the reaction. The reaction mixture was monitored by HPLC. The reaction mixture was concentrated, then diluted with ethyl acetate (16 L), and cooled to 20° C. 2 M potassium hydrogen phosphate (4.82 L) was then added to adjust the pH to 6.5-7.

The mixture was then transferred to a 100 L nalgene extractor. After phase cut, the organic layer was washed with 10% NaHCO$_3$ (4 L), 25% brine (4 L), and then concentrated under reduced pressure. The residual oil was dissolved in toluene (6 L), and concentrated. This operation was done one more time. The remaining oil was dissolved in DMF (total vol. 9.2 L). The resulting solution was used for next step.

HPLC conditions: column: Zorbax, Rx C8 250×4.6 mm; temperature: 30° C.; detection: 210 nm; mobile phase: 0.1% aq H$_3$PO$_4$ (A)/MeCN (B); gradient: 90:10 (A)/(B) to 10:90 over 15 min, 10:90 hold for 5 min, 10:90 to 90:10 (A)/(B) over 10 seconds; flow rate: 1 mL/min; retention time for the desired monoester; 13.6 min.

Evaporation of a sample to dryness gave a colorless oil: $^1$H NMR (400 MHz, CDCl$_3$) δ: 7.64 (dd, J=8.8, 5.0 Hz, 1H), 7.53 (dd, J=8.8, 3.1 Hz, 1H), 7.08 (td, J=8.8, 3.1 Hz, 1H), 3.95 (s, 3H); $^{13}$C NMR (100 MHz, CDCl$_3$) δ: 165.4, 161.3 (d, J=240 Hz), 135.9, 133.4, 120.0 (d, J=20.0 Hz), 118.5 (d, J=20.0 Hz), 116.1, 52.7.

Step 2: Methyl 2-nitrile-5-fluorobenzoate

| Material | MW | Amount | Moles |
|---|---|---|---|
| methyl 2-bromo-5-fluorobenzoate | 233.03 | | 18.3 in DMF |
| copper(I) cyanide | 89.56 | 1.60 kg | 17.9 |
| DMF | | 5 L + 4 L | |
| ethyl acetate | | 35 L + 17 L | |
| 10% NH$_4$OH-20% NH$_4$Cl | | 37 L | |
| 25% brine | | 8 L | |
| MeOH | | 33 L | |

To a solution of methyl 2-bromo-5-fluorobenzoate (18.26 moles) in DMF (total vol. 9.2 L) was charged copper(I) cyanide (1.603 kg) in DMF (5 L) slurry and followed with a DMF flush (4 L). After being degassed, the reaction mixture was heated at 100° C. for 10-16 hours. The reaction mixture was monitored by HPLC. After being cooled to 50° C.-60° C., ethyl acetate (20 L) was added, and then 10% NH$_4$OH-20% NH4Cl (22 L). The mixture was then transferred to a 100 L nalgene extractor. The 72 L round bottom flask was washed with 15 L of EtOAc and 15 L of water and transferred to the 100 L extractor. After phase cut, the aqueous layer was back-extraction with EtOAc (17 L) for one time. The combined organic layers were washed with 10% NH$_4$OH/20% NH$_4$Cl: water (1:1, 3×10 L), 16% brine (8 L), concentrated, and solvent switched to MeOH (total vol. 22 L, KF=152.6 μg/mL). The resulting solution was used for next step.

HPLC conditions: column: Zorbax, Rx C8 250×4.6 mm; temperature: 30° C.; detection at 210 nm; mobile phase: 0.1% aq H$_3$PO$_4$ (A)/MeCN (B); gradient: 90:10 (A)/(B) to 10:90 over 15 min, 10:90 hold for 5 min, 10:90 to 90:10 (A)/(B) over 10 seconds; flow rate: 1 mL/min; retention time for the desired monoester 11.7 min.

Evaporation of a sample to dryness gave a light yellow solid: $^1$H NMR (CDCl$_3$) δ: 7.86-7.80 (m, 2H), 7.37 (td, J=8.5, 2.6H, 1H), 4.02 (s, 3H); $^{13}$C NMR (100 MHz, CDCl$_3$) δ: 164.3 (d, J=260 Hz), 163.3, 137.1 (d, J=10.0 Hz), 135.2 (d, J=10.0 HZ), 120.2 (d, J=30.0 Hz), 118.8 (d, J=20.0 Hz), 116.6, 109.0, 53.1.

Step 3: Methyl 2-aminomethyl-5-fluorobenzoate, HCl salt

| Material | MW | Amount | Moles |
|---|---|---|---|
| methyl 2-nitrile-5-fluorobenzoate | 179.15 | | 10.6 in MeOH |
| 3.0M HCl in MeOH (anhydrous) | 36.46 | 7.10 L | 21.22 |
| 10% Pd/C | | 0.475 kg | |
| solka floc | | 2.6 kg | |
| MeOH | | 3 × 10 L | |

A degassed mixture of methyl 2-nitrile-5-fluorobenzoate (10.6 moles) in MeOH (total 10.0 L), 3.0 M HCl in MeOH (7.10 L), and 10% Pd/C (0.475 kg) was submitted to hydrogenation at 40° C. and 45 PSI for 48 hours. The reaction mixture was monitored by HPLC. After being cooled to ambient temperature, the reaction mixture was then filtered by passing a short Solka Flock (2.6 kg), which was washed with MeOH (3×10 L). The combined filtrates were concentrated and solvent-switched to toluene in total volume (about 18 L, KF=154 μg/mL). The crystalline solid was filtered off and washed with toluene, dried under vacuum with nitrogen sweep to afford the title compound (>99A % purity, HPLC).

HPLC conditions: column: Zorbax, Rx C8 250×4.6 mm; temperature: 30° C.; detection at 210 nm; mobile phase: 0.1% aq H$_3$PO$_4$ (A)/MeCN (B); gradient: 90:10 (A)/(B) to 10:90 over 15 min, 10:90 hold for 5 min, 10:90 to 90:10 (A)/(B) over 10 seconds; flow rate: 1 mL/min; retention time for the desired monoester: 5.78 min. $^1$H NMR (CDCl$_3$) δ: 8.43 (brs, 3H), 7.74-7.65 (m, 2H), 7.55 (td, J=8.4, 2.8 Hz, 1H), 4.26 (q, J=5.5 Hz), 3.85 (s, 3H); $^{13}$C NMR (100 MHz, CDCl$_3$) δ: 165.8, 162.1 (d, J=250 Hz), 134.8 (d, J=10.0 Hz), 131.9 (d, J=10.0 Hz), 131.7, 120.1 (d, J=20.0 Hz), 117.7 (d, J=30.0 Hz), 53.2, 40.3.

Step 4: Methyl 2-t-butyloxycarbonylaminomethyl-5-fluorobenzoate

| Material | MW | Amount | Moles |
|---|---|---|---|
| ammonium salt 4 | 219.64 | 3.42 kg | 15.6 |
| (Boc)$_2$O | 218.25 | 3.73 kg | 17.1 |
| NMM | 101.15 (d = 0.920) | 1.73 kg | 17.1 |
| 40 wt. % MeNH$_2$ | 31.06 | 1.21 kg | 15.6 |
| toluene | | 31 L | |
| 0.1M EDTA Na sol'n | | 6.2 L | |
| 25% brine | | 6.2 L | |

To the ammonium salt 4 (3.42 kg) in toluene (31 L) was added (Boc)$_2$O (3.73 kg), followed by NMM (1.73 kg), at 15° C.-20° C. over 1 hour. The reaction mixture was aged at room temperature for 15-24 hours, followed by the addition of 40 wt % methylamine aqueous (1.21 kg) at 5° C.-10° C., after which the mixture was aged at the same temperature for 2 hours to quench the excess (BOC)$_2$O. The reaction mixture was then worked up by charging water (12 L). After phase cut, the organic layer was washed with 0.1 M EDTA sodium solution (6.2 L), 25% brine (6.2 L), and concentrated to total volume (20 L), which was divided by two equal amount portions for amidation in two batches.

HPLC conditions: column: Zorbax, Rx C8 250×4.6 mm; temperature: 30° C.; detection at 210 nm; mobile phase: 0.1% aq H$_3$PO$_4$ (A)/MeCN (B); gradient: 90:10 (A)/(B) to 10:90 over 15 min, 10:90 hold for 5 min, 10:90 to 90:10 (A)/(B) over 10 seconds; flow rate: 1 ml/min; retention time for the desired monoester: 14.5 min.

Evaporation of a sample to dryness gave a colorless oil: $^1$H NMR (CDCl$_3$) δ: 7.65 (dd, J=9.4, 2.4, 1H), 7.50 (dd, J=8.0, 5.7 Hz, 1H), 7.18 (dd, J=8.0, 2.8 Hz, 1H), 5.31 (brs, 1H), 4.47 (d, J=6.6 Hz, 1H), 3.91 (s, 3H), 1.41 (s, 9H); $^{13}$C NMR (100 MD, CDCl$_3$) δ: 166.5, 1.61.5 (d, J=250 Hz), 155.8, 137.0, 132.8 (d, J=10.0 Hz), 130.2 (d, J=10.0 Hz), 119.6 (d, J=30.0 Hz), 117.7 (d, J=20.0 Hz), 79.2, 52.4, 42.9, 28.4 (3C).

Step 5: N-methyl 2-t-butyloxycarbonylaminomethyl-5-fluorobenzenecarboxamide

Step 6: N-methyl 2-amino-5-fluorobenzenecarboxamide, HCl salt

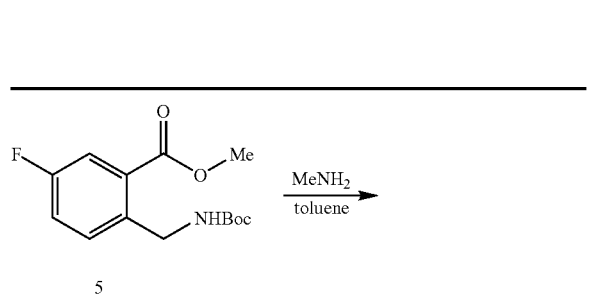

5

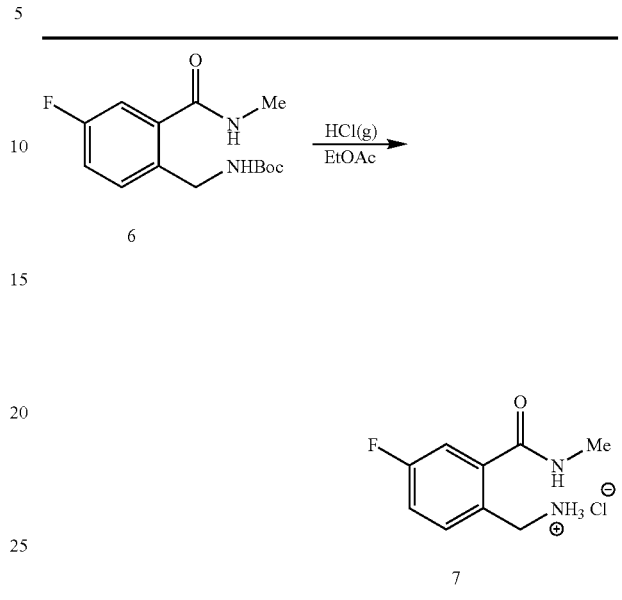

6

6

7

| Material | MW | Amount | Moles |
|---|---|---|---|
| methyl benzoate 5 | 283.30 | | 7.77 in toluene |
| methylamine | 31.06 | 0.483 kg | 15.6 |
| toluene | | 5 L | |
| heptane | | 50 L + 25 L | |

| Material | MW | Amount | Moles |
|---|---|---|---|
| N-methyl amide 6 | 282.31 | 3.14 kg | 11.1 |
| HCl (gas) | 36.46 | 3.25 kg | 89.0 |
| EtOAc | | 21.4 L + 42.8 L + 30 L | |
| heptane | | 40 L | |

The crude methyl benzoate 5 in toluene (7.77 moles in 10 L) was cooled to −20° C. and methylamine (0.483 kg) gas was added. The mixture was then heated in an autoclave at 80-85° C. for 48 hours. The reaction was monitored by HPLC. After cooling to about 50° C., the reaction mixture was transferred to a large round bottom flask for batch concentration. The solution was concentrated, producing a slurry, and solvent-switched to toluene (total vol. 12 L), after which heptane (50 L) was slowly charged to the slurry. The resulting slurry was aged at 0° C. for 1 hour. The white crystalline solid was filtered off, rinsed with heptane (25 L), and dried under vacuum with a nitrogen sweep to give methylaamide.

HPLC conditions: column: Zorbax, Rx C8 250×4.6 mm; temperature: 30° C.; detection at 210 nm; mobile phase: 0.1% aq $H_3PO_4$ (A)/MeCN (B); gradient: 90:10 (A)/(B) to 10:90 over 15 min, 10:90 hold for 5 min, 10:90 to 90:10 (A)/(B) over 10 seconds; flow rate: 1 mL/min; retention time for the desired monoester: 11.6 min. $^1$H NMR (CDCl$_3$) δ: 7.43 (dd, J=8.4, 5.5 Hz, 1H), 7.15-7.07 (m, 2 H), 6.52 (brs, 1H), 5.66 (brs, 1H), 4.28 (d, J=6.4 Hz, 2H), 3.10 (d, J=4.8H, 3 Et), 1.42 (s, 9H); $^{13}$C NMR (100 MHz, CDCl$_3$) δ: 169.0, 161.5 (d, J=250 Hz), 156.1, 137.3, 133.5, 132.0 (d, J=10.0 Hz), 117.2 (, d, J=20.0 Hz), 114.3 (d, J=20.0 Hz), 79.4, 42.2, 26.7.

To a solution of ethyl acetate (21.4 L) was bubbled HCl gas (3.25 kg) at −20° C. N-Methyl amide 6 (3.14 kg) was charged to the HCl-EtOAc solution, and the reaction mixture was warmed to ambient temperature (17° C.) in about 3 hours and aged for 2-4 hours. The reaction was monitored by HPLC. The reaction mixture was diluted with EtOAc (42.8 L), and the resulting slurry was aged at 0-5° C. for 0.5 hour. The crystalline solid was filtered off and washed with EtOAc (30 L), then with heptane (40 L), and then dried under vacuum with a nitrogen sweep to give the salt. The crystalline solid (2.434 kg) was recrystallized by dissolved in methanol (10.5 L) at 30° C. To the resulting solution was added EtOAc (64 L), producing a slurry that was aged at 0-5° C. for 1 hour. The white crystalline solid was filtered off and washed with EtOAc (30 L), dried under vacuum with nitrogen sweep to give the desired product.

HPLC conditions: column: Zorbax, Rx C8 250×4.6 mm; temperature: 30° C.; detection at 210 nm; mobile phase: 0.1% aq $H_3PO_4$ (A)/MeCN (B); Gradient: 90:10 (A)/(B) to 10:90 over 15 min, 10:90 hold for 5 min, 10:90 to 90:10 (A)/(B) over 10 seconds; flow rate: 1 mL/min; retention time for the desired monoester: 3.33 min. $^1$H NMR (CDCl$_3$) δ: 8.84 (brs, 1H), 8.05 (brs, 3H), 7.55 (dd, J=8.3, 5.8 Hz, 1H), 7.46-7.13 (m, 2H), 4.01 (s, 3H), 2.77 (d, J=4.6 Hz, 3H); $^{13}$C NMR (100 MHz, CDCl$_3$) δ: 167.9, 162.0 (d, J=250 Hz), 157.9, 138.5 (d, J=10.0 Hz), 134.3 (d, J=10.0 Hz), 129.2, 117.6 (d, J=20.0 Hz), 115.5 (d, J=20.0 Hz), 40.7, 26.7.

Step 7: 5-(1,1-Dioxido-1,2-thiazinan-2-yl)-8-hydroxy-1,6-naphthyridine-7-carboxylic acid

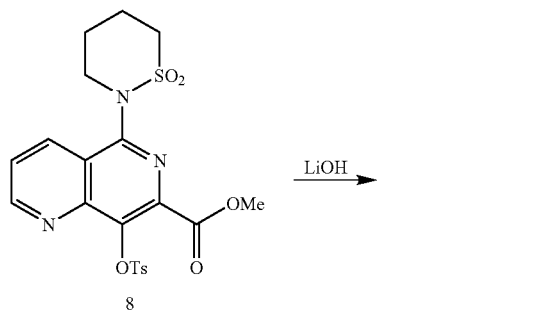

| Material | MW | Equivalents | Amount | Moles |
|---|---|---|---|---|
| Tosylate 8 | 491.5 | 1.0 | 3.3 kg | 6.7 |
| 2-propanol | | 4 L/kg 8 | 13.2 L | |
| water | | 4 L/kg 8 | 13.2 L | |
| LiOH•H$_2$O | 41.96 | 3.3 | 0.93 | 22.2 |
| 2N HCl | | 2.6 | 8.7 L | 17.5 |
| Water | | 5 L/kg 8 | 4 × 4.3 L | |

A 50-L flask equipped with a mechanical stirrer, temperature probe, addition funnel, and nitrogen inlet was charged with 2-propanol (13.2 L) and tosylate 8 (3.3 kg). The lithium hydroxide monohydrate (0.93 kg) was then charged as a solution in GMP water (13.2 L) at 20-25° C. The resulting suspension was warmed to 60° C. where a homogeneous yellow solution was obtained. The reaction was aged until complete conversion to 9 was reached as determined by HPLC assay (4-16 hours). The resulting yellow suspension was cooled to about 20° C. and diluted with 2 N HCl (8.7 L) over 0.5 hour. The pH was between 1.3-1.6 at 20° C. following HCl addition. The suspension was cooled to about 20° C., filtered, and the cake was washed with water (4×4.3 L) as displacement washes. The cake was dried on the filter pot under nitrogen and house vacuum until the water content was <6 wt % by Karl Fisher titration. The purity of carboxylic acid phenol 9 was >99.4 A % by HPLC assay.

Step 8: 5-(1,1-Dioxido-1,2-thiazinan-2-yl)-N-{4-fluoro-2-[(methylamino)carbonyl]benzyl}-8-hydroxy-1,6-naphthyridine-7-carboxamide

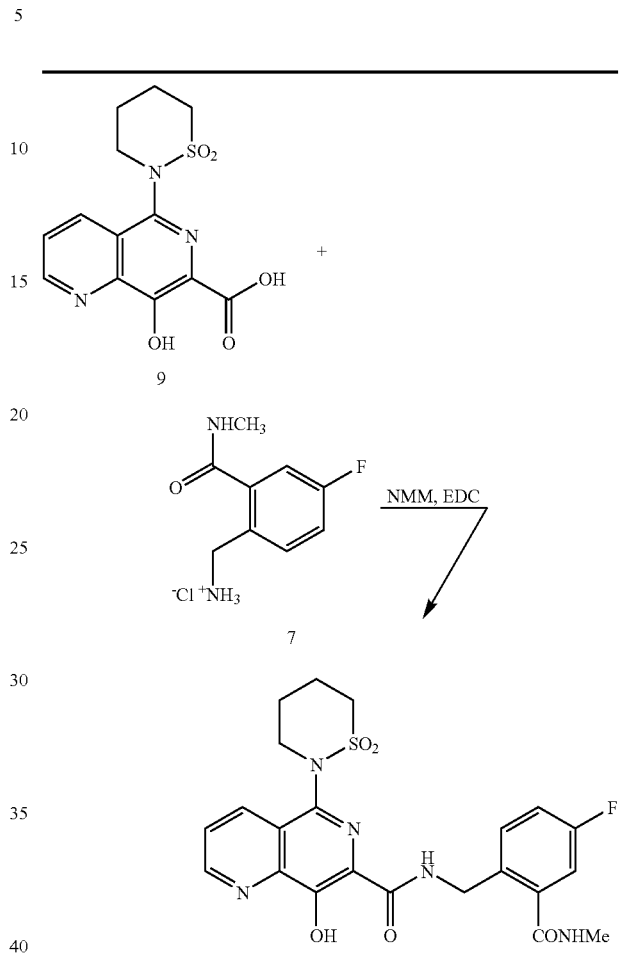

| Material | MW | Equivalents | Amount | Moles |
|---|---|---|---|---|
| carboxylic acid 9 | 323.33 | 1.0 | 1.63 kg | 5.04 |
| DMF | | 10 L/kg 9 | 16.3 L | |
| amine 7 | 218.66 | 1.2 | 1.32 kg | 6.05 |
| HOBt | 135.13 | 0.5 | 341 g | 2.52 |
| NMM | 101.15 | 0.9 | 456 g | 4.54 |
| EDC•HCl | 191.71 | 1.5 | 1.45 kg | 7.56 |
| water | | 10 L/kg 9 | 16.3 L | |

A 50-L flask equipped with a mechanical stirrer, temperature probe, and nitrogen inlet was charged with the dry DMF (16.3 L), carboxylic acid 9 (1.73 kg gross, 1.63 assay kg, KF=6.0 wt % water), anhydrous HOBt (341 g), amine 7 (1.32 kg), and NMM (456 g, 500 mL). The suspension was agitated at 20° C. until a homogeneous solution was obtained and then cooled to 0-5° C. The EDC (1.45 kg) was added and the reaction aged until complete conversion of 9 was reached as determined by HPLC (<0.5% 9, about 16 hours). The reaction was diluted with water (1.6 L) at 20° C., seeded (11 g), and aged for 0.5 hour. The batch was diluted with water (14.7 L) to give a 1:1 v/v ratio of water:DMF and then cooled to 0° C. The batch was then filtered and the cake washed with chilled 1:1 water:DMF (4×2.5 L) and chilled water (4×5.5 L) as displacement washes. The cake was then dried at ambient temperature under nitrogen tent/house vacuum to obtain the title product (purity: >99.0 A % by HPLC assay).

Step 9: Potassium 5-(1,1-dioxido-1,2-thiazinan-2-yl)-7-[({4-fluoro-2-[(methylamino)carbonyl]benzyl}amino)carbonyl-1,6-naphthyridin-8-olate

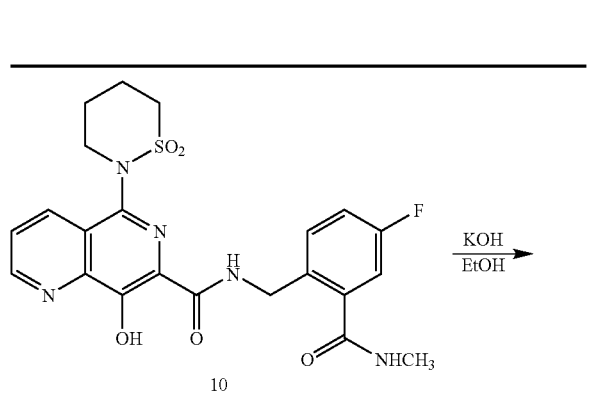

| Material | MW | Equivalents | Amount | Moles |
|---|---|---|---|---|
| carboxamide 10 | 487.1 | 1.0 | 4.2 kg | 8.61 |
| EtOH | | | 20 mL/g 10 | |
| KOH (45 wt. % aq) | 56.1 | 1.2 | 1286 g (866 mL) | 10.34 |

A 100 L cylinder equipped with a mechanical stirrer, temperature probe, addition funnel, and nitrogen inlet was charged with carboxamide 10 and EtOH (84 L) and then heated to 60° C. To the resulting yellow suspension was added aq KOH. The resulting yellow solution was filtered through a 10 μm line filter into an adjacent 100 L flask. The solution was seeded and heated at 60° C. for 3 hours and then allowed to cool to room temperature overnight. The resulting slurry was cooled to 3-4° C., filtered, and washed with 4×2 L of cold EtOH. The filter pot was placed under vacuum with a $N_2$ stream to obtain the title salt as a crystalline ethanolate salt. The purity of the salt was >99.6 A % by HPLC assay. The salt contained 6.8 wt. % ethanol by GC and 0.5 wt. % water by Karl Fisher titration.

EXAMPLE 4

Sodium 7-[({2-[(dimethylamino)carbonyl]4-fluorobenzyl}amino)carbonyl]-5-(1,1-dioxido-1,2-thiazinan-2-yl)-1,6-naphthyridin-8-olate Step 1: tert-butyl 2-[(dimethylamino)carbonyl]4-fluorobenzylcarbamate This compound was prepared in a manner similar to that described in Example 3, using dimethylamine instead of methylamine, to afford a light brown oil.

$^1$H NMR (DMSO, 400 MHz) δ 7.36 (3H, m), 7.08 (1H, dd, J=8.8, 2.6 Hz), 4.02 (2H, m), 2.99 (3H, s), 2.76 (3H, s) and 1.39 (9H, s) ppm.

Step 2: {2-[(dimethylamino)carbonyl]-4-fluorophenyl}methanaminium chloride

This compound was prepared in a manner similar to that described in Example 3 to afford a light pink solid.

$^1$H NMR (DMSO-d6, 400 MHz) δ 8.38 (2H, bs), 7.69 (1H, dd, J 8.4, 5.5 Hz), 7.39 (1H, dt, J=8.5, 1.8 Hz), 7.33 (1H, dd, J 9.0, 1.8 Hz), 3.91 (2H, s), 3.03 (3H, s), and 2.86 (3H, s) ppm.

Step 3: N-{2-[(Dimethylamino)carbonyl]4-fluorobenzyl}-5-(1,1-dioxido-1,2-thiazinan-2-yl)-8-hydroxy-1,6-naphthyridine-7-carboxamide

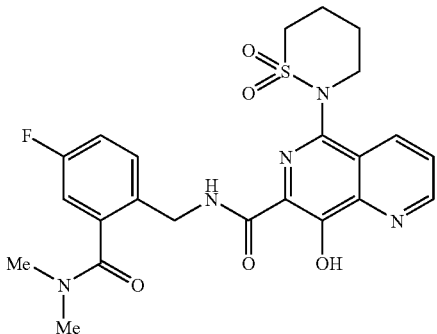

In a similar manner as described for Example 3, the title compound was prepared as a light yellow solid.

$^1$H NMR (DMSO-d6, 400 MHz) δ 9.17 (2H, m), 8.45 (1H, m), 7.87 (1H, m), 7.52 (1H, m), 7.26 (2H, m), 4.54 (2H, m), 3.84 (2H, m), 3.65 (1H; m), 3.48 (1H, m), 3.02 (3H, s), 2.85 (3H, s), 2.30 (3H, m), and 1.66 (1H, m) ppm.

Step 4: Sodium 7-[({2-[(dimethylamino)carbonyl]-4-fluorobenzyl}amino)-carbonyl]-5-(1,1-dioxido-1,2-thiazinan-2-yl)-1,6-naphthyridin-8-olate In a similar manner as described for Example 3, the title compound was prepared as a yellow solid.

$^1$H NMR (DMSO-d6, 400 MHz) δ 12.05 (1H, bs), 8.78 (1H, m), 8.28 (1H, d, J=8.2 Hz), 7.55 (1H, dd, J=8.2, 4.3 Hz), 7.48 (1H, m), 7.21 (1H, m), 7.09 (1H, m), 4.49 (2H, m), 3.83 (3H, m), 3.44 (2H, m), 3.01 (3H, s), 2.78 (3H, s), 2.24 (2H, m), and 1.51 (1H, m) ppm. ES HRMS: calc'd for $C_{23}H_{24}FN_5O_5S+H$, 502.1555, observed 502.1557.

EXAMPLE 5

Sodium 7-[({2-[(dimethylamino)carbonyl]4-fluorobenzyl}amino)carbonyl]-5-[methyl(methylsulfonyl)amino]-1,6-naphthyridin-8-olate

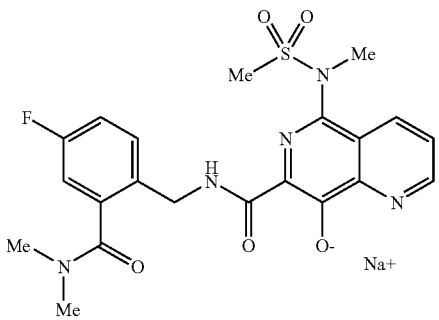

Step 1: Methyl 5-[methyl(methylsulfonyl)amino]-8-{[(4-methylphenyl)sulfonyl]oxy}-1,6-naphthyridine-7-carboxylate

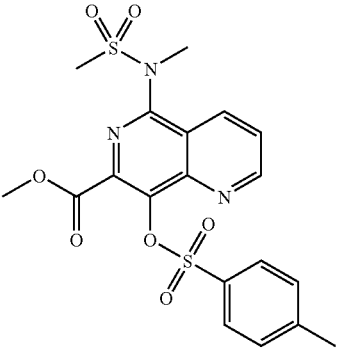

In a dried sealable pressure tube flushed with nitrogen was placed methyl 5-bromo-8-{[(4-methylphenyl)sulfonyl]oxy}-1,6-naphthyridine-7-carboxylate (500 mg, 1.14 mmol, prepared as described in Example 2, Step 2), N-methylmethanesulfonamide (168 mg, 1.54 mmol, prepared as in *J. Chem. Soc., Perkins Trans.* 1986, 2 (8): 1211-16), 2,2'-bipyridyl (241 mg, 1.54 mmol), dry DMF (3 mL) and copper(I) oxide (221 mg, 1.54 mmol). The tube was capped and heated to 85° C. overnight. In the morning, the reaction was cooled and filtered through a glass fiber filter, washing with chloroform. The filtrate was diluted with chloroform (about 100 mL total volume) and stirred with an EDTA solution (5 g EDTA in 100 mL water) for two hours or until the aqueous layer became aqua in color and the organic layer became yellow. The layers were separated and the aqueous layer was extracted twice more with chloroform. The combined organic extracts were dried over sodium sulfate, filtered, and concentrated in vacuo. The residue was purified by flash column chromatography (ISCO column, 110 g silica) eluting with a 0-5% MeOH/CHCl$_3$ gradient over 35 minutes. The concentrated fractions were triturated with methanol to give the product as a white solid.

$^1$H NMR (DMSO-d6, 400 MHz) δ 9.04 (1H, dd, J=4.2, 1.5 Hz), 8.67 (1H, dd, J=8.4, 1.5 Hz), 7.87 (1H, dd, J=8.6, 4.2 Hz), 7.75 (2H, d, J=8.2 Hz); 7.44 (2H, d, J=8.6 Hz), 3.76 (3H, s), 3.36 (3H, s), 3.30 (3H, s) and 2.43 (3H, s) ppm.

Step 2: Methyl 8-hydroxy-5-[methyl(methylsulfonyl)amino]-1,6-naphthyridine-7-carboxylate

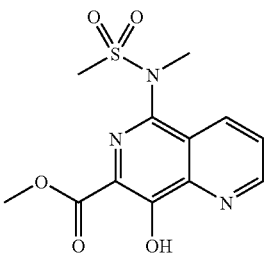

A solution of sodium methoxide (122 mg, 2.26 mmol) in dry methanol (5 mL) was added to methyl 5-[methyl(methylsulfonyl)amino]-8-{[(4-methylphenyl)sulfonyl]oxy}-1,6- naphthyridine-7-carboxylate (420 mg, 0.90 mmol) dissolved in a minimum amount of DMF and the resulting solution was heated to 50° C. for one hour. The reaction was cooled, glacial acetic acid (104 μL, 1.80 mmol) was added and the reaction was concentrated to dryness in vacuo. The resulting residue was triturated with ethanol and the solids were collected by vacuum filtration to give the desired product as a yellow solid.

$^1$H NMR (DMSO-d6, 400 MH) δ 9.21 (1H, dt, J=4.0, 1.6 Hz), 8.61 (1H, dt, J=8.4, 1.6 Hz), 7.92 (1H, m), 3.94 (3H, d, J=1.3 Hz), and 3.28 (6H, m) ppm.

Step 3: 8-Hydroxy-5-[methyl(methylsulfonyl) amino]-1,6-naphthyridine-7-carboxylic acid

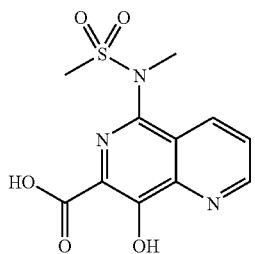

Sodium hydroxide (2.31 mL, 2.31 mmol, 1N solution) was added to a suspension of methyl 8-hydroxy-5-[methyl(methylsulfonyl)amino]-1,6-naphthyridine-7-carboxylate (240 mg, 0.77 mmol) in a 1:1 solution of THF/methanol (5 mL) and the resulting mixture was heated overnight at 50° C. In the morning, the homogeneous solution was acidified to a pH=4 using 1N HCl solution. The reaction was cooled and the solids that had precipitated out of solution were collected by vacuum filtration to give the desired product as an off-white solid.

$^1$H NMR (DMSO-d6, 400 MHz) δ 9.22 (1H, dd, J=4.2, 1.5 Hz), 8.64 (1H, dd, J=8.5, 1.4 Hz), 7.93 (1H, dd, J=8.4, 4.2 Hz), 3.29 (3H, s), and 3.28 (3H, s) ppm.

Step 4: N-{2-[(Dimethylamino)carbonyl]-4-fluorobenzyl}-8-hydroxy-5-[methyl(methylsulfonyl) amino]-1,6-naphthyridine-7-carboxamide

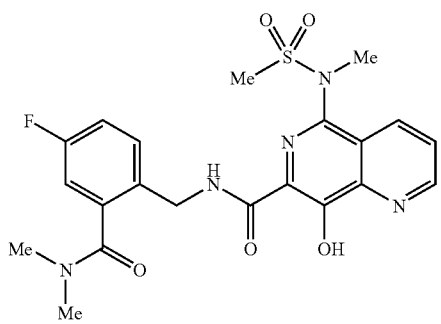

In a manner similar to that described in Example 3, 8-hydroxy-5-[methyl(methylsulfonyl)amino]-1,6-naphthyridine-7-carboxylic acid was coupled with {2-[(dimethylamino)carbonyl]-4-fluorophenyl}methanaminium chloride (prepared as described in Example 4) to give the desired product as an off-white solid which was taken on as is to the sodium salt.

LC/MS: calc'd for $C_{21}H_{22}FN_5O_5S$ 475.5, observed MH+476.3.

Step 5: Sodium 7-[({2-[(dimethylamino)carbonyl]-4-fluorobenzyl}amino)carbonyl]-5-[methyl(methylsulfonyl)amino]-1,6-naphthyridin-8-olate In a manner similar to that described for Example 3, the free base was converted to the desired salt, that was obtained as a yellow solid.

$^1$H NMR DMSO-d6, 400 MHz) δ 12.00 (1H, bs), 8.79 (1H, m), 8.28 (1H, d, J=8.1 Hz), 7.57 (1H, dd, J=8.0, 3.8 Hz), 7.47 (1H, dd, J=8.6, 5.7 Hz), 7.28 (1H, dt, J=8.7, 2.8 Hz), 7.13 (1H, dd, J=8.9, 2.7 Hz), 4.42 (2H, d, J=5.0 Hz), 3.28 (3H, s), 3.16 (3H, s), 3.01 (3H, s), and 2.79 (3H, s) ppm. ES HRMS: calc'd for C21H21FN5NaO5S 498.1218, observed 498.1218.

EXAMPLE 6

Sodium 7-[({4-fluoro-2-[(methylamino)carbonyl] benzyl}amino)carbonyl]-5-[methyl(methylsulfonyl) amino]-1,6-naphthyridin-8-olate

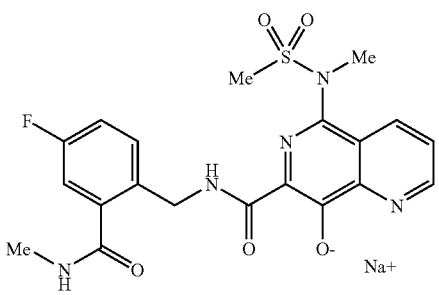

In a manner similar to that described for Example 5, the title compound was obtained as a yellow solid.

¹H NMR (DMSO-d6, 400 MHz) δ 8.79 (1H, dd, J=4.2, 1.8 Hz), 8.29 (1H, dd, J=8.3, 1.7 Hz), 7.57 (1H, dd, J=8.4, 4.2 Hz), 7.40 (1H, dd, J=8.6, 5.9 Hz), 7.20 (1H, dd, J=9.7, 2.8 Hz), 7.14 (1H, dt, J=8.6, 2.6 Hz), 4.63 (2H, m), 3.28 (3H, s), 3.16 (3H, s) and 2.78 (3H, s) ppm. ES HRMS: calc'd for $C_{20}H_{20}FN_5O_5S+H$ 461.1242, observed 462.1242.

EXAMPLE 7

Sodium 5-(1,1-dioxido-1,2-thiazinan-2-yl)-7-[({4-fluoro-2-[(isopropylamino)-carbonyl]benzyl}amino)carbonyl]-1,6-naphthyridin-8-olate

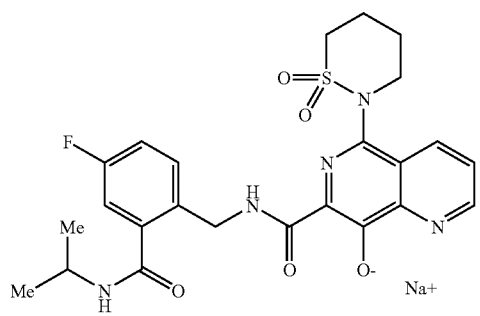

Step 1: Tert-butyl 4-fluoro-2-[(isopropylamino)carbonyl]benzylcarbamate

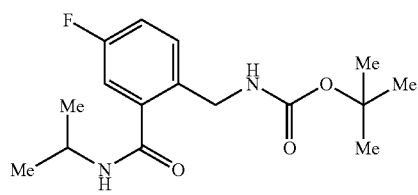

In an oven-dried high pressure bomb reactor apparatus was placed dry toluene (30 mL) and nitrogen was bubbled through the solution. Methyl 2-{[(tert-butoxycarbonyl)amino]methyl}-5-fluorobenzoate (4.0 g, 14.1 mmol, prepared as described in Example 3C, Step 4) and isopropylamine (12.0 mL, 0.14 mol) were added to the vessel. The bomb was sealed and heated to 70° C. overnight. The vessel was cooled and the reaction was concentrated to dryness in vacuo. The residue was purifed by flash column chromatography (ISCO column, 120 g silica) running a 0-30% acetone/hexane gradient over 30 minutes. The product fractions were concentrated to give the title compound as a white solid.

¹H NMR (DMSO-d6, 400 MHz) δ 8.32 (1H, d, J=7.7 Hz), 7.23-7.34 (2H, m), 7.14-7.20 (2H, m), 4.19 (2H, d, J=6.0), 4.02 (1H, m), 1.38 (9H, s), and 1.15 (6H, d, J-=6.6 Hz) ppm.

Step 2: {4-Fluoro-2-[(isopropylamino)carbonyl]phenyl}methanaminium chloride

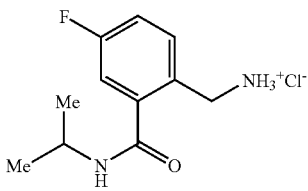

This compound was prepared in a manner similar to that described in Example 3, Step 6 to afford a white solid.

¹H NMR (DMSO-d6, 400 MHz) δ 8.66 (1H, d, J=7.5 Hz), 8.33 (3H, bs), 7.63 (1H) m), 7.40-7.45 (2H, m), 4.07 (1H, m), 4.01 (2H, s), and 1.17 (6H, d; J 7.1 Hz) ppm.

Step 3: 5-(1,1-Dioxido-1,2-thiazinan-2-yl)-N-{4-fluoro-2-[(isopropylamino)carbonyl]benzyl}-8-hydroxy-1,6-naphthyridine-7-carboxamide

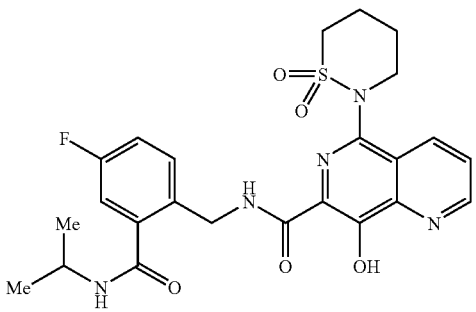

5-(1,1-Dioxido-1,2-thiazinan-2-yl)-8-hydroxy-1,6-naphthyridine-7-carboxylic acid (200 mg, 0.62 mmol, prepared as described in Example 3, Step 7), 1-[3-(dimethylamino)propyl]-3-ethylcarbodiimide hydrochloride (154 mg, 0.80 mmol), and 1-hydroxy-7-azabenzotriazole (109 mg, 0.80 mmol) were added to dry DMF (15 mL) and stirred for 30 minutes to preform the activated ester. {4-Fluoro-2-[(isopropylamino)carbonyl]phenyl}methanaminium chloride (168 mg, 0.68 mmol) and triethylamine (95 μL, 0.68 mmol) were added and the reaction was stirred overnight at room temperature. The reaction was poured into water, the pH was adjusted to ~10 using 1N NaOH, and resulting solution was extracted several times with CHCl₃. The combined organic extracts were dried over Na₂SO₄, filtered, and concentrated to dryness in vacuo. The residue was redissolved in basic water and CHCl₃, acidified to pH=4 using 1N HCl and extracted several times with CHCl₃. The combined organic extracts were dried over Na₂SO₄, filtered, and concentrated to a whitish solid. Methanol was added to the flask and the flask was sonicated for 5 minutes. The resulting solids were collected by vacuum filtration to give the title compound as an off-white solid.

¹H NMR (DMSO-d6, 400 MHz) δ 13.71 (1H, s), 9.51 (1H, m), 9.19 (1H, m), 8.58 (2H, m), 7.89 (1H, m), 7.52 (1H, m), 7.35 (2H, m), 4.63 (2H, d, J=5.5 Hz), 4.10 (1H, m), 3.92 (1H, m), 3.76 (1H, m), 3.66 (1H, m), 3.46 (1H, m), 2.33 (3H, m), 1.65 (1H, m), and 1.20 (6H, dd, J=6.6, 1.7 Hz)·ppm.

Step 4: Sodium 5-(1,1-dioxido-1,2-thiazinan-2-yl)-7-[({4-fluoro-2-[(isopropylamino)carbonyl]benzyl}amino)carbonyl]-1,6-naphthyridin-8-olate 5-(1,1-Dioxido-1,2-thiazinan-2-yl)-N-{4-fluoro-2-[(isopropylamino)carbonyl]benzyl}-8-hydroxy-1,6-naphthyridine-7-carboxamide (203 mg, 0.39 mmol) was suspended in acetone (2 mL) and sodium hydroxide (0.39 mL, 0.39 mmol, 1N aqueous solution) was added. The flask was gently warmed to make the solution homogeneous and the solution was then filtered through a glass fiber filter to remove any dust. The solution was stirred at room temperature until solids crashed out of solution. The solids were collected by vacuum filtration to give the title compound as a yellow solid.

$^1$H NMR (DMSO-d6, 400 MHz) δ 12.16 (1H, bs), 8.78 (1H, dd, J=4.2, 1.8 Hz), 8.68 (1H, m), 8.28 (1H, d, J=8.2 Hz), 7.55 (1H, dd, J=8.2, 4.2 Hz), 7.45 (1H, m), 7.23 (1H, dt, J=8.6, 2.7 Hz), 7.17 (1H, m), 4.60 (2H, d, J=5.7 Hz), 4.09 (1H, m), 3.85 (2H, m), 3.49 (1H, m), 3.22 (1H, m), 2.37 (1H, m), 2.22 (2H, m), 1.52 (1H, m) and 1.18 (6H, d, J=6.6 Hz) ppm.

EXAMPLE 8

Sodium 5-(1,1-dioxido-1,2-thiazinan-2-yl)-7-[({2-[(ethylamino)carbonyl]-4-fluorobenzl}amino)carbonyl]-1,6-naphthyrdin-8-olate

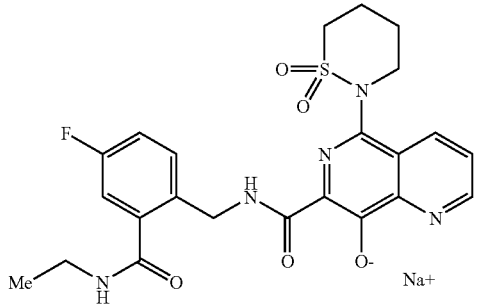

Step 1: Tert-butyl 2-[(ethylamino)carbonyl]-4-fluorobenzylcarbamate

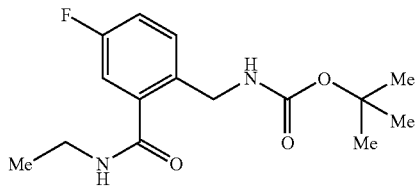

This compound was prepared in a manner similar to that described in Example 7, Step 1 using ethylamine instead of isopropylamine. The reaction was concentrated to dryness and taken on without further purification.

Step 2: {2-[(Ethylamino)carbonyl]-4-fluorophenyl}methanaminium chloride

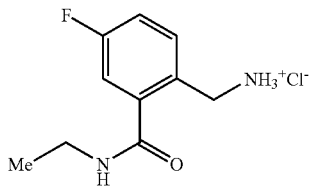

This compound was prepared in a manner similar to that described in Example 3, Step 6 to afford an off-white solid.

$^1$H NMR (DMSO-d6, 400 MHz) δ 8.86 (1H, s), 8.38 (3H, bs), 7.64 (1H, m), 7.41-7.47 (2H, m), 4.03 (2H, d, J=5.0 Hz), 3.29 (2H, m), and 1.15 (3H, t, J=7.1 Hz) ppm.

Step 3: 5-(1,1-Dioxido-1,2-thiazinan-2-yl)-N-{2-[(ethylamino)carbonyl]-4-fluorobenzyl}-8-hydroxy-1,6-naphthyridine-7-carboxamide

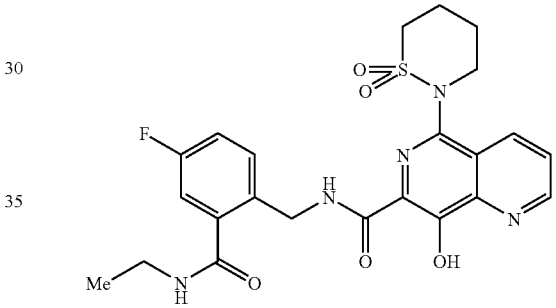

In a similar manner as described for Example 7, Step 3 the title compound was prepared as a light yellow solid.

$^1$H NMR(DMSO-d6, 400 MHz) δ 13.71 (1H, s), 9.52 (1H, t, J=6.4 Hz), 9.19 (1H, d, J=4.2 Hz), 8.73 (1H, t, J=5.2 Hz), 8.58, (1H, d, J=8.6 Hz), 7.89 (1H, dd, J=8.4, 4.2 Hz), 7.53 (1H, dd, J=8.4, 5.6 Hz), 7.40 (1H, dd, J=9.2, 2.4 Hz), 7.33 (1H, m), 4.64 (2H, d, J=6.4 Hz), 3.94 (1H, m), 3.66-3.76 (2H, m), 3.46 (1H, m), 3.33 (2H, m), 2.33 (3H, m), 1.64 (1H, m), and 1.17 (3H, t, J=7.2 Hz) ppm.

Step 4: Sodium 5-(1,1-dioxido-1,2-thiazinan-2-yl)-7-[({2-[(ethylamino)carbonyl]-4-fluorobenzyl}amino)carbonyl]-1,6-naphthyridin-8-olate In a similar manner as described for Example 7, Step 4 the title compound was prepared as a light yellow solid.

$^1$H NMR (DMSO-d6, 400 MHz) δ 12.11 (1H, s), 8.78 (1H, d, J=4.0 Hz), 8.73 (1H, t, J=5.0 Hz), 8.29 (1H, d, J=8.2 Hz), 7.55, (1H, dd, J=8.2, 4.1 Hz), 7.45 (1H, dd, J=8.4, 5.9 Hz), 7.03-7.25 (2H, m), 4.61 (2H, d, J=6.0 Hz), 3.78-3.86 (2H, m), 3.51 (1H, m), 3.29 (2H, m), 3.22 (1H, m), 2.45 (1H, m), 2.23 (2H, m), 1.52 (1H, m), and 1.15 (3H, t, J=7.2 Hz) ppm.

EXAMPLE 9

Sodium 7-({[2-(aminocarbonyl)-4-fluorobenzyl]amino}carbonyl)-5-(1,1-dioxido-1,2-thiazinan-2-yl)-1,6-naphthyridin-8-olate

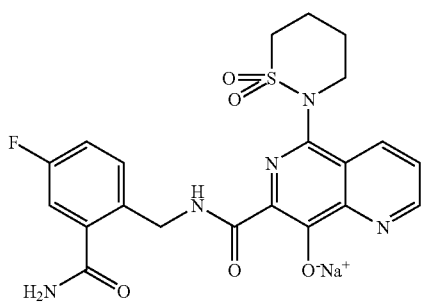

Step 1: 2-{[(Tert-butoxycarbonyl)amino]methyl}-5-fluorobenzoic acid

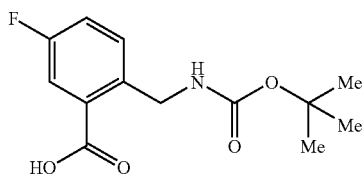

Methyl 2-{[(tert-butoxycarbonyl)amino]methyl}-1-5-fluorobenzoate (4.0 g, 14.1 mmol, prepared as described in Example 3C, Step 4) was dissolved in a 1:1 solution of methanol and THF (40 mL). Sodium hydroxide (15.5 mL, 15.5 mmol, 1N aqueous solution) was added and the reaction was stirred for 2 hours at room temperature. The reaction was acidified to a pH=4 using 3N HCl and concentrated to dryness in vacuo. The residue was purified by prep HPLC (Gilson semi preparative HPLC system using a Nova pak column (10×40 mm I.D. cartridge, C18,6 μm pore size) eluting with 95-5% water (0.025% TFA)/acetonitrile (0.025% TFA) at 35 mL/min) in three runs. The fractions containing product were concentrated to afford the title compound as a white solid.

$^1$H NMR (DMSO-d6, 400 MHz) δ 13.32 (1H, bs), 7.59 (1H, dd, J=9.5, 2.2 Hz), 7.41-7.44 (2H, m), 7.26 (1H, t, J=6.1 Hz), 4.44 (2H, d, J=6.1 Hz), and 1.40 (9H, s) ppm.

Step 2: Tert-butyl 2-(aminocarbonyl)-4-fluorobenzylcarbamate

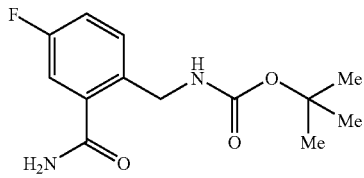

2-{[(Tert-butoxycarbonyl)amino]methyl}-5-fluorobenzoic acid (800 mg, 2.97 mmol), 1-[3-(dimethylamino)propyl]-3-ethylcarbodiimide hydrochloride (854 mg, 4.46 mmol), and 1-hydroxy-7-azabenzotriazole (607 mg, 4.46 mmol) were added to dry DMF (10 mL) and stirred for 30 minutes to preform the activated ester. Ammonia gas was bubbled through the solution for 30 seconds and the reaction was allowed to stir for 5 minutes. The solvent was removed in vacuo and the residue was purified by flash column chromatography (ISCO column, 120 g silica) running a gradient of 0-40% acetone/hexane over 35 min. The product fractions were concentrated to afford the title compound as a white solid.

$^1$H NMR (DMSO-d6, 400 MHz) δ 7.93 (1H, s), 7.56 (1H, s), 7.19-7.35 (4H, m), 4.25 (2H, d, J=6. Hz), and 1.39 (9H, s) ppm.

Step 3: [2-(Aminocarbonyl)4-fluorophenyl]methanaminium chloride

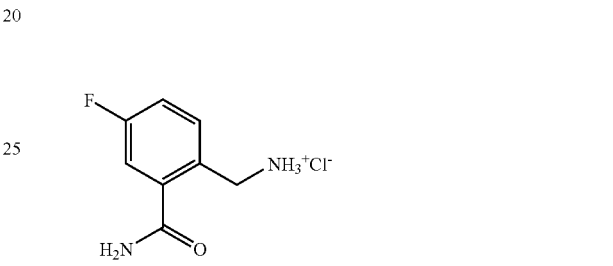

This compound was prepared in a manner similar to that described in Example 3, Step 6 to afford a white solid.

$^1$H NMR (DMSO-d6, 400 MHz) δ 8.29 (4H, bs), 7.89 (1H, s), 7.63 (1H, dd, J=8.4, 5.7 Hz), 7.52 (1H, dd, J=9.4, 2.6 Hz), 7.44 (1H, dt, J=8.5, 2.7 Hz), and 4.07 (2H, s) ppm.

Step 4: N-[2-(Aminocarbonyl)-4-fluorobenzyl]-5-(1,1-dioxido-1,2-thiazinan-2-yl)-8-hydroxy-1,6-naphthyridine-7-carboxamide

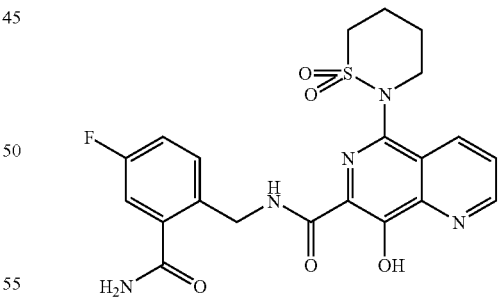

In a similar manner as described for Example 7, Step 3 the title compound was prepared as a light yellow solid.

$^1$H NMR (DMSO-d6, 400 MHz) δ 13.68 (1H, bs), 9.47 (1H, bs), 9.18 (1H, d, J=4.2 Hz), 8.58 (1H, d, J=8.4 Hz), 8.21, (1H, s), 7.88 (1H, dd, J=8.4, 4.2 Hz), 7.77 (1H, s), 7.53 (1H, dd, J=8.3, 5.7 Hz), 7.45 (1H, dd, J=9.3, 2.2 Hz), 7.34 (1H, dt, J=8.4, 2.1 Hz), 4.68 (2H, d, J=6.2 Hz), 3.94 (1H, m), 3.77 (1H, m), 3.58 (1H, m), 3.45 (1H, m), 2.30-2.37 (3H, m), and 1.62 (1H, m) ppm.

Step 5: Sodium 7-({[2-(aminocarbonyl)₄-fluorobenzyl]aminocarbonyl)-5-(1,1-dioxido-1,2-thiazinan-2-yl)-1,6-naphthyridin-8-olate In a similar manner as described for Example 7, Step 4 the title compound was prepared as a light yellow solid.

¹H NMR (DMSO-d6, 400 MHz) δ 12.12 (1H, bs), 8.78 (1H, d, J=2.6 Hz), 8.30 (2H, m), 7.57, (2H, m), 7.46 (1H, dd, J=9.2, 5.7 Hz), 7.22 (2H, m), 4.66 (2H, d, J=5.5 Hz), 3.75-3.86 (2H, m), 3.54 (1H, m), 3.23 (1H, m), 2.43 (1H, m), 2.23 (2H, m), and 1.52 (1H, m) ppm.

EXAMPLE 10

Sodium 7-({[2-(aminocarbonyl)-4-fluorobenzyl]amino}carbonyl)-5-[methyl(methyl-sulfonyl)amino]-1,6-naphthyridin-8-olate

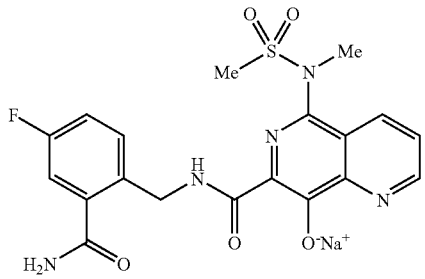

Step 1: N-[2-(Aminocarbonyl)-4-fluorobenzyl]-8-hydroxy-5-[methyl(methylsulfonyl)amino]-1,6-naphthyridine-7-carboxamide

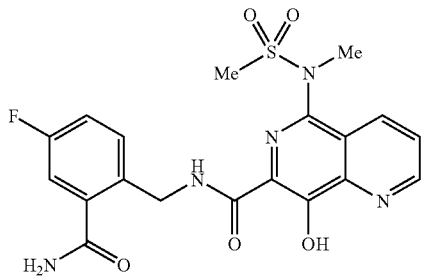

In a similar manner as described for Example 7, Step 3, [2-(aminocarbonyl)4-fluorophenyl]methanaminium chloride (from Example 9, Step 3) was coupled with 8-hydroxy-5-[methyl(methylsulfonyl)amino]-1,6-naphthyridine-7-carboxylic acid (from Example 5, Step 3) to afford the title compound.

¹H NMR (DMSO-d6, 400 MHz) δ 13.63 (1H, bs), 9.66 (1H, bs), 9.18(1H, d, J=2.8 Hz), 8.61 (1H, d, J=8.4 Hz), 8.15 (1H, s), 7.88 (1H, dd, J=8.5, 4.1 Hz), 7.75 (1H, s), 7.49 (1H, dd, J=8.5, 5.5 Hz), 7.40 (1H, dd, J=9.3, 2.8 Hz), 7.30 (1H, dt, J=8.5, 2.6 Hz), 4.70 (2H, d, J=6.4 Hz), 3.34 (3H, s), and 3.21 (3H, s) ppm.

Step 2: Sodium 7-({[2-(aminocarbonyl)-4-fluorobenzyl]amino}carbonyl)-5-[methyl(methylsulfonyl)amino]-1,6-naphthyridin-8-olate In a similar manner as described for Example 7, Step 4 the title compound was prepared as a light yellow solid.

¹H NMR (DMSO-d6, 400 MHz) δ 12.02 (1H, s), 8.79 (1H, d, J=4.2 Hz), 8.30 (2H, m), 7.58, (2H, m), 7.45 (1H, m), 7.23 (2H, m), 4.65 (2H, d, J=5.9 Hz), 3.27 (3H, s), and 3.16 (3H, s) ppm. ES HRMS: calc'd for $C_{19}H_{18}FN_5O_5S+H$, 448.1085, observed 448.1077

EXAMPLE 11

5-(1,1-Dioxido-1,2-thiazinan-2-yl)-8-hydroxy-N-{2-[(methylamino)carbonyl]benzyl}-1,6-naphthyridine-7-carboxamide

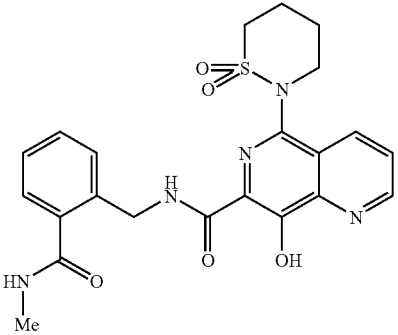

Step 1: 2-(Aminomethyl)-N-methylbenzamide

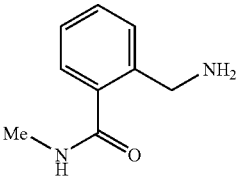

A suspension of 4-chloro-2-methylbenzoic acid (15.0 g, 87.9 mmol), N-bromosuccinimide (15.9 g, 89.3 mmol), and benzoyl peroxide (1.07 g, 4.4 mmol) in carbon tetrachloride (340 mL) was heated to reflux for 1 hour. Additional NBS (9.0 mmol) was added over this period to drive the reaction toward completion. The reaction was cooled, and filtered. The filtrate was washed once with aqueous sodium bicarbonate, followed by two washes with water. The organic fraction was dried over magnesium sulfate and then filtered. To this was added triethylamine (12.0 mL, 86.1 mmol), till the solution was basic and stirred overnight at room temperature. After which, water was added and extracted three times with chloroform. The combined organics were dried over magnesium sulfate, filtered, and concentrated in vacuo. The product was recrystallized from a mixture of methanol, and diethyl ether as 5-chloro-2-benzofuran-1(3H)-one.

Methylamine gas was condensed into a sealed tube at −78° C., and a solution of 5-chloro-2-benzofuran-1(3H)-one (6.68 g, 39.8 mmol) in methanol (30 mL) was added. The solution was slowly warmed to room temperature overnight; The reaction was concentrated in vacuo, and the residue was partitioned between water and and chloroform. After three extractions with chloroform, the combined organics were dried over sodium sulfate, filtered, and concentrated in vacuo to afford 4-chloro-2-(hydroxymethyl)-N-methylbenzamide.

To a solution of 4-chloro-2-(hydroxymethyl)-N-methylbenzamide (5.81 g, 29.2 mmol) in methylene chloride (200 mL) cooled in an ice bath, was added triethylamine (5.10 mL, 36.6 mmol) and methanesulfonyl chloride (2.50 mL, 32.3 mmol). After 90 min, the reaction was diluted with chloroform and partitioned with aqueous sodium bicarbonate and brine. After extracting three times with chloroform, the combined organics were dried over sodium sulfate, filtered, and concentrated in vacuo. To this residue was added DMF (50 mL) sodium azide (0.35 g, 5.4 mmol) and azidotrimethylsilane (2.6 mL, 19.6 mmol) portionwise with stirring at 40° C. for three days. The reaction was concentrated in vacuo and partitioned between chloroform and aqueous sodium bicarbonate. After extracting three times with chloroform, the combined organics were dried over sodium sulfate, filtered, and concentrated in vacuo. The residue was purified by flash column chromatography eluting with a 30-50% ethyl acetate/hexane gradient. Fractions were concentrated in vacuo to afford 2-(azidomethyl)-4-chloro-N-methylbenzamide.

2-(Azidomethyl)-4-chloro-N-methylbenzamide (0.88 g, 3.94 mmol) was dissolved in ethanol (25 mL), degassed, treated with 10% Pd on carbon (80 mg), and put under one atmosphere of hydrogen. After one hour the reaction was filtered through Celite, and concentrated in vacuo to afford 2-(aminomethyl)-N-methylbenzamide as a white solid.

$^1$H NMR (DMSO-d6, 400 MHz) δ 8.74 (1H, br d, J=4.2 Hz), 8.40 (2H, br s), 7.56 (4H, m), 4.05 (2H, s), and 2.80 (3H, d, J=4.6 Hz)⁻.

Step 2: 5-(1,1-Dioxido-1,2-thiazinan-2-yl)-8-hydroxy-N-(2-[(methylamino)carbonyl]benzyl}-1,6-naphthyridine-7-carboxamide

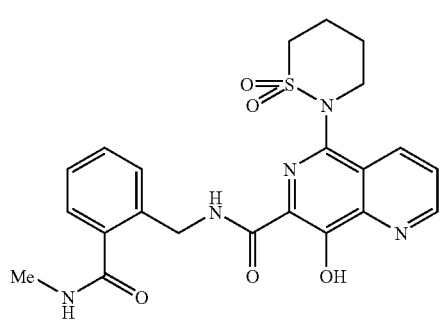

In a manner similar to that described in Example 3,5-(1,1-dioxido-1,2-thiazinan-2-yl)-8-hydroxy-1,6-naphthyridine-7-carboxylic acid was coupled with 2-(aminomethyl)-N-methylbenzamide to give the desired product as an off-white solid.

$^1$HNMR (CDCl$_3$, 400 MHz) δ 13.7 (1H, br s), 9.44 (1H, t, J=6.5 Hz), 9.20 (1H, dd, J=4.3, 1.6 Hz), 8.71 (1H, dd, J=8.5, 1.6 Hz), 7.70 (1H, dd, J=8.5, 4.3 Hz), 7.62 (1H, d, J=7.3 Hz), 7.49 (2H, m), 7.37 (1H, dt, J=7.5, 1.1 Hz), 6.13 (1H, br d, J=4.2 Hz), 4.73 (1H, dd, J=13.6, 7.2 Hz), 4.64 (1H, dd, J=13.6, 6.2 Hz), 4.18 (1H, t, J=13.0 Hz), 3.77 (1H, m), 3.63 (1H, d, J=14.3 Hz), 3.23 (1H, d, J=13.2 Hz), 3.03 (3H, d, J=4.8 Hz), 2.70 (1H, m), 2.53 (2H, m), 1.70 (1H, d, J=14.3 Hz). ES HRMS: calc'd for C$_{22}$H$_{23}$N$_5$O$_5$S+H 470.1493, observed 470.1478.

EXAMPLE 12

Sodium 5-[(ethylsulfonyl)(methyl)amino]-7-[({4-fluoro-2-[(methylamino)carbonyl]-benzyl}amino)carbonyl]-1,6-naphthyridin-8-olate

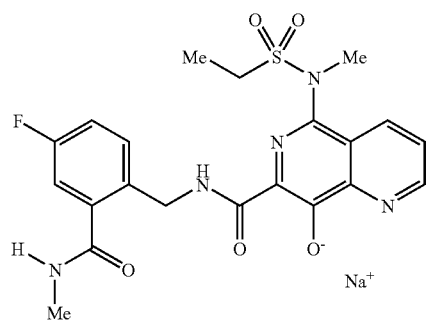

Step, 1: N-methylethanesulfonaide

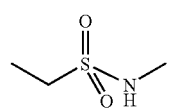

To ethanesulfonyl chloride (10 μm, 77.8 mmol) cooled to zero degrees was added dropwise a 14% weight solution of methylamine in water (100 mL). The reaction was stirred in a 90 degree oil bath for 1 hour and then cooled and extracted with methylene chloride. The organic was dried over magnesium sulfate and carefully evaporated under reduced pressure to give the desired product as a volatile oil.

$^1$H NMR (DMSO-d6, 400 MB) δ 4.72 (1H, bs), 3.05 (2H, q, J=7.5 Hz), 2.80 (3H, dd, J=5.3, 1.8 Hz), 1.37 (3H, t, J=7.3 Hz) ppm.

Step 2: Methyl 5-[(ethylsulfonyl)(methyl)amino]-8-{[(4-methylphenyl)sulfonyl]oxy}-1,6-naphthyridine-7-carboxylate

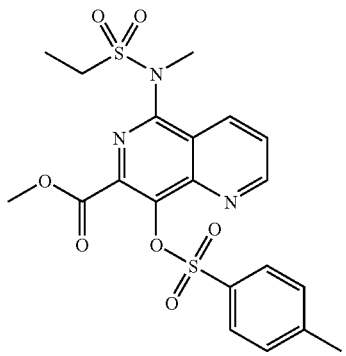

In a dried sealable pressure tube flushed with argon was placed methyl 5-bromo-8-{[(4-methylphenyl)sulfonyl]oxy}-1,6-naphthyridine-7-carboxylate (2.0 g, 4.57 mmol), prepared as described in Example 2, Step 2), N-methylethanesulfonamide (1.13 g, 9.15 mmol), dry DMF (4 mL) and copper(I) oxide (785 mg, 5.49 mmol) and 2,2' bipyridyl (857 mg, 5.49 mmol). The tube was capped and heated to 118° C. for 2 hours. The reaction was cooled and filtered through a glass fiber filter, washing with chloroform. The filtrate was diluted with chloroform (about 100 mL total volume) and stirred with an EDTA solution (5 g EDTA in 100 mL water) for two hours or until the aqueous layer became aqua in color and the organic layer became yellow. The layers were separated and the aqueous layer was extracted twice more with chloroform. The combined organic extracts were dried over sodium sulfate, filtered, and concentrated under reduced pressure. The residue was redissolved in 2 mL of DMSO and purified by preparative HPLC (Gilson semi preparative HPLC system using a Waters Nova pak column (10×40 mm I.D. cartridges, C18, 6 µM pore size) eluting with 95-5% water (0.025% TfEA)/acetonitrile (0.025% TFA) at 35 mLjmin) and the desired fractions were freeze dried to give the product as a yellow powder.

$^1$H NMR (DMSO-d6, 400 MHz) δ 9.03 (1H, dd, J=4.4, 1.6 Hz), 8.65 (1H, dd, J.=8.6, 1.6 Hz), 7.86 (1H, dd, J=8.4, 4.2 Hz), 7.75 (2H, d, J=8.2 Hz), 7.44 (2H, d, J=8.2 Hz), 3.76 (3H, s), 3.55 (2H, q, J=7.5 Hz), 3.39 (3H, s), 2.43 (3H, s), and 1.3 (3H, t, J=7.33 Hz) ppm.

Step 3: Methyl 8-hydroxy-5-[methyl(ethylsulfonyl)amino]-1,6-naphthyridine-7-carboxylate

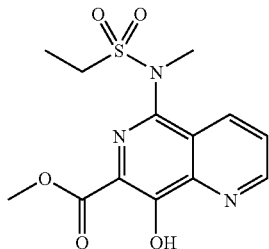

A solution of sodium methoxide (479 mg, 8.86 mmol) in dry methanol (18 mL) was added to methyl 5-[methyl (ethylsulfonyl)amino]-8-{[(4-methylphenyl)sulfonyl]oxy}-1,6-naphthyridine-7-carboxylate (1.7 g, 3.54 mmol) dissolved in a minimum amount of DMF and the resulting solution was heated to 50° C. for 5 minutes. The reaction was cooled, glacial acetic acid (0.433 mL, 7 mmol) was added followed by water (0.936 mL) over 15 minutes at 25 degrees C. The resulting solid was collected by filtration and washed with 1:1 water methanol and dried in vacuo to give the desired product as a yellow solid.

$^1$H NMR (DMSO-d6, 400 MHz) δ 11.55 (1H, bs), 9.22 (1H, dt, J=4.1, 2.8 Hz), 8.60 (1H, d, J=8.4 Hz), 7.94 (1H, dd, J=8.4, 4.2 Hz), 3.94 (3H, d, J=1.3 Hz), 3.50 (2H, q, f=7.2 Hz), 3.29 (3H, bs), 1.31 (3H, t, J=7.3 Hz) ppm.

Step 4: 8-Hydroxy-5-[methyl(ethylsulfonyl)amino]-1,6-naphthyridine-7-carboxylic acid

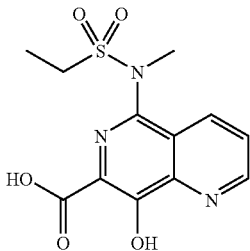

Sodium hydroxide (6.73 mL, 6.73 mmol, 1N solution) was added to a suspension of methyl 8-hydroxy-5-[methyl (ethylsulfonyl)amino]-1,6-naphthyridine-7-carboxylate (730 mg, 2.24 mmol) in a 2:1 solution of dioxane/water (20 mL) and the resulting mixture was heated overnight at 55° C. overnight. The opaque solution was acidified to a pH=7 using 1N HCl solution. The reaction was cooled and the solids that had precipitated out of solution were collected by vacuum filtration to give the desired product as an off-white solid.

$^1$H NMR (DMSO-d6, 400 MHz) δ 9.21 (1H, dd, J=4.4, 1.6 Hz), 8.62 (1H, dd, J=8.4, 1.5 Hz), 7.93 (1H, dd, J=8.4, 4.2 Hz), 3.50 (2H, q, J=7.5 Hz), 3.32 (3H, s), and 1.30 (3H, t, J=7.5 Hz) ppm.

Step 5: 5-[(Ethylsulfonyl)(methyl)amino]-N-{4-fluoro-2-[(methylamino)-carbonyl]benzyl}-8-hydroxy-1,6-naphthyridine-7-carboxamide

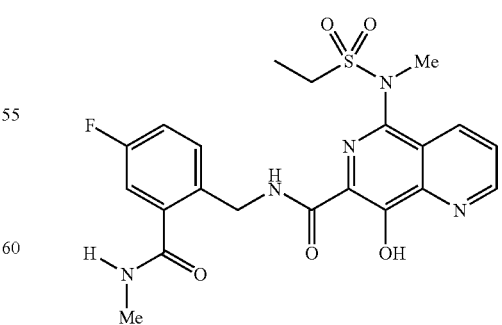

8-Hydroxy-5-[methyl(ethylsulfonyl)amino]-1,6-naphthyridine-7-carboxylic acid was coupled with {2-[(methylamino)carbonyl]4-fluorophenyl}methanaminium chloride (prepared as described in Example 3). A solution of 8-Hydroxy-5-[methyl(ethylsulfonyl)amino]-1,6-naphthyridine-7-carboxylic acid (50 mg, 0.16 mmol) in dry DMF (15 mL) was stirred at zero degrees. To this was added 1-[3-(dimethylamino)propyl]-3-ethylcarbodiimide hydrochloride (40 mg, 0.21 mmol), 1-hydroxy-7-azabenzotriazole (28 mg, 0.21 mmol). The mixture was stirred for 35 minutes at which time the {4-fluoro-2-[(methylamino)carbonyl]phenyl}-methanaminium chloride (38 mg, 0.21 mmol) and diisopropylethylamine (27 mg, 0.21 mmol) was added and the reaction was stirred at room temperature overnight. The reaction was filtered through a glass fiber filter. The filtrate was vacuum reduced and purified by preparative HPLC (Gilson semi preparative HPLC system using a Waters Nova pak column (10×40 mm I.D. cartridges, C18, 6 μM pore size) eluting with 95-5% water (0.025% TFA)/acetonitrile (0.025% TFA) at 35 mL/min). The desired fractions were freeze dried to give the desired product as a white solid.

$^1$H NMR (CDCl$_3$, 400 MHz) δ 9.37 (1H, m), 9.19 (1H, m), 8.74 (1H, dd, J=8.5, 1.3 Hz), 7.71 (1H, dd, J=8.4, 4.2 Hz), 7.60 (1H, m), 7.18 (1H, s), 7.16 (1H, s), 6.65 (1H, m), 4.63 (2H, d, J=6.5 Hz), 3.43 (2H, q, J=7.4 Hz), 3.42 (3H, s), 3.04 (3H, d, J=4.7 Hz), and 1.44 (3H, t, J=7.5 Hz) ppm. LC/MS: calc'd for C$_{21}$H$_{22}$FN$_5$O$_5$S 475.13, observed MH+476.14.

Step 6: Sodium 7-[({2-[(methylamino)carbonyl]-4-fluorobenzyl}amino)carbonyl]-5-[methyl(ethylsulfonyl)amino]-1,6-naphthyridin-8-olate In a manner similar to that described for Example 3, the free acid was converted to the desired salt, that was obtained as a crystalline yellow solid from methanol.

$^1$H NMR (DMSO-d6, 400 MHz) δ 12.26 (1H, m), 8.78 (1H, m), 8.73 (1H, m), 8.23 (1H, dd, J=8.2, 1.5 Hz), 7.52 (1H, dd, J=8.4, 4.2 Hz), 7.45 (1H, dd, J=8.4, 5.7 Hz), 7.23 (1H, dt, J=8.4, 5.9 Hz), 7.18 (1H, dd, J=9.3, 2.9 Hz), 4.58 (2H, d, J=5.9 Hz), 3.51 (2H, q, J=7.3 Hz), 3.18 (3H, s), 2.81 (3H, d, J=4.4 Hz), and 1.30 (3H, t, J=7.5 Hz) ppm. ES HRMS: calc'd for C$_{21}$H$_{21}$FN$_5$NaO$_5$S 476.1388, observed 476.1414.

EXAMPLE 13

Sodium 7-[({4-fluoro-2-[(methylamino)carbonyl] benzyl}amino)carbonyl]-5-(6-methyl-1,1-dioxido-1,2,6-thiadiazinan-2-yl)-1,6-naphthyridin-8-olate

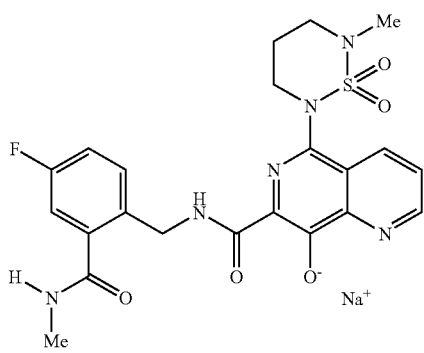

Step 1: 2-Methyl-1,2,6-thiadiazinane 1,1-dioxide

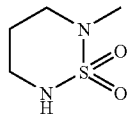

In a dry flask was combined under argon N-methyl-1,3-propanediamine 27.5 gm, 312 mmol) and sulfamide (10 μm, 104 mmol) and the flask was heated overnight to 50 degrees. The amine was removed under reduced pressure to give a gel which was washed with hexane and ether. The residue was chromatographed on silica gel (1 kg) eluting with 50% ethyl acetate and methylene chloride. The colorless band eluting first was collected and reduced to give the desired product as an oil.

$^1$H NMR (CDCl$_3$, 400 MHz) δ 4.06 (1H, bs), 3.52 (2H, m), 3.30 (2H, t, J=5.7 Hz), 2.76 (3H, s), and 1.79 (2H, m).

Step 2: Methyl 8-hydroxy-5-(6-methyl-1,1-dioxido-1,2,6-thiadiazinan-2-yl)-1,6-naphthyridine-7-carboxylate

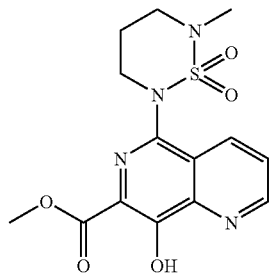

In a dried sealable pressure tube flushed with argon was placed methyl 5-bromo-1,6-naphthyridine-7-carboxylate (0.6 gms, 2.12 mmol), prepared as described in Example 2, Step 1,2-Methyl-1,2,6-thiadiazinane 1,1-dioxide (955 mg, 6.36 mmol), dry pyridine (2 mL) and copper(I) oxide (303 mg, 2.12 mmol). The tube was capped and heated to 118° C. overnight. The reaction was cooled and filtered through a glass fiber filter, washing with chloroform. The filtrate was diluted with chloroform (about 300 mL total volume) and stirred with an EDTA solution (15 g EDTA in 300 mL water) for two hours or until the aqueous layer became aqua in color and the organic layer became yellow. The layers were separated and the aqueous layer was extracted twice more with chloroform. The combined organic extracts were dried over sodium sulfate, filtered, and concentrated under reduced pressure. The residue crystallized from a small amount of methanol and was filtered and washed with methanol and dried in vacuo to give the desired product as a pale yellow solid.

$^1$H NMR (CDCl$_3$, 400 MHz) δ 11.75 (1H, s), 9.18 (1H, dt, J=4.2, 1.6 Hz), 8.69 (1H, dt, J=8.5, 1.5 Hz), 7.70 (1H, m), 4.12 (2H, m), 4.08 (3H, s), 3.80 (2H, m) and 2.95 (3H, s), 1.5 (2H, buried) ppm.

Step 3: 8-Hydroxy-5-(6-methyl-1,1-dioxido-1,2,6-thiadiazinan-2-yl)-1,6-naphthyridine-7-carboxylic acid

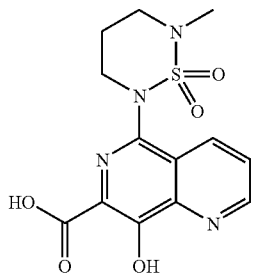

Sodium hydroxide (3.85 mL, 3.85 mmol, 1N solution) was added to a suspension of methyl 8-hydroxy-5-(6-methyl-1,1-dioxido-1,2,6-thiadiazinan-2-yl)-1,6-naphthyridine-7-carboxylate (452 mg, 1.28 mmol) in a 2:1 solution of dioxane/water (10 mL) and the resulting mixture was heated overnight at 55° C. overnight. The opaque solution was acidified to a pH=7 using 1N HCl solution. The reaction was cooled and the solids that had precipitated out of solution were collected by vacuum filtration to give the desired product as an off-white solid.

$^1$H NMR (DMSO-d6, 400 MHz) δ 9.19 (1H, dd, J=4.2, 1.5 Hz), 8.64 (1H, dd, J=8.4, 1.5 Hz), 7.91 (1H, dd, J=8.6, 4.2 Hz), 4.0 (2H, m), 3.70 (2H, t, J=5.7 Hz), 2.97 (3H, s), 2.4-2.0 (2H, m) ppm.

Step 4: N-{4-Fluoro-2-[(methylamino)carbonyl]benzyl}-8-hydroxy-5-(6-methyl-1,1-dioxido-1,2,6-thiadiazinan-2-yl)-1,6-naphthyridine-7-carboxamide

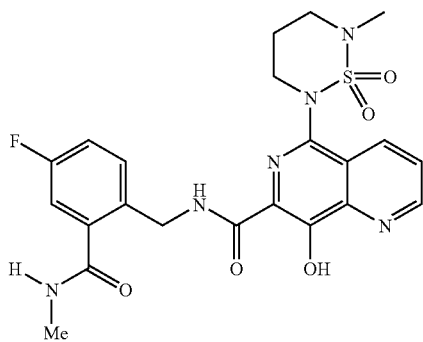

8-Hydroxy-5-(6-methyl-1,1-dioxido-1,2,6-thiadiazinan-2-yl)-1,6-naphthyridine-7-carboxylic acid was coupled with {2-[(methylamino)carbonyl]4 fluorophenyl}methanaminium chloride (prepared as described in Example 3). A solution of 8-hydroxy-5-(6-methyl-1,1-dioxido-1,2,6-thiadiazinan-2-yl)-1,6-naphthyridine-7-carboxylic acid (200 mg, 0.59 mmol) in dry DMF (2 mL) was stirred at zero degrees. To this was added 1-[3-(dimethylamino)propyl]-3-ethylcarbodiimide hydrochloride (147 mg, 0.77 mmol), 1-hydroxy-7-azabenzotriazole (181 mg, 1.18 mmol). The mixture was stirred for 35 minutes at which time the {4-fluoro-2-[(methylamino)carbonyl]phenyl}-methanaminium chloride (194 mg, 0.89 mmol) and diisopropylethylamine (124 μL, 0.7 mmol) was added and the reaction was stirred at room temperature for 1 hour. The reaction was filtered through a glass fiber filter. The filtrate was injected directly into the preparative HPLC (Gilson semi preparative HPLC system using a Waters Nova pak column (10×40 mm I.D. cartridges, C18, 6 μM pore size) eluting with 95-5% water (0.025% TFA)/acetonitrile (0.025% TFA) at 35 mL/min). The desired fractions were freeze dried to give the desired product as a white solid.

$^1$H NMR (CDCl$_3$, 400 M) δ 13.4 (1H, bs), 9.15 (2H, dd, J=4.2, 1.5 Hz), 9.10 (1H, m), 8.60 (1H, dd, J=8.6, 1.6 Hz), 7.65 (1H, dd, J=8.4, 4.2 Hz), 7.60 (1H, dd, J=7.9, 5.5 Hz), 7.26 (1H, m), 6.18 (1H, m), 4.68 (2H, d, J=6.6 Hz), 4.68 (2H, d, J=6.6 Hz), 4.10 (2H, bs), 3.8 (2H, bs), 3.03 (3H, dd, J=4.9, 1.8 Hz) and 2.95 (3H, d, J=1.6) ppm. LC/MS: calc'd for C$_{22}$H$_{23}$FN$_6$O$_5$S calculated mass 502.14 observed MH+ 503.14

Step 5: Sodium 7-[({4-fluoro-2-[(methylamino)carbonyl]benzyl}amino)-carbonyl]-5-(6-methyl-1,1-dioxido-1,2,6-thiadiazinan-2-yl)-1,6-naphthyridin-8-olate In a manner similar to that described for Example 3, the free acid was converted to the desired salt, that was obtained as a crystalline yellow solid from methanol.

$^1$H NMR (DMSO-d6, 400 MHz) δ 12.40 (1H, bs), 8.77 (2H, m), 8.30 (1H, d, J=8.1 Hz), 7.50 (2H, m), 7.20 (2H, t, J=11.2 Hz), 4.58 (2H, d, J=5.4 Hz), 3.91 (1H, bs), 3.72 (1H, bs), 3.60 (2H, m), 2.96 (3H, s), 2.81(3H, dd, J=4.4, 1.8 Hz), 2.5 (1H, buried) and 1.82 (1H, m) ppm. ES HRMS: calc'd for C22H22FN6NaO5S 503.1507, observed 503.1510.

EXAMPLE 14

Oral Compositions

As a specific embodiment of an oral composition of a compound of this invention, 50 mg of compound of Example 3 is formulated with sufficient finely divided lactose to provide a total amount of 580 to 590 mg to fill a size 0 hard gelatin capsule. Encapsulated oral compositions containing any one of the compounds of Examples 3C and 4-13 can be similarly prepared.

EXAMPLE 15

HIV Integrase Assay: Strand Transfer Catalyzed by Recombinant Integrase

Assays for the strand transfer activity of integrase were conducted in accordance with the method described in Example 193 of WO 02/30930 for recombinant integrase. Representative compounds of the present invention exhibit inhibition of strand transfer activity in this assay. For example, the compounds prepared in Examples 3, 3C and 4-13 were tested in the integrase assay and all were found to have IC$_{50}$'s less than 0.5 micromolar.

Further description on conducting the assay using preassembled complexes is found in Wolfe, A. L. et al., *J. Virol.* 1996, 70: 1424-1432, Hazuda et al., *J. Virol.* 1997, 71: 7005-7011; Hazuda et al., *Drug Design and Discovery* 1997, 15: 17-24; and Hazuda et al., *Science* 2000, 287: 646-650.

EXAMPLE 16

Assay for inhibition of HIV replication

Assays for the inhibition of acute HIV infection of T-lymphoid cells were conducted in accordance with Vacca, J. P. et al., *Proc. Natl. Acad. Sci. USA* 1994, 91: 4096. Representative compounds of the present invention exhibit inhibition of HIV replication in this assay. For example, the compounds prepared in Examples 3, 3C and 4-13 were tested in the present assay and all were found to have $IC_{95}$'s less than 5 micromolar.

While the foregoing specification teaches the principles of the present invention, with examples provided for the purpose of illustration, the practice of the invention encompasses all of the usual variations, adaptations and/or modifications that come within the scope of the following claims.

What is claimed is:

1. A compound of Formula (I):

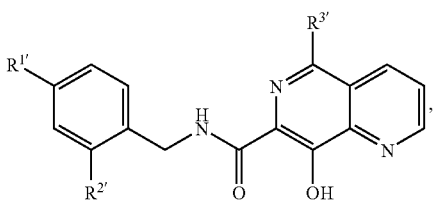

(I)

wherein
R$^{1'}$ is —H or —F;
R$^{2'}$ is
(1) —C$_{1-6}$ alkyl-C(=O)N(R$^a$R$^b$),
(2) —C(=O)N(R$^a$R$^b$),
(3)

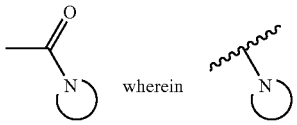

is azetidinyl, pyrrolidinyl, piperidinyl, or morpholino,
(4) triazolyl or tetrazolyl,
(5) —N(R$^a$)—C(R$^b$)=O,
(6)

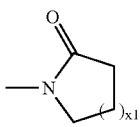

wherein x1 is an integer equal to zero, 1, or 2, or
(7) —CO$_2$R$^c$;
R$^{3'}$ is:
(1) —H,
(2) —C(=O)N(R$^a$R$^b$),
(3) —CH$_2$—C(=O)N(R$^a$R$^b$),
(4) —CH$_2$CH$_2$—C(=O)N(R$^a$R$^b$),
(5) —S—CH$_2$—C(=O)N(R$^a$R$^b$),
(6) —O—CH$_2$—C(=O)N(R$^a$R$^b$),
(7) —N(R$^a$)—C(R$^b$)=O,
(8) —N(SO$_2$R$^c$)—CH$_2$—C(=O)N(R$^a$R$^b$),
(9) —N(R$^a$)—C(=O)—C(=O)N(R$^a$R$^b$),
(10) —N(R$^a$)SO$_2$R$^c$,
(11) —CH=CH—C(=O)—N(R$^a$R$^b$),
(12) —N(R$^a$)—CH$_2$—C(=O)N(R$^a$R$^b$),
(13) —N(R$^a$)—C(=O)—N(R$^a$R$^b$),
(14) -HetC',
(15) —(CH$_2$)$_{1-3}$ alkyl-HetC',
(16) —N(R$^a$)—(CH$_2$)$_{1-3}$-HetC',
(17) —N(R$^a$)—SO$_2$—N(R$^a$R$^b$),
(18) -HetQ',
(19)

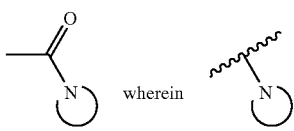

is as defined above in R$^{2'}$, or
(20)

is as defined above in R$^{2'}$;

HetC' is a 5- to 7-membered saturated heterocyclic ring containing from 1 to 4 heteroatoms independently selected from N, O and S, wherein the saturated heterocyclic ring is optionally substituted with from 1 to 4 substituents each of which is independently halogen, —C$_{1-4}$ alkyl, —C$_{3-6}$ cycloalkyl, —O—C$_{1-4}$ alkyl, —C$_{1-4}$ haloalkyl, —O—C$_{1-4}$ haloalkyl, —CN, oxo, phenyl, benzyl, phenylethyl, —(CH$_2$)$_{0-3}$C(=O)N(R$^a$R$^b$), —(CH$_2$)$_{0-3}$C(=O)R$^a$, —N(R$^a$)—C(=O)R$^b$, —N(R$^a$)—CO$_2$R$^b$, —(CH$_2$)$_{1-3}$N(R$^a$)—C(=O)R$^b$, —N(R$^a$R$^b$), —(CH$_2$)$_{1-3}$N(R$^a$R$^b$), —SO$_2$R$^c$, —(CH$_2$)$_{0-3}$C(=O)-HetD', —HetD', —N(R$^a$)-HetD', and —(CH$_2$)$_{1-3}$-HetD'; wherein each HetD' is independently a 5- or 6-membered heteroaromatic ring containing from 1 to 4 nitrogen atoms or a 5- or 6-membered saturated heterocyclic ring containing from 1 to 4 nitrogen atoms, wherein the ring is optionally substituted with 1 or 2 substituents each of which is independently halogen, oxo, —C$_{1-4}$ alkyl, or —O—C$_{1-4}$ alkyl;

HetQ' is a 7- to 9-membered bridged azabicycloalkyl saturated ring system containing a C$_{5-7}$ azacycloalkyl ring in which two of the ring carbons are connected by a bridge containing 1 or 2 carbon atoms; wherein the bridged azabicycloalkyl ring system is optionally substituted with from 1 to 4 substituents each of which is independently halogen, oxo, or —C$_{1-4}$ alkyl;

each R$^a$ is independently —H, —C$_{1-6}$ alkyl, or —C$_{3-6}$ cycloalkyl;

each R$^b$ is independently —H, —C$_{1-6}$ alkyl, or —C$_{3-6}$ cycloalkyl; and each R$^c$ is independently a —C$_{1-6}$ alkyl or —C$_{3-6}$ cycloalkyl;

or a pharmaceutically acceptable salt thereof.

2. The compound according to claim 1, wherein R$^{2'}$ is —(CH$_2$)$_{1-3}$—C(=O)N(R$^a$R$^b$), —C(=O)N(R$^a$R$^b$),

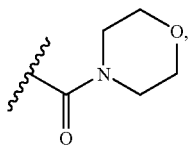

triazolyl, or tetrazolyl;
or a pharmaceutically acceptable salt thereof.

3. The compound according to claim 2, wherein
R$^{2'}$ is —(CH$_2$)$_{1-3}$—C(=O)N(R$^a$*R$^b$*), —C(=O)N(R$^a$*R$^b$*),

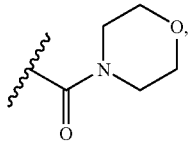

triazolyl, or tetrazolyl;
R$^a$* and R$^b$* are each independently —H, —C$_{1-4}$ alkyl, or cyclopropyl, with the proviso that R$^a$* and R$^b$* are not both —H;
each R$^a$ in R$^{3'}$ is independently —H, —C$_{1-4}$ alkyl, or cyclopropyl;
each R$^b$ in R$^{3'}$ is independently —H, —C$_{1-4}$ alkyl, or cyclopropyl; and
each R$^c$ in R$^{3'}$ is independently a —C$_{1-4}$ alkyl or cyclopropyl;
or a pharmaceutically acceptable salt thereof.

4. The compound according to claim 3, wherein R$^{2'}$ is —(CH$_2$)$_{1-3}$—C(=O)N(R$^a$*R$^b$*) or —C(=O)N(R$^a$*R$^b$*); and
one of R$^a$* and R$^b$* is —H, and the other of R$^a$* and R$^b$* is —C$_{1-4}$ alkyl or cyclopropyl;
or a pharmaceutically acceptable salt thereof.

5. The compound according to claim 1, wherein
HetC' in the definition of R$^{3'}$ is a saturated heterocyclic ring selected from piperidinyl, morpholinyl, thiomorpholinyl, thiazolidinyl, isothiazolidinyl, oxazolidinyl, isooxazolidinyl, pyrrolidinyl, imidazolidinyl, piperazinyl, tetrahydrofuranyl, pyrazolidinyl, hexahydropyrimidinyl, thiazinanyl, thiazepanyl, thiadiazepanyl, dithiazepanyl, diazepanyl, and thiadiazinanyl, wherein the saturated heterocyclic ring is unsubstituted or substituted with 1 to 4 substituents each of which is independently:
(a) methyl or ethyl,
(b) =O,
(c) —C(=O)N(R$^a$R$^b$),
(d) —CH$_2$C(=O)N(R$^a$R$^b$),
(e) —C(=O)R$^a$, or
(f) —SO$_2$R$^c$;
or a pharmaceutically acceptable salt thereof.

6. The compound according to claim 1, wherein R$^{3'}$ is —H, —C(=O)N(R$^a$R$^b$), —N(R$^a$)SO$_2$R$^c$, —N(R$^a$)—C(=O)—C(=O)—N(R$^a$R$^b$), 1,1-dioxido-1,2-thiazinan-2-yl, 1,1-dioxidoisothiazolidin-2-yl, 1,1-dioxido-1,2,6-thiadiazinan-2-yl, 6-methyl-1,1-dioxido-1,2,6-thiadiazinan-2-yl, or 3-oxo-2-azabicyclo[2.2.1]hept-2-yl;
or a pharmaceutically acceptable salt thereof.

7. The compound according to claim 1, wherein:
R$^{1'}$ is —H or —F;
R$^{2'}$ is
(1) —(CH$_2$)$_{1-3}$—C(=O)N(R$^a$*R$^b$*),
(2) —C(=O)N(R$^a$*R$^b$*),
(3) —C(=O)NH$_2$,
(4)

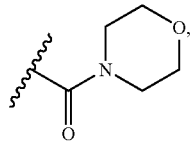

(5) triazolyl, or
(6) tetrazolyl;
R$^{3'}$ is:
(1) —H,
(2) —C(=O)N(R$^{a''}$R$^{b''}$),
(3) —CH$_2$—C(=O)N(R$^{a''}$R$^{b''}$),
(4) —CH$_2$CH$_2$—C(=O)N(R$^{a''}$R$^{b''}$),
(5) —N(R$^a$)—C(R$^b$)=O,
(6) —N(R$^a$)—C(=O)—C(=O)—N(R$^a$R$^b$),
(7) —N(R$^a$)SO$_2$R$^c$,
(8) -HetC', or
(9) -HetQ';
HetC' is a saturated heterocyclic ring selected from thiazinanyl, isothiazolidinyl, and thiadiazinanyl, wherein the saturated heterocyclic ring is optionally substituted with from 1 to 4 substituents each of which is independently —C$_{1-4}$ alkyl or oxo;
HetQ' is azabicyclo[2.2.1]heptyl optionally substituted with 1 or 2 substituents each of which is independently oxo or —C$_{1-4}$ alkyl;
one of R$^a$* and R$^b$* is —H, —C$_{1-4}$ alkyl, or cyclopropyl, and the other of R$^a$* and R$^b$* is —C$_{1-4}$ alkyl or cyclopropyl;
each of R$^{a''}$ and R$^{b''}$ is independently —C$_{1-4}$ alkyl or cyclopropyl;
each of R$^a$ and R$^b$ is independently —H, —C$_{1-4}$ alkyl, or cyclopropyl; and
R$^c$ is —C$_{1-4}$ alkyl or cyclopropyl;
or a pharmaceutically acceptable salt thereof.

8. The compound according to claim 7, wherein
R$^{1'}$ is —H or —F;
R$^{2'}$ is:
(1) —CH$_2$C(=O)N(R$^a$*R$^b$*),
(2) —C(=O)N(R$^a$*R$^b$*),
(3) —C(=O)NH$_2$,
(4)

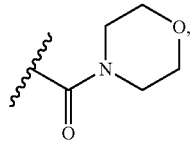

(5) triazolyl, or
(6) tetrazolyl;
R$^{3'}$ is:
(1) —C(=O)N(R$^{a''}$R$^{b''}$),
(2) —CH$_2$—C(=O)N(R$^{a''}$R$^{b''}$),
(3) —CH$_2$CH$_2$—C(=O)N(R$^{a''}$R$^{b''}$),
(4) —N(R$^a$)—C(R$^b$)=O,
(5) —N(R$^a$)—C(=O)—C(=O)—N(R$^a$R$^b$), (6) —N(R$^a$)SO$_2$R$^c$,
(7) 1,1-dioxido-1,2-thiazinan-2-yl,
(8) 1,1-dioxidoisothiazolidin-2-yl,
(9) 1,1-dioxido-1,2,6-thiadiazinan-2-yl,
(10) 6-methyl-1,1-dioxido-1,2,6-thiadiazinan-2-yl, or
(11) 3-oxo-2-azabicyclo[2.2.1]hept-2-yl;

one R$^{a*}$ and R$^{b*}$ is —H, —C$_{1-3}$ alkyl, or cyclopropyl, and the other of R$^{a*}$ and R$^{b*}$ is —C$_{1-3}$ alkyl;
each of R$^{a''}$ and R$^{b''}$ is independently a —C$_{1-3}$ alkyl;
each of R$^a$ and R$^b$ is independently a —C$_{1-3}$ alkyl; and
R$^c$ is —C$_{1-3}$ alkyl;
or a pharmaceutically acceptable salt thereof.

9. The compound according to claim 8, wherein
R$^{1'}$ is —H or —F;
R$^{2'}$is:
(1) —CH$_2$C(=O)NH(CH$_3$),
(2) —CH$_2$C(=O)N(CH$_3$)$_2$,
(3) —C(=O)NH(CH$_3$),
(4) —C(=O)N(CH$_3$)$_2$,
(5) —C(=O)NH(CH$_2$CH$_3$),
(6) —C(=O)NH(CH$_2$CH$_2$CH$_3$),
(7) —C(=O)NH(CH(CH$_3$)$_2$),
(8) —CH$_2$C(=O)NH(cyclopropyl),
(9) —C(=O)NH$_2$,
(10)

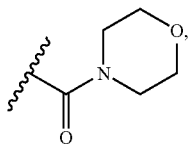

(11) triazolyl, or
(12) tetrazolyl; and
R$^{3'}$is:
(1) —C(=O)N(CH$_3$)$_2$,
(2) —N(CH$_3$)—C(CH$_3$)=O,
(3) —N(CH$_3$)—C(=O)—C(=O)—N(CH$_3$)$_2$,
(4) —N(CH$_3$)SO$_2$CH$_3$,
(5) —N(CH$_3$)SO$_2$CH$_2$CH$_3$,
(6) —N(CH$_2$CH$_3$)SO$_2$CH$_3$,
(7) 1,1-dioxido-1,2-thiazinan-2-yl,
(8) 1,1-dioxidoisothiazolidin-2-yl,
(9) 6-methyl-1,1-dioxido-1,2,6-thiadiazinan-2-yl, or
(10) 3-oxo-2-azabicyclo[2.2.1]hept-2-yl;
provided that:
(i) when R$^{3'}$ is —C(=O)N(CH$_3$)$_2$, then R$^{2'}$ is not —C(=O)NH$_2$; and
(ii) when R$^{3'}$ is —N(CH$_3$)—C(CH$_3$)=O or —N(CH$_3$)—C(=O)—C(=O)—N(CH$_3$)$_2$, then R$^{2'}$is not —C(=O)N(CH$_3$)$_2$ or —CH$_2$C(=O)N(CH$_3$)$_2$; or a pharmaceutically acceptable salt thereof.

10. The compound according to claim 9, wherein:
R$^{2'}$ is —C(=O)NH$_2$, —C(=O)NH(CH$_3$), —C(=O)N(CH$_3$)$_2$, or —C(=O)NH(CH$_2$CH$_3$); and
R$^{3'}$ is —N(CH$_3$)SO$_2$CH$_3$, —N(CH$_3$)SO$_2$CH$_2$CH$_3$, 1,1-dioxido-1,2-thiazinan-2-yl, or 6-methyl-1,1-dioxido-1,2,6-thiadiazinan-2-yl;
or a pharmaceutically acceptable salt thereof.

11. A compound selected from the group consisting of:
N-{4-fluoro-2-[(methylamino)carbonyl]benzyl}-5-(1,1-dioxido-1,2-thiazinan-2-yl)-8-hydroxy-1,6-naphthyridine-7-carboxamide;
N-{2-[(dimethylamino)carbonyl]-4-fluorobenzyl}-5-(1,1-dioxido-1,2-thiazinan-2-yl)-8-hydroxy-1,6-naphthyridine-7-carboxamide;
N-{2-[(dimethylamino)carbonyl]-4-fluorobenzyl}-5-[methyl(methylsulfonyl)amino]-8-hydroxy-1,6-naphthyridine-7-carboxamide;
N-{4-fluoro-2-[(methylamino)carbonyl]benzyl}-5-[methyl(methylsulfonyl)amino]-8-hydroxy-1,6-naphthyridine-7-carboxamide;
N-{4-fluoro-2-[(isopropylamino)carbonyl]benzyl}-5-(1,1-dioxido-1,2-thiazinan-2-yl)-8-hydroxy-1,6-naphthyridine-7-carboxamide;
N-{4-fluoro-2-[(ethylamino)carbonyl]benzyl}-5-(1,1-dioxido-1,2-thiazinan-2-yl)-8-hydroxy-1,6-naphthyridine-7-carboxamide;
N-[2-(aminocarbonyl)-4-fluorobenzyl]-5-(1,1-dioxido-1,2-thiazinan-2-yl)-8-hydroxy-1,6-naphthyridine-7-carboxamide;
N-{4-fluoro-2-[(amino)carbonyl]benzyl}-5-[methyl(methylsulfonyl)amino]-8-hydroxy-1,6-naphthyridine-7-carboxamide;
5-(1,1-dioxido-1,2-thiazinan-2-yl)-8-hydroxy-N-{2-[(methylamino)carbonyl]benzyl}-1,6-naphthyridine-7-carboxamide;
N-{4-fluoro-2-[(methylamino)carbonyl]benzyl}-5-[(ethylsulfonyl)(methyl)amino]-8-hydroxy-1,6-naphthyridine-7-carboxamide;
N-{4-fluoro-2-[(methylamino)carbonyl]benzyl}-5-(6-methyl-1,1-dioxido-1,2,6-thiadiazinan-2-yl)-8-hydroxy-1,6-naphthyridine-7-carboxamide;
and pharmaceutically acceptable salts thereof.

12. The compound according to claim 11, which is a compound selected from the group consisting of:
N-{4-fluoro-2-[(methylamino)carbonyl]benzyl}-5-(1,1-dioxido-1,2-thiazinan-2-yl)-8-hydroxy-1,6-naphthyridine-7-carboxamide;
N-{2-[(dimethylamino)carbonyl]-4-fluorobenzyl}-5-(1,1-dioxido-1,2-thiazinan-2-yl)-8-hydroxy-1,6-naphthyridine-7-carboxamide;
N-{4-fluoro-2-[(methylamino)carbonyl]benzyl}-5-[methyl(methylsulfonyl)amino]-8-hydroxy-1,6-naphthyridine-7-carboxamide;
N-{4-fluoro-2-[(ethylamino)carbonyl]benzyl}-5-(1,1-dioxido-1,2-thiazinan-2-yl)-8-hydroxy-1,6-naphthyridine-7-carboxamide;
N-[2-(aminocarbonyl)-4-fluorobenzyl]-5-(1,1-dioxido-1,2-thiazinan-2-yl)-8-hydroxy-1,6-naphthyridine-7-carboxamide;
N-{4-fluoro-2-[(amino)carbonyl]benzyl}-5-[methyl(methylsulfonyl)amino]-8-hydroxy-1,6-naphthyridine-7-carboxamide;
5-(1,1-dioxido-1,2-thiazinan-2-yl)-8-hydroxy-N-{2-[(methylamino)carbonyl]benzyl}-1,6-naphthyridine-7-carboxamide;
N-{4-fluoro-2-[(methylamino)carbonyl]benzyl}-5-[(ethylsulfonyl)(methyl)amino]-8-hydroxy-1,6-naphthyridine-7-carboxamide;
N-{4-fluoro-2-[(methylamino)carbonyl]benzyl}-5-(6-methyl-1,1-dioxido-1,2,6-thiadiazinan-2-yl)-8-hydroxy-1,6-naphthyridine-7-carboxamide;
and pharmaceutically acceptable salts thereof.

13. The compound according to claim 12, which is N-{4-fluoro-2-[(methylamino)carbonyl]benzyl}-5-(1,1-dioxido-1,2-thiazinan-2-yl)-8-hydroxy-1,6-naphthyridine-7-carboxamide, having the formula:

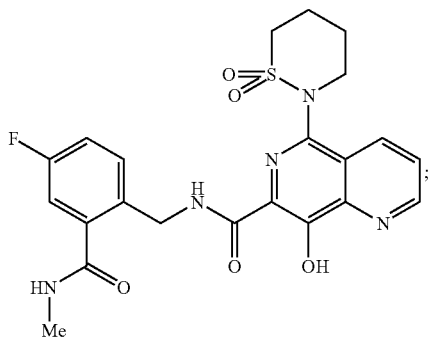

or a pharmaceutically acceptable salt thereof.

14. A pharmaceutical composition comprising a therapeutically effective amount of a compound according to claim 1, or a pharmaceutically acceptable salt thereof, and a pharmaceutically acceptable carrier.

15. A method for treating infection by HIV or for treating or delaying the onset of AIDS in a subject in need thereof which comprises administering to the subject a therapeutically effective amount of the compound according to claim 1, or a pharmaceutically acceptable salt thereof.

16. A combination which comprises a therapeutically effective amount of a compound according to claim 1, or a pharmaceutically acceptable salt thereof, and a therapeutically effective amount of an HIV infection/AIDS antiviral agent selected from the group consisting of HIV protease inhibitors, non-nucleoside HIV reverse transcriptase inhibitors and nucleoside HIV reverse transcriptase inhibitors.

* * * * *